United States Patent
Iizuka et al.

(10) Patent No.: US 6,888,119 B2
(45) Date of Patent: May 3, 2005

(54) LIGHT SCANNING PROBE APPARATUS USING LIGHT OF LOW COHERENCE

(75) Inventors: Shuhei Iizuka, Hachioji (JP); Akihiro Horii, Hachioji (JP); Yasushige Ishihara, Hachioji (JP); Raifu Matsui, Hachioji (JP); Mamoru Kaneko, Hachioji (JP)

(73) Assignee: Olympus Corporation (JP)

( * ) Notice: Subject to any disclaimer, the term of this patent is extended or adjusted under 35 U.S.C. 154(b) by 0 days.

(21) Appl. No.: 10/753,129

(22) Filed: Jan. 6, 2004

(65) Prior Publication Data

US 2004/0140425 A1 Jul. 22, 2004

Related U.S. Application Data

(62) Division of application No. 10/091,626, filed on Mar. 6, 2002, now Pat. No. 6,797,931.

(30) Foreign Application Priority Data

Mar. 12, 2001 (JP) .......................................... 2001-069107

(51) Int. Cl.7 ................................................. G02B 7/04
(52) U.S. Cl. .................................... 250/201.3; 250/239
(58) Field of Search ............................. 250/201.3, 239, 250/235, 306, 307, 363.02; 600/160, 170, 175, 176, 476, 459

(56) References Cited

U.S. PATENT DOCUMENTS

| 5,321,501 A | 6/1994 | Swanson et al. |
| 6,527,708 B1 * | 3/2003 | Nakamura et al. .......... 600/160 |

FOREIGN PATENT DOCUMENTS

| JP | 6-511312 | 12/1994 |
| JP | 11-56786 | 3/1999 |
| WO | 97/32182 | 9/1997 |

* cited by examiner

*Primary Examiner*—Que T. Le
(74) *Attorney, Agent, or Firm*—Ostrolenk, Faber, Gerb & Soffen, LLP

(57) ABSTRACT

A flexible shaft driven to rotate is inserted through a transparent sheath having pliability. By a fiber inserted through the inside thereof, low-coherence light is guided and is made to exit to a living-body tissue side which is an observation target through a lens and a prism forming an exit and entrance portion at the tip portion. Subsequently, the light reflected on the living-body tissue side is guided in order to produce an image. In that case, a positioning member for keeping the exit and entrance portion and the living-body tissue at a proper distance is formed at the tip portion of the sheath or the tip portion of an endoscope through which an optical probe is inserted and, therefore, a stable tomogram image can be produced.

8 Claims, 39 Drawing Sheets

FIG.4A
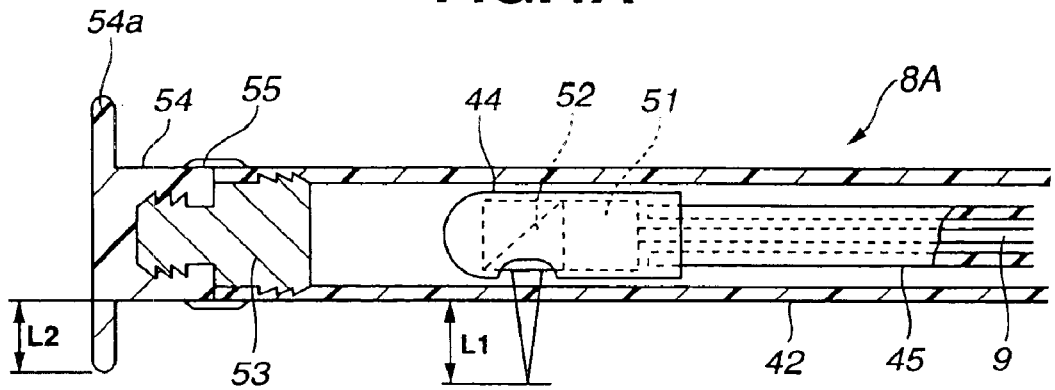
FIG.4B
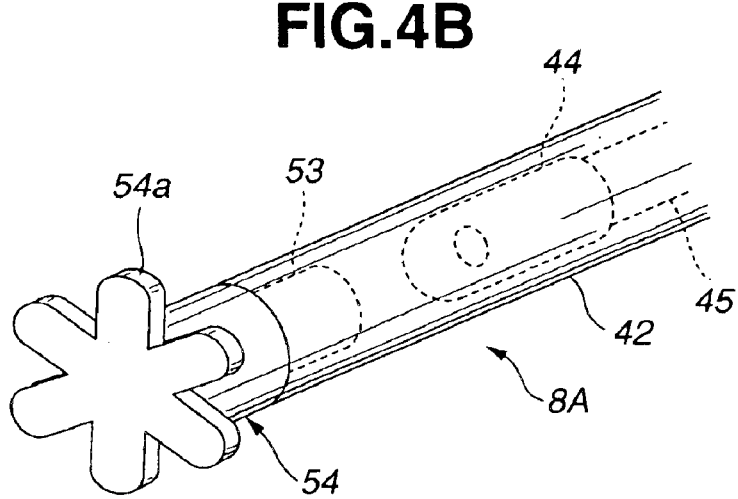
FIG.7A
FIG.7B
(PRIOR ART)
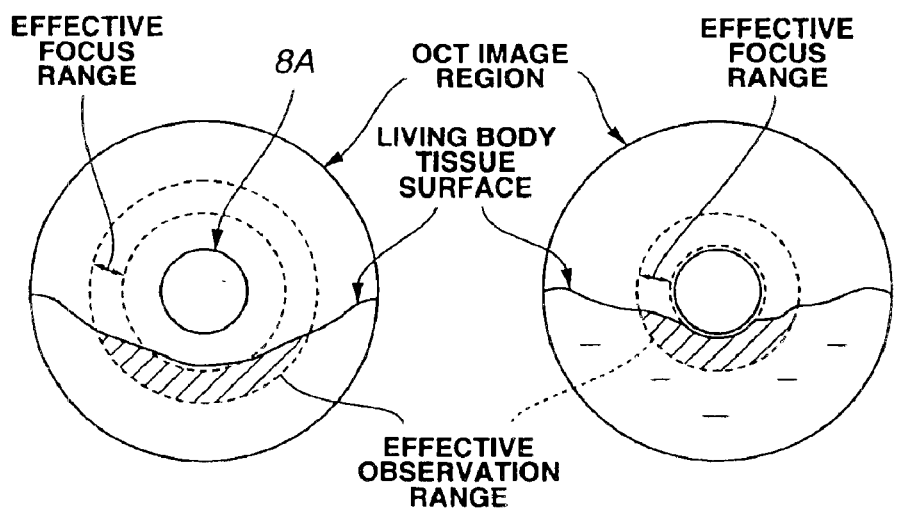

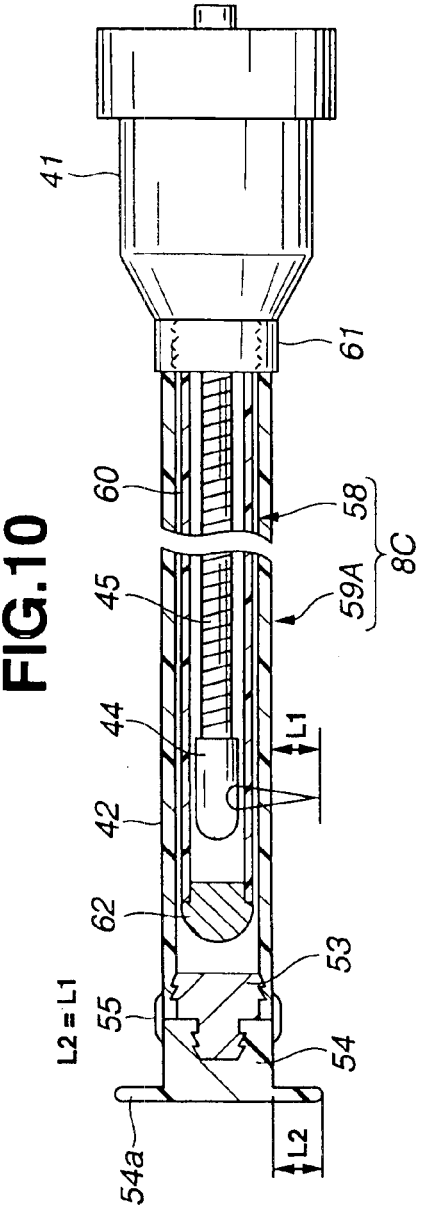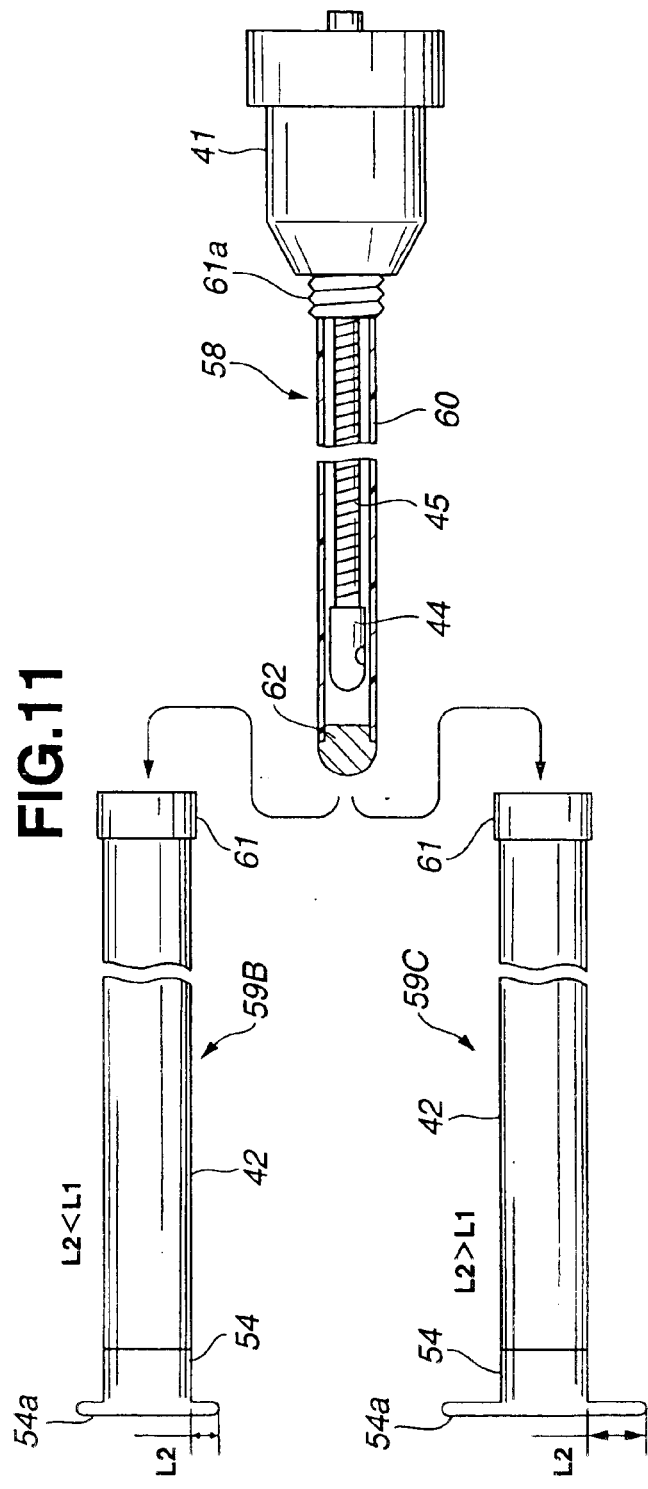

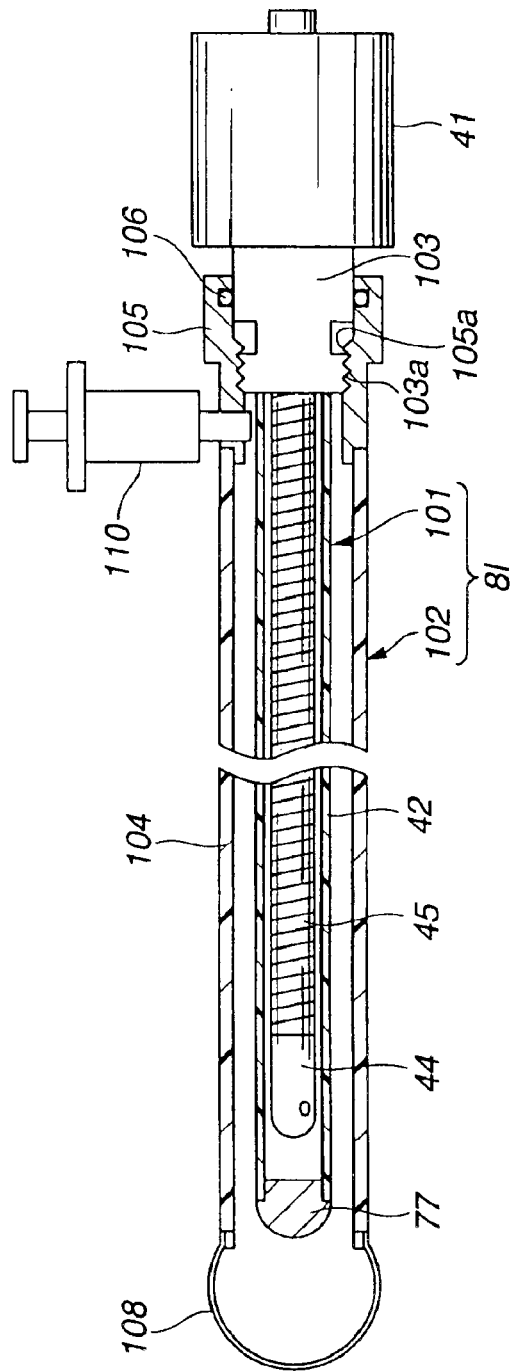
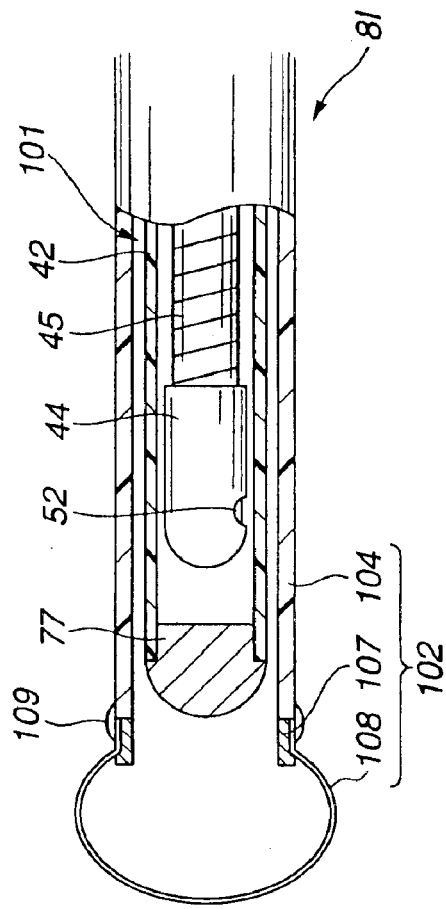
FIG.17
FIG.18

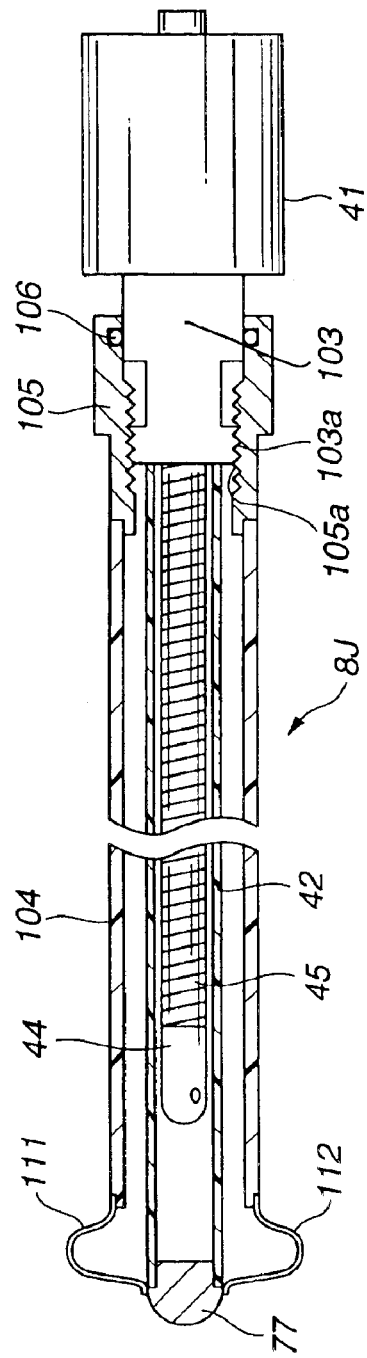
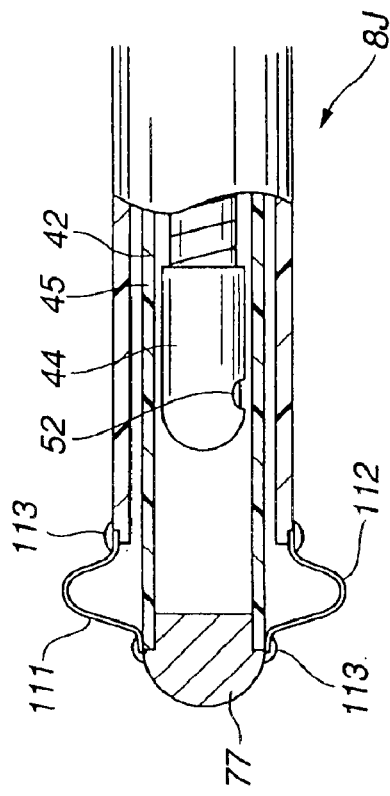
FIG.19
FIG.20 a < b ⇒ F1 > F2

FIG.48B FIG.48A
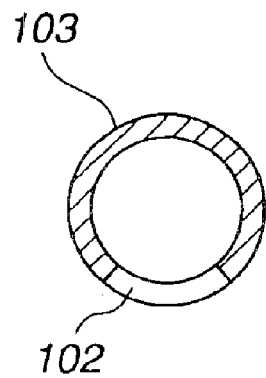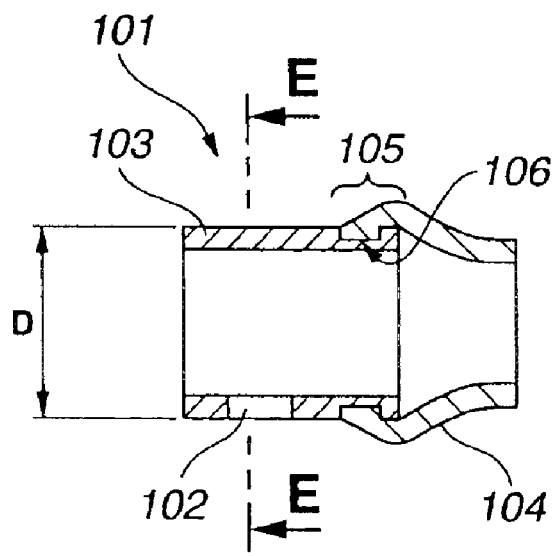
FIG.49
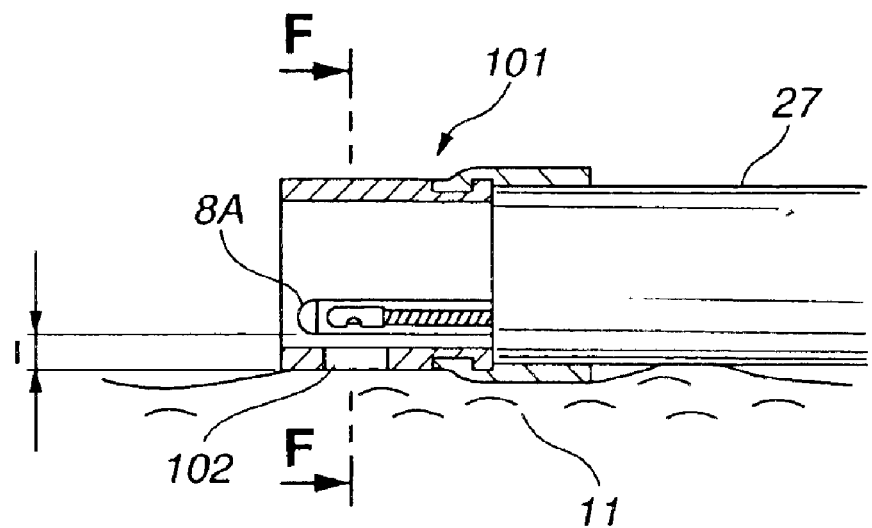

FIG.68B FIG.68A
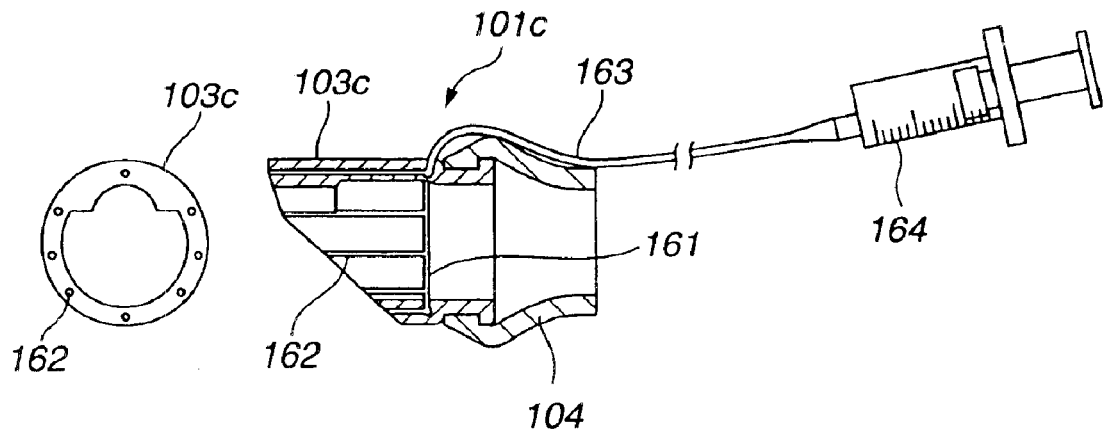
FIG.69
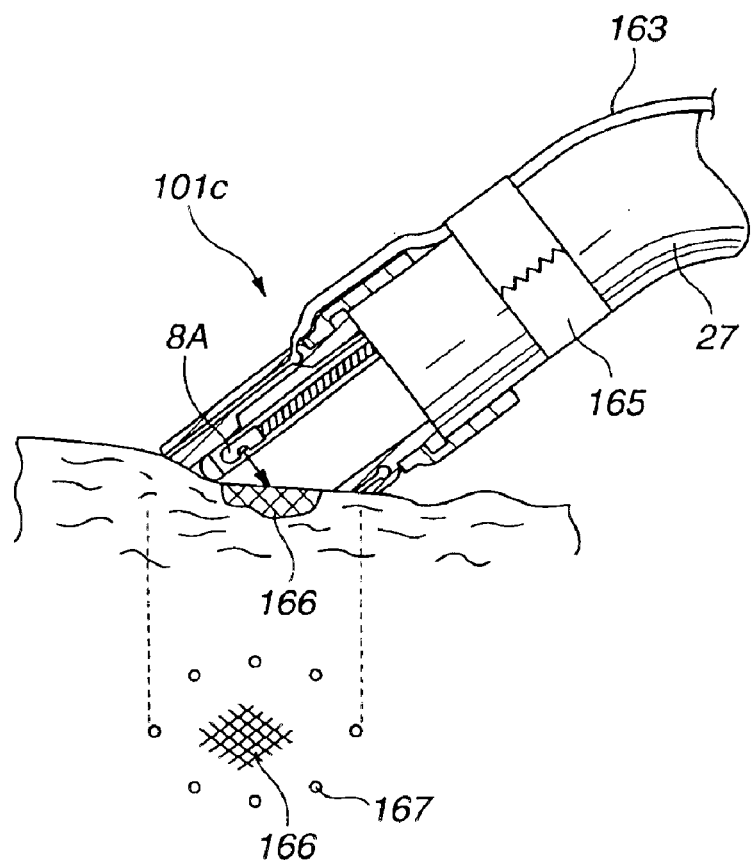

FIG.73B FIG.73A
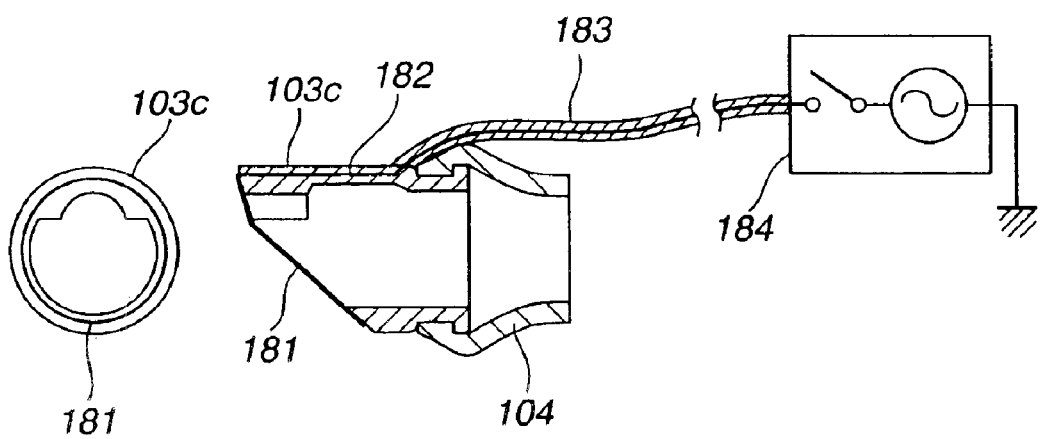
FIG.74
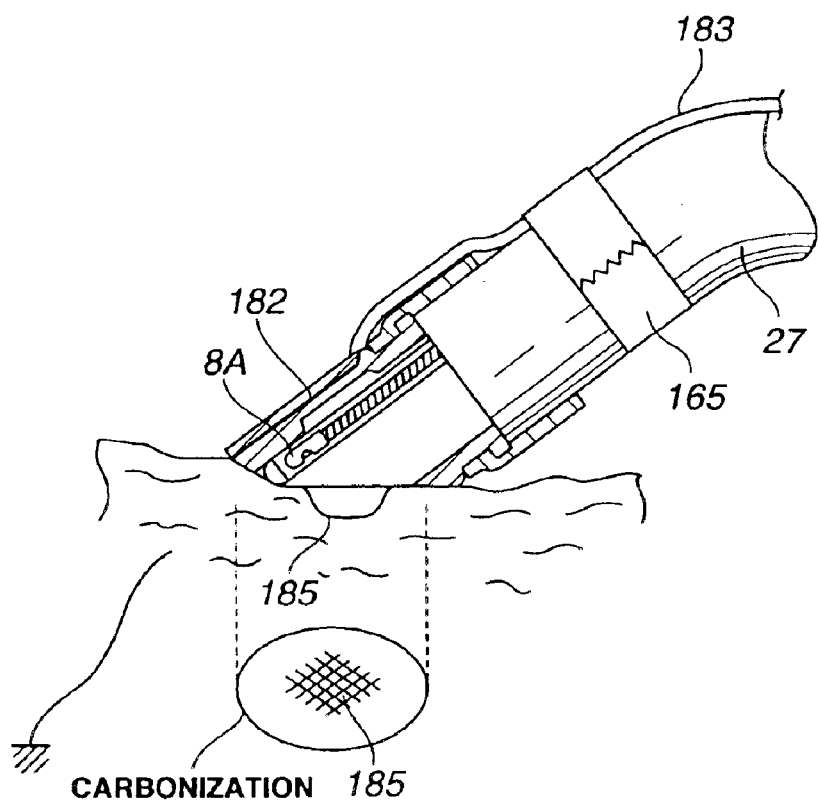
CARBONIZATION

LIGHT SCANNING PROBE APPARATUS USING LIGHT OF LOW COHERENCE

CROSS REFERENCE TO RELATED APPLICATION

This application is a divisional of U.S. application Ser. No. 10/091,626 filed Mar. 6, 2002 now U.S. Pat. No. 6,797,931 entitled LIGHT SCANNING PROBE APPARATUS USING LIGHT OF LOW COHERENCE, which claims the benefit of Japanese Application Nos. 2000-186664 filed on Jun. 21, 2000 and 2001-069107 filed on Mar. 12, 2001, the contents of which are incorporated by this reference.

BACKGROUND OF THE INVENTION

1. Field of the Invention

The present invention relates to an optical scanning probe device in which low-coherence light is guided and is made to exit to living-body tissue, and reflected light therefrom is guided so as to produce an optical tomogram.

2. Description of Related Art

In recent years, in the case where living-body tissue is diagnosed, in addition to an imaging device to gain optical information regarding the surface condition of the tissue, an optical CT device which can gain optical information regarding the inside of the tissue has been suggested.

In this optical CT device, picosecond pulses are used for detecting information regarding the inside of a living body and, therefore, a tomogram is produced. However, a laser light source, which emits very short-pulsed light on the order of picosecond pulse, is expensive and is large, and cumbersome handling is required.

Recently, OCT (Optical○Coherence○Tomography) which produces a tomogram of test specimen by the use of low-coherence light has been disclosed in, for example, PCT Japanese Translation Patent Publication No. 6-511312 (U.S. Pat. No. 5,312,501).

Japanese Unexamined Patent Application Publication No. 11-56786 has disclosed in detail an optical scanning probe device which can be used by insertion through an endoscope.

However, as is shown in FIG. 4, etc., in the publication of Japanese Unexamined Patent Application Publication No. 11-56786, since the optical scanning probe device of the prior example is nearly in the shape of a cylinder, it is difficult, for example, to observe at a given distance from the living-organic tissue.

That is, it is possible to observe while the outer surface of the sheath is in contact with the surface of the living-body tissue. However, it is difficult to observe while the outer surface of the sheath is held at a position some distance from the living-body tissue surface larger than that in the aforementioned condition.

In the prior example, specifically designed optical scanning probe devices having different focus positions have been used in accordance with methods for observation and parts to be observed. Consequently, many specifically designed optical scanning probe devices have been required and therefore, a large burden has been born by the user. Furthermore, the management thereof has been cumbersome.

In the OCT device of the prior example, an observation target is radiated with a light beam for performing observation, and relative position relationship between the focus position of this light beam and the observation target is an important parameter for producing a tomogram of the OCT.

Since the beam diameter becomes minimum at the focus position of the light beam, information with the highest resolution can be gained at this part. Therefore, for example, when the focus position is located on the surface of the observation target, detailed information can be gained in the neighborhood of the surface. When the focus position is located inside the observation target, detailed information regarding the deep part can be gained.

In the case where the observation target has an intense light scattering characteristic, when the focus position coincides with the surface of the observation target, an intense light scattering occurs at the observation target surface and, therefore, only reflected light from the surface may be imaged. Consequently, it may be required that the focus position is located intentionally inside the tissue surface, or is located outside in order to observe.

Furthermore, it is important that the light beam is made to enter into the observation target as perpendicularly as possible in order to gain a tomogram with precise information regarding distance.

Japanese Unexamined Patent Application Publication No. 11-56768 has disclosed in detail an optical scanning probe device which can be used by insertion through an endoscope.

In such an optical probe device, since the light beam is made to scan in the circumferential direction in order to produce a circular tomogram centering the probe, when the observation target is located at a distance from the probe as far as possible, a wide range tomogram can be produced compared to that in the observation performed while the observation target is in contact with the probe.

Therefore, the probe, in which the focus position of the light beam has been located away from the probe, has been used, the probe has been positioned at a location some distance from the observation target, and observation has been performed while the aforementioned focus position relationship has been adjusted with the angle of the endoscope and the like.

In the case where tomography observation has been performed using an optical probe and, at the same time, endoscopic therapy has been performed from the same position by the use of endo-therapy products, for example, biopsy forceps, an endoscope having two forceps channels, etc., has been used, the optical probe has been inserted through one channel so as to observe, and an endo-therapy product such as biopsy forceps, has been inserted into the other channel so as to perform therapy aiming at the scanning position of the light beam.

However, regarding an optical probe device of a conventional example which has been inserted through an endoscope as shown in FIG. 4, etc., in the publication of Japanese Unexamined Patent Application Publication No. 11-56768, it has been very difficult to perform stable positioning while fine adjustment among the observation target, light beam focus, entry angle, etc., has been made by endoscope operation in accordance with the observation purpose in the state in which the optical probe device is protruded from the endoscope tip. In addition, it has been attended with significant difficulties to perform biopsy aiming at the scanning position of the light beam by the combination of the endoscope having two forceps channels and the biopsy forceps.

OBJECTS AND SUMMARY OF THE INVENTION

It is an object of the present invention to provide an optical scanning probe device which can perform observation while being positioned at a given distance, or the like, from the living-body tissue which becomes an observation target.

It is another object of the present invention to provide an optical scanning probe device in which the focus position can be set variably.

Other objects include that the positional relationship between the observation target and the optical probe is retained stably and, therefore, operational ease is improved, that the positional relationship between the forceps hole of the endoscope, in which an optical probe is inserted, and the positioning member is adjusted and, therefore, the probe can exhibit intrinsic optical performances, that the light beam is made to enter nearly perpendicularly into the observation target, the optical probe is precisely positioned in order to locate the focus of the light beam at a proper position in accordance with the observation purpose and, therefore, tomogram information with precise information regarding distance can be gained in accordance with the observation purpose, that biopsy is simultaneously performed with ease from the light scanning position at the same time as the tomography observation with the optical probe, that when an endoscope having one forceps channel is used, even if observation and biopsy with the optical probe cannot be performed simultaneously, marking is performed at the part observed and, therefore, biopsy is performed later using this as a landmark, that adjustment of the amount of protrusion of the probe for positioning can be performed with ease, that movement of the optical probe in the direction perpendicular to the longitudinal axis is inhibited and, therefore, the pint position of the light beam can be positioned further precisely, and that adjustment of the amount of protrusion of the optical probe for positioning can be performed with ease and, in addition to this, movement of the optical probe in the direction perpendicular to the longitudinal axis is stopped and, therefore, the pint position of the light beam can be positioned further precisely.

The above and other objects, features and advantages of the invention will become more clearly understood from the following description referring to the accompanying drawings.

An optical scanning probe device for producing an optical tomogram based on reflected light by radiating living body tissue with low-coherence light includes a flexible sheath in which at least the tip side has excellent light transmittance, a light exit & entrance portion which is provided in the aforementioned sheath lumen, which has an optical axis intersecting the aforementioned sheath nearly perpendicularly, and which perform exit and entrance of the light, a housing for holding the aforementioned light exit & entrance portion, a flexible shaft which is joined to the aforementioned housing and which transfers rotation from a driving unit at the rear end portion, and a positioning member which is provided on the periphery of the aforementioned light exit & entrance portion and which adjusts the distance between the aforementioned living body tissue and the aforementioned light exit & entrance portion at a predetermined distance larger than the outer radius of the aforementioned sheath, wherein the focus position of the light exiting from the aforementioned light exit-entrance portion can be adjusted in the neighborhood of the aforementioned predetermined distance by the aforementioned positioning member and, therefore, observation is performed with ease.

BRIEF DESCRIPTION OF THE DRAWINGS

FIG. 1 to FIG. 9 relate to a first embodiment according to the present invention, and FIG. 1 is a block diagram showing the configuration of an optical tomography device provided with the first embodiment, FIG. 2 is a diagram showing an endoscope through which the first embodiment is inserted, FIG. 3 is a sectional view showing the rear end side of an optical probe device according to the first embodiment of the present invention, FIG. 4A and FIG. 4B are a vertical sectional view and a perspective view showing the tip side of an optical probe device, FIG. 7A is a diagram showing an OCT image in the case where a positioning member is included, FIG. 7B is a diagram showing an OCT image in the case of a prior example where no positioning member is included, FIG. 8 is a sectional view showing the tip side portion of an optical probe device according to a modified example, FIG. 9 is a diagram showing a manner in which a modified example is inserted through a channel of an endoscope, FIG. 10 and FIG. 11 relate to a second embodiment according to the present invention, and FIG. 10 is a sectional view showing an optical probe device according to the second embodiment, FIG. 11 is a diagram showing that sheath portions with a blade, which are different in positioning distances, are freely attachable to and detachable from an optical probe body, FIG. 12 and FIG. 13 relate to a third embodiment according to the present invention, FIG. 17 is a sectional view showing an optical probe device according to the seventh embodiment, FIG. 18 is a sectional view showing the enlarged tip side shown in FIG. 17, FIG. 19 to FIG. 21 relate to an eighth embodiment according to the present invention, and FIG. 19 is a sectional view showing an optical probe device according to the eighth embodiment, FIG. 20 is a sectional view showing the enlarged tip side shown in FIG. 19, FIG. 48A is a vertical sectional view showing the configuration of an endoscope tip hood connected to the tip of an endoscope, FIG. 48B is a sectional view of the section indicated by line E—E in FIG. 48A, FIG. 49 is a diagram for explaining an action of an endoscope tip hood, FIG. 68A is a configurational diagram showing the configuration of an endoscope tip hood according to the twenty-third embodiment, FIG. 68B is a front view viewed from the tip side of the endoscope tip hood shown in FIG. 68A, FIG. 69 is a diagram for explaining an action of an endoscope tip hood, FIG. 73A is a vertical sectional view showing the configuration of an endoscope tip hood according to the twenty-fourth embodiment, FIG. 73B is a front view viewed from the tip side shown in FIG. 73A, FIG. 74 is a diagram for explaining an action of an endoscope tip hood.

DETAILED DESCRIPTION OF THE PREFERRED EMBODIMENTS

Embodiments according to the present invention will be described below with reference to the drawings.

(First Embodiment)

The first embodiment according to the present invention will be described with reference to FIG. 1 to FIG. 9.

Figure 1:
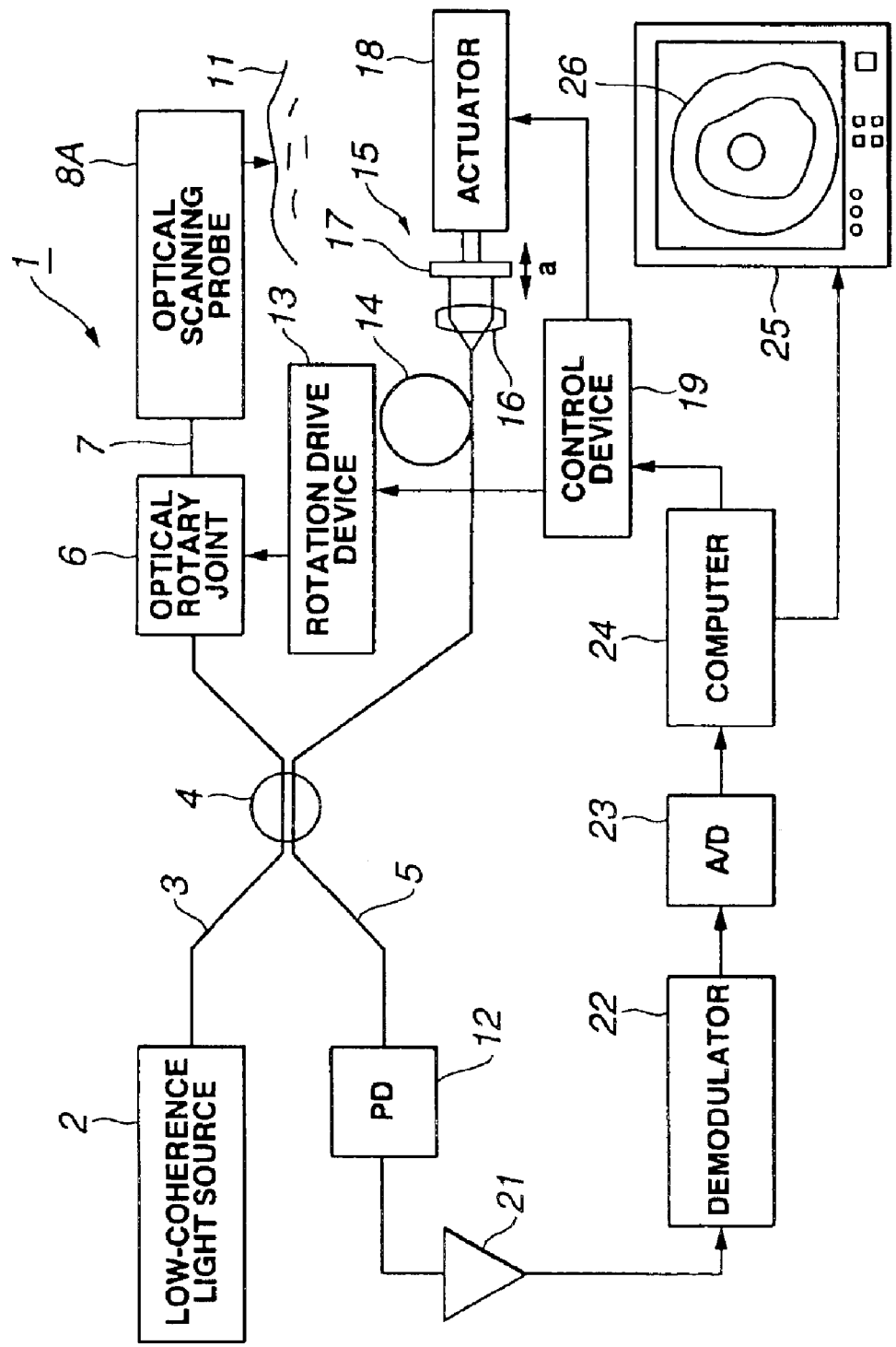

An optical tomography device 1 shown in FIG. 1 includes a low-coherence light source 2, for example, a super luminescent diode (hereafter abbreviated as SLD). This low-coherence light source 2 is provided with characteristics of low-coherence light exhibiting coherence only in a short-distance range in which the wavelength thereof is, for example, 1,300 nm and the coherence length is, for example, on the order of 17 $\mu$m. That is, in the case where this light is divided into, for example, two portions and, thereafter, the two portions are mixed again, when the difference between two optical path lengths from the division point to the mixing point is within the short-distance range on the order of 17 $\mu$m, this light is detected as the light in which interference has occurred, and when the optical path length is larger than that, characteristics shows no occurrence of interference.

The light from the low-coherence light source 2 is made to enter into one end of the first single mode fiber 3, and is transmitted to the other end face (tip face) side.

This first single mode fiber 3 is optically coupled to the second single mode fiber 5 at an optical coupler portion 4 on its way. Therefore, the light is divided into two portions in this optical coupler portion 4, and are transmitted.

At the tip side (farther than is the optical coupler portion 4) of the first single mode fiber 3, an optical rotary joint 6 which perform coupling capable of transmitting light between a non-rotary portion and a rotary portion is interposed. The light from the low-coherence light source 2 is transmitted (guided) to the fourth single mode fiber 9 through the third single mode fiber 7 in the optical rotary joint 6. The fourth single mode fiber 9 is inserted through an optical probe device (hereafter abbreviated as optical probe) 8A according to the first embodiment and is driven to rotate. Hereafter, the first to fourth single mode fibers are abbreviated briefly as optical fibers.

The transmitted light is radiated to living-body tissue 11 side from the tip side of the optical probe 8A while being made to scan. A part of the reflected light which has been, for example, scattered on the surface or in the inside of the living-body tissue 11 side is captured, and is returned to the first optical fiber 3 side through the optical paths in reverse order. A part thereof is transmitted to the second optical fiber 5 side by the optical coupler portion 4, and is made to enter into a photodiode 12 as an example of photodetectors from one side of the second optical fiber 5. The rotor side of the optical rotary joint 6 is driven to rotate by a rotation drive device 13.

An optical loop portion 14 is provided in the way to the tip side, which is farther than is the optical coupler portion 4, of the second single mode fiber 5, and at the tip thereof, an optical path length-adjustable mechanism 15 is provided.

That is, a lens 16 and a mirror 17 are placed facing the tip face of the second optical fiber 5, and this mirror 17 can change an optical path length as indicated by an arrow a with an actuator 18. The light reflected by the mirror 17 is mixed with the light leaked from the first optical fiber 3 side in the optical coupler portion 4, and both are received by the photodiode 12. The actuator 18 and the rotation drive device 13 are controlled by a control device 19.

The loop portion 14 is adjusted to have a length nearly equivalent to the optical path length based on the fourth optical fiber 9 on the optical probe 8A side, etc. The optical path length which is started from the tip face of the second optical fiber 5, is reflected by the mirror 17, and is returned to the tip face of the second optical fiber can be made equivalent to the optical path length which is started from the tip face of the fourth optical fiber 9, is radiated to the living-body tissue 11 through a microprism, etc., described below, is reflected in the inside of the living-body tissue 11, etc., and is returned to the tip face of the fourth optical fiber 9.

It becomes possible by changing the position of the mirror 17 in the optical path length-adjustable mechanism 15 in the reference light side in order to change the optical path length thereof that the reflected light from the position at a depth in the living-body tissue 11 having a value equivalent to this optical path length is made to cause interference, and reflected light from the positions at other depths are made to cause no interference.

A signal photoelectrically converted in the aforementioned photodiode 12 is amplified by an amplifier 21 and, thereafter, is input into a demodulator 22. In the demodulator 22, demodulation treatment is performed in order that only the part of the signal of the light having interfered is extracted. The output thereof is input into a computer 24 via an A/D converter 23. In this computer 24, image data corresponding to a tomogram are produced, and are output to a monitor 25 so as to display an OCT image 26 on the display surface thereof.

The computer 24 is connected to the control device 19. Via the control device 19, the computer 24 performs the control of change in optical path length of the reference light via the actuator 18, and performs the control of the light scanning direction based on the rotation by the rotation drive device 13.

Figure 2:
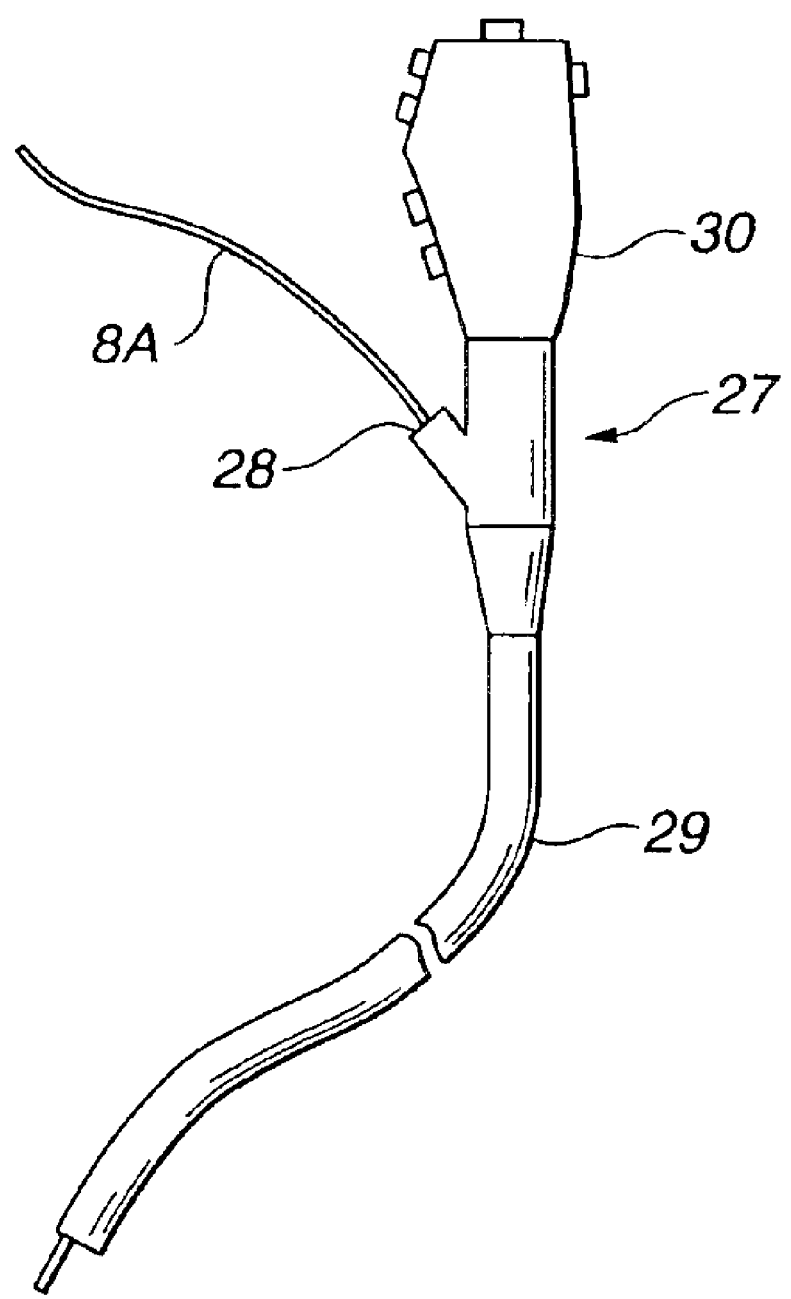

The optical probe 8A according to the first embodiment passes through a forceps insertion hole 28 of the endoscope 27 and a channel 28a for forceps insertion (refer to FIG. 5A), and the tip side of the optical probe 8A can be protruded from the tip opening thereof, as shown in FIG. 2.

This optical probe 27 includes a slender insertion portion 29 in order to be inserted into a body cavity with ease, and a wide control portion 30 is provided at the rear end of the insertion portion 29. The forceps insertion hole 28 is provided in the neighborhood of the front end of this insertion portion 30, and the forceps insertion hole 28 is communicated with the channel 28a for forceps insertion in the inside thereof.

A light guide 28b (refer to FIGS. 5A and 5B) is inserted through the insertion portion 29. The entrance end of this light guide 28b is connected to the light source device, and illumination light is transmitted and is made to exit from a illumination window provided at the tip of the insertion portion 29 so as to illuminate an affected area, etc. An observation window is provided adjacently to the illumination window, and an objective optical system is fitted to the observation window in order to observe the illuminated affected area, etc., with the optical system.

Under observation with the optical observation system at the tip portion of the endoscope 27, the living-body tissue 11 side of the noted part, for example, an affected area, is radiated with low-coherence light by the optical probe 8A, tomogram data of the inside of the living-body tissue 11 are gained, and the OCT image 26 can be displayed on the display surface of the monitor 25.

The configuration of the optical probe 8A according to the first embodiment will be described below with reference to FIG. 3, FIG. 4A, and FIG. 4B.

Figure 3:
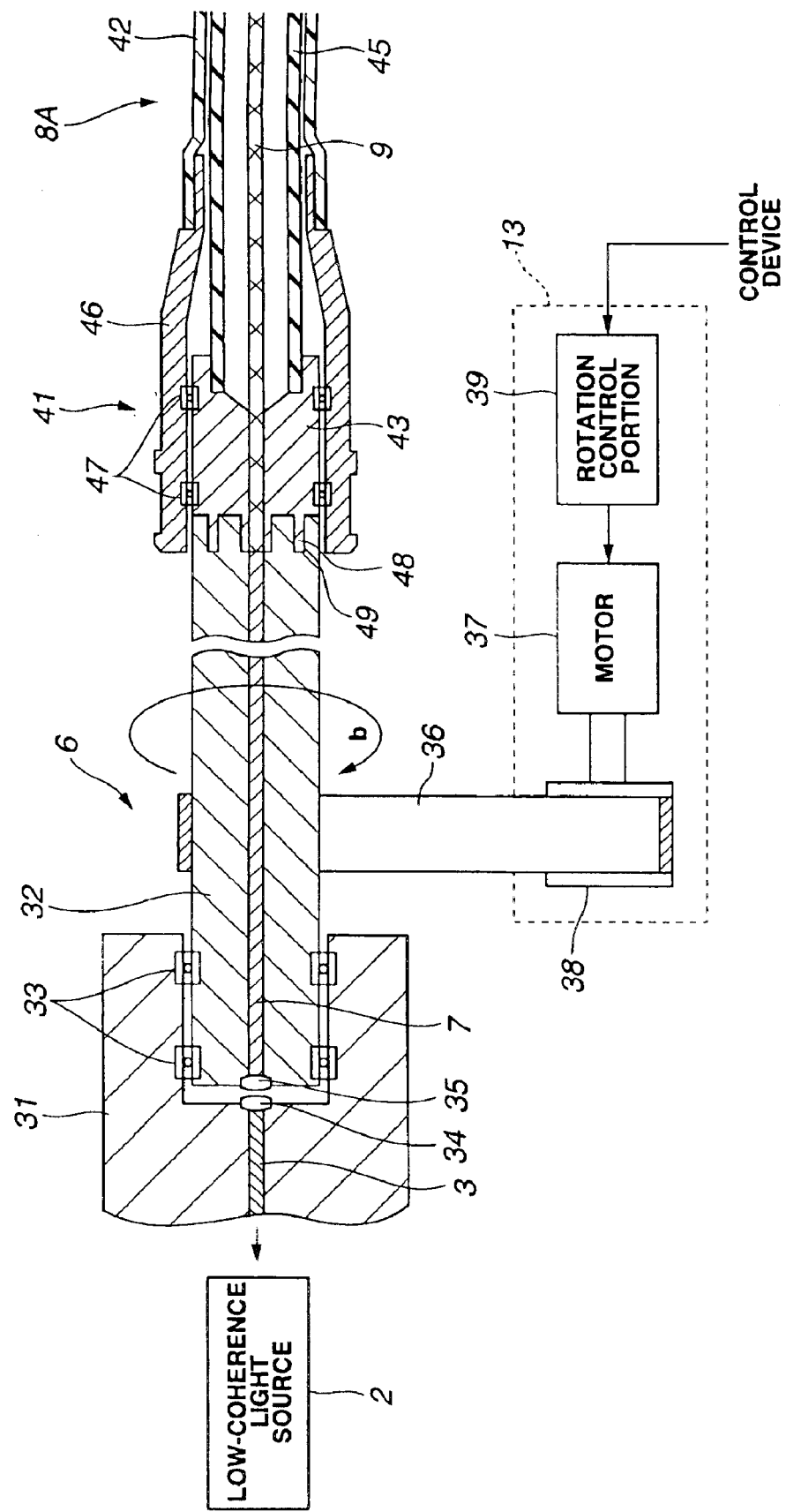

The tip side of the first optical fiber 3 is optically coupled to the fourth optical fiber 9 which is inserted through the optical probe 8A via the third optical fiber 7 in the optical rotary joint 6 shown in FIG. 3.

A rotor receiver 31 is provided at the tip of the first optical fiber 3, a rotor 32 is fitted into the concave portion of the rotor receiver 31, and the rotor 32 is supported by bearings 33 interposed at two places therebetween, while the rotor can freely rotate (relative to the rotor receiver 31 not rotated).

The first optical fiber 3 and the third optical fiber 7 are inserted along the center of the rotor receiver 31 and the rotor 32, respectively, convex lenses 34 and 35 are placed at the end faces facing the optical fibers 3 and 7, respectively, and, therefore, transmission of the light between the optical fiber 3 not rotated and the optical fiber 7 rotated can be performed effectively.

The rotor 32 is joined to a pulley 38 of a motor 37 constituting the rotation drive device 13 via, for example, a belt 36. The rotor 32 is rotated as indicated by an arrow b due to rotation of the motor 37 and, therefore, the third optical fiber 7 is rotated concurrently. The motor 37 is driven to rotate at a constant rate by a motor drive signal from the rotation control portion 39.

A connector portion 41 provided at the rear end of the optical probe 8A is connected to the tip of the rotor 32.

As shown in FIG. 4A and FIG. 4B, regarding the optical probe 8A, the fourth optical fiber 9 is placed along the center axis of a slender sheath 42 which has pliability (flexibility) and the shape of a circular tube and which becomes a sheath tube, the rear end and the tip of the fourth optical fiber 9 are fixed to a connecter main body 43 and a housing 44, respectively, and the fourth optical fiber 9 is covered with a flexible shaft 45 as a hollow and flexible torque transfer member. The inner diameter of this flexible shaft 45 is slightly larger than the outer diameter of the fourth optical fiber 9.

The fourth optical fiber 9 has, for example, a core diameter on the order of 9 $\mu$m.

The sheath 42 is formed from a tube made of, for example, fluororesin having excellent light transmittance with respect to at least the wavelength of the light emitted from the low-coherence light source 2. The part having excellent light transmittance may be only the tip side of the sheath 42, in more detail, only a circumferential ring portion facing the portion where the light exits from a prism 52 and enters into the prism 52.

The flexible shaft 45 has flexibility and a function of effectively transferring the rotation applied to one end (rear end) to the other end (tip) by using a double or triple thickness of densely wound coil. The rear end and the tip of this flexible shaft 45 are fixed to the connector main body 43 and the housing 44.

A cylindrical connector cover 46 forming the connector portion 41 is fixed at the rear end of the sheath 42, and the cylindrical column-shaped connector main body 43 is supported inside the connector cover 46 with bearings 47 provided at two places therebetween, while the connector main body 43 is freely rotated. The rear end of the fourth optical fiber 9 is inserted into a hole provided at the center axis of the connector main body 43, and is adhered with an adhesive, etc.

Convex portions 48 are provided at the rear end face of the connector main body 43. On the other hand, concave portions 49 which are fitted into these convex portions 48 are provided at the tip face of the rotor 32, and these are fitted to each other. When the rotor 32 is rotated under the condition in which both are butted, the connector main body 43 is also rotated. This torque is imparted to the rear end of the flexible shaft 45, is transferred with the flexible shaft 45 to the tip thereof, and the housing 44 mounted at the tip thereof is rotated.

As shown in FIG. 4A, the tip of the fourth optical fiber 9 is inserted into a hole provided at the center axis of the housing 44, and is adhered with an adhesive, etc. A GRIN lens 51 which faces the tip face of the fourth optical fiber 9 and which condenses light exiting from the tip of the fourth optical fiber 9 on a predetermined position is fixed to the inner wall of the housing 44. The microprism (hereafter, briefly prism) 52 which changes the light guide direction from the longitudinal direction of the sheath 42 to the direction perpendicular thereto by total reflection is fixed to the tip face of the GRIN lens 51 with an adhesive, etc.

An opening is provided at the part, from which the light reflected by the prism 52 in the housing 44 exits and which becomes an entrance portion of the light returning from the living-body tissue 11 side as well. The light, which is guided by the fourth optical fiber 9 and which is made to exit from the tip face, is condensed with the GRIN lens 51. The exit light (due to low-coherence light) condensed is reflected by the prism 52 in the normal direction, is passed the opening of the housing 44, is transmitted through the transparent sheath 42 and, therefore, can be made to exit to the outside. The resulting light can be condensed to have a light flux diameter of, for example, 10 μm to 30 μm on the condensing point at a predetermined distance of L1 from the outer surface of the sheath 42.

An antireflective film may be provided on the rear face of the GRIN lens 51 and the front face of the prism 52 by, for example, applying a coating of an antireflective member in order to reduce generation of the reflected light.

In the present embodiment, a blade member 54 which is formed from an elastic member, for example, silicone rubber, and which is provided with a blade 54a, as also shown in FIG. 4B, is provided at the tip of the sheath 42 extended forward of the housing 44 via a connection member 53.

A connection member 53 is provided with tapers for preventing drop out at both ends, one end thereof is press-fitted into the tip of the sheath 42, the other end is press-fitted into the concave portion of the base end of the blade member 54, the tip of the sheath and the base end of the blade member 54 having the same outer diameter are butted, and regarding the butt portion, the blade member 54 is connected and fixed watertight to the tip of the sheath 42 with a string binding adhesion portion 55 (by binding with string and by adhesion).

A plurality of blades 54a (six blades in FIG. 4B) are formed as protrusions for positioning at the tip of the blade member 54. The protrusions are made by notching a disk-shaped member, and are protruded in the direction of the radius. Each blade 54a has a length to protrude from the outer surface of the sheath 42 by a distance of L2, as shown in FIG. 4A and, therefore, a positioning unit is formed. The end portion of each blade 54a is made to contact with the surface of the living-body tissue 11 in order that the tip side of the optical probe 8A is positioned and kept at a predetermined interval from the surface of the living-body tissue 11.

Figure 6A:
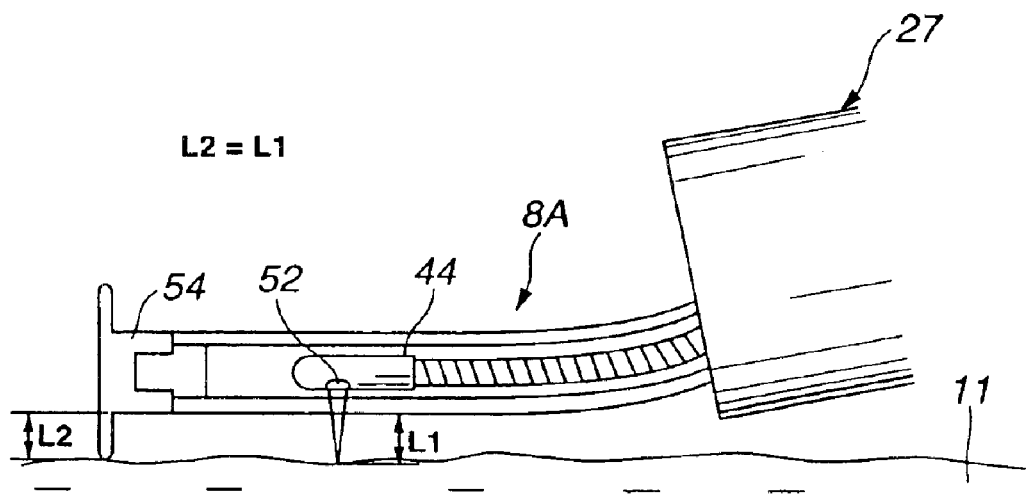
FIG. 6A to FIG. 6C are diagrams, each showing a manner of observation by protrusion from a channel of an endoscope.

That is, the tip side of the optical probe 8A is positioned by making the end portion of the blades 54a, which are protruded, contact with the living body surface, as shown in FIG. 6A, and, therefore, observation can be performed (an OCT image can be produced).

In the present embodiment, since the positioning unit is provided as described above, focus can be achieved at a distance of L1 from the outer surface of the sheath 42 larger than that in the prior example. Consequently, the effective observation range can be enlarged (as described below with reference to FIG. 7A and FIG. 7B).

Figure 5A:
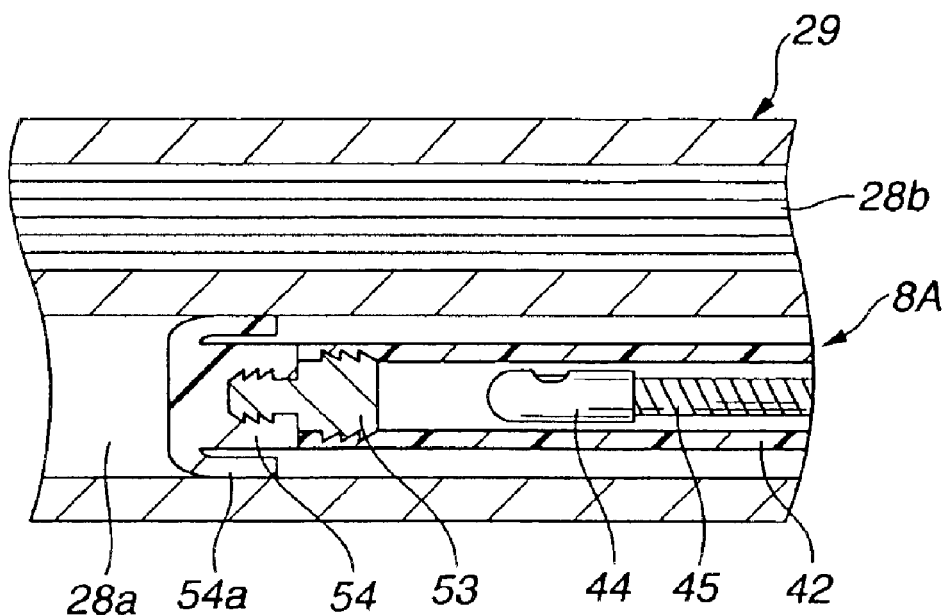
FIG. 5A and FIG. 5B are diagrams showing the tip side of an optical probe device during insertion into a channel of an endoscope and during extraction, respectively.

Although the positioning unit may be only a disk-shaped member having no notch formed, in the present embodiment, a plurality of blades 54a are formed by notching the disk-shaped member in order to be inserted through the channel 28a shown in FIG. 5A with ease.

Furthermore, each blade 54a is bended at the base end side in order to be inserted through the channel 28a with ease.

As shown in FIG. 4B, the end portion of each blade 54a is rounded (made to be a curved surface) and, therefore, soft contact with the living-body can be achieved.

As described above, since blades 54a are formed by notching the disk-shaped member formed from flexible silicone rubber, etc., the blade member 54 can be inserted through the channel 28a in the insertion portion 29 from the forceps insertion hole 28 of the endoscope 27 by bending the base ends of the blades 54a as shown in FIG. 5A.

Figure 5B:
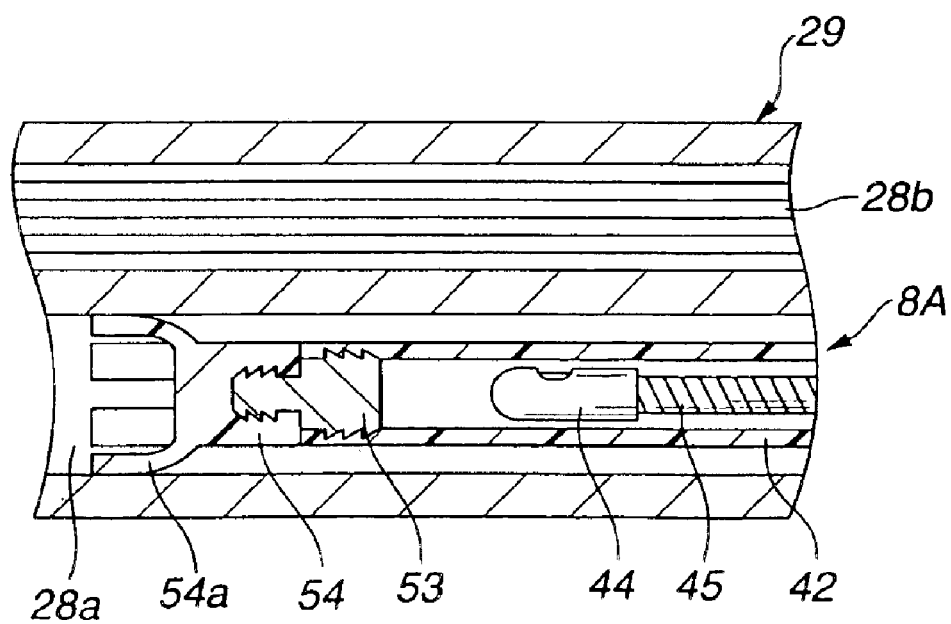

FIG. 5A shows the optical probe 8A during insertion, and FIG. 5B shows that during extraction. In FIG. 5A and FIG. 5B, reference numeral 28b denotes the light guide.

Figure 6B:
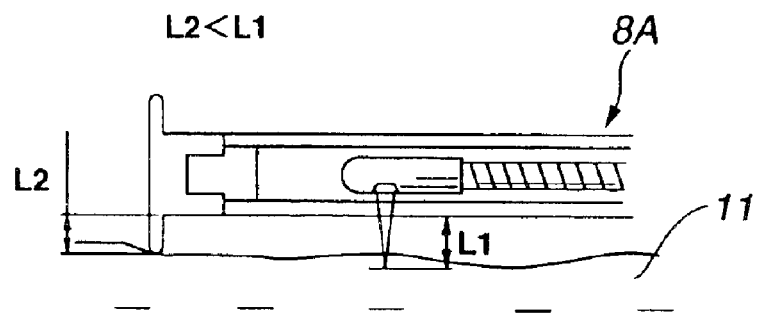
Figure 6C:
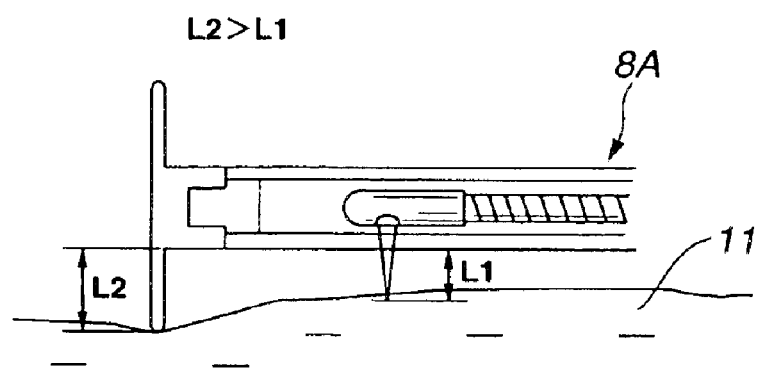

The manner of observation of the living-body tissue 11 with the optical probe 8A having such a configuration is shown in FIG. 6A to FIG. 6C.

FIG. 6A shows the case where the distance L2 (positioning distance from the outer surface of the sheath 42) of the blade 54a due to the blade member 54 is adjusted to be in the same condition as is the distance L1. The tip side of the optical probe 8A inserted through the channel 28a of the endoscope 27 is protruded from the channel tip opening in order that the blade 54a is made to contact with the surface of the living-body tissue 11, the low-coherence light is made to exit to the living-body tissue 11 and, in addition, the scattered light therefrom is captured so as to display an OCT image on the monitor 25. In this case, the light made to exit from the prism 52 (from the opening of the housing 44) comes into a focus on nearly the same position as the outer end portion of the blade 54a.

Consequently, since the light comes into a focus on the surface of the living-body tissue 11, the surface and its surroundings of the living-body tissue 11 can be imaged at high resolution.

Furthermore, as shown in FIG. 6B, observation of the living-body tissue 11 may be performed with the one in which the distance L2 (positioning distance from the outer surface of the sheath 42) of the blade 54a is adjusted to be smaller than the distance L1.

In this case, since the light comes into a focus on a position inner than the surface of the living-body tissue 11, the inside of the surface of the living-body tissue 11 can be imaged at high resolution.

In the case where observation of the living-body tissue is required regarding organs, etc., in which an observation target part and its surroundings are very soft, it is possible that the one, in which the distance L2 (positioning distance from the outer surface of the sheath 42) of the blade 54a is adjusted to be larger than the distance L1, is made to contact with the part adjacent to the observation target part, positioning is performed and, therefore, observation of the living-body tissue 11 is performed, as shown in FIG. 6C.

In this case, the part, with which the outer end portion of the blade 54a is made to contact, is very soft and, therefore, is deformed into the shape of a concave. However, the part adjacent thereto, which is to be observed by radiation of the light, becomes in a condition in which it is hardly deformed and, therefore, an OCT image can be produced while the part is in a natural condition without application of any load.

FIG. 7A shows an OCT image region achieved according to the present embodiment. In this case, the part of the living-body tissue, which is within the ring-shaped effective focus range indicated by dotted lines and which is in the neighborhood of the distance L1 outside the optical probe 8A, that is, the diagonally shaded part, becomes an OCT image in which the effective image observation range can be observed clearly.

On the other hand, in the case of the prior example where no positioning unit is included, as shown in FIG. 7B, a small diameter of ring-shaped effective focus range is formed immediately outside the optical probe. Since the radius of the ring is smaller than that in the case of FIG. 7A, the effective observation range which can be clearly observed becomes a narrow range in practice.

As described above, according to the present embodiment, since the positioning unit is provided, and observation can be performed while the distance L1 from the outer surface of the sheath 42 to the living-body tissue 11 is kept to be a spaced distance, the distance L1 can be increased compared to the case of the prior example (in the prior example, since it is assumed that the outer surface of the sheath is made to contact with the living-body tissue 11, the light comes into a focus on a position immediately outside the sheath 42). Therefore, since a wide range region can be stably and clearly observed at one time, it is possible to perform inspection of the presence or absence of lesion with ease.

Figure 8:
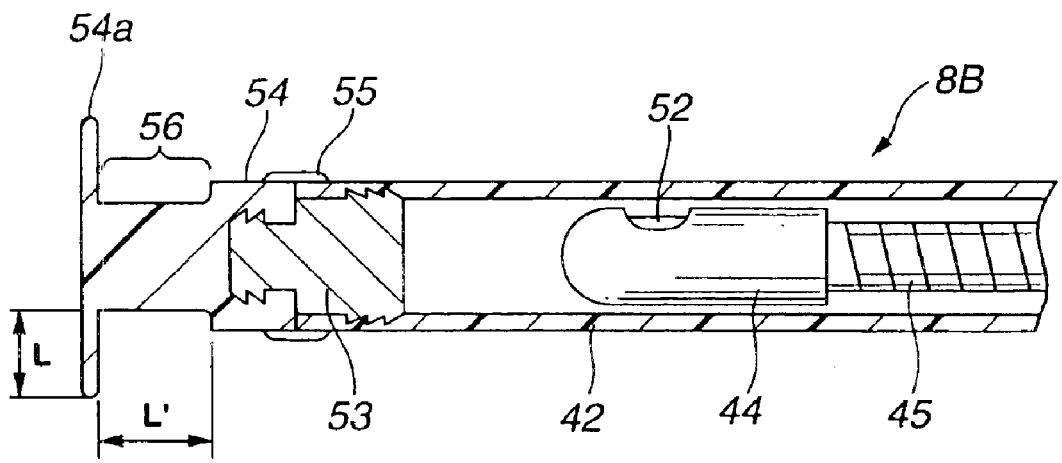

FIG. 8 shows a tip side of the optical probe 8B of the modified example.

In the present modified example, a storage portion or reduced diameter step-shaped portion 56 for storing the blade 54a by bending is provided at the part of the outer perimeter of the tip side adjacent to the blade 54a in the blade member 54.

That is, the length L' of the reduced diameter part in the step-shaped portion 56 is specified to be larger than the length L (herein, the length of protrusion from the step-shaped portion 56 in the direction toward the outside of the radius) of the blade 54a (L'>L).

In this case, it is desirable that the depth of the step-shaped portion 56 is specified to be equivalent to or more than the thickness of the blade 54a. Other configuration is similar to that in the first embodiment.

Figure 9:
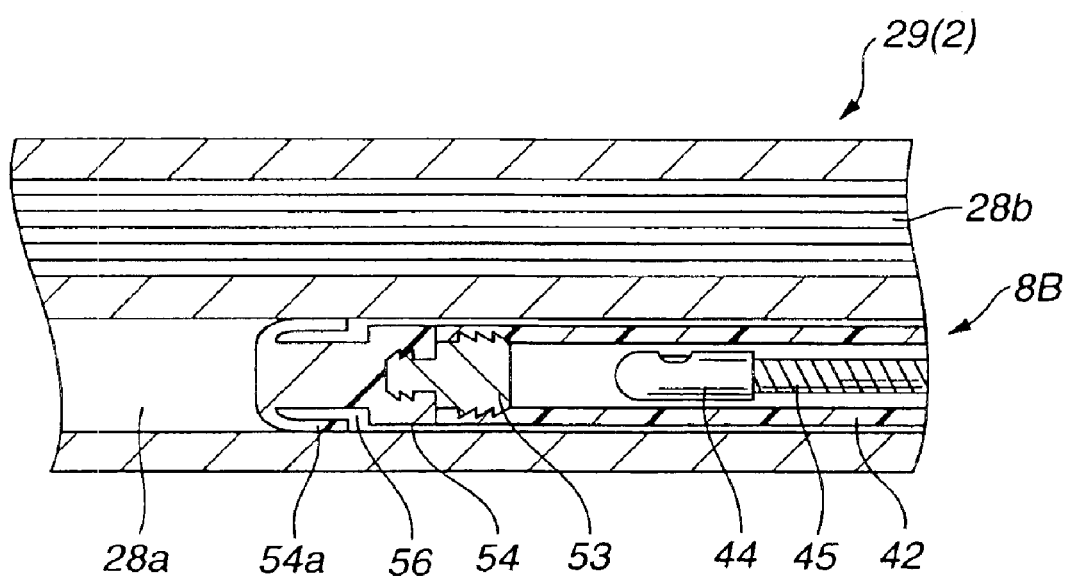

According to such a configuration, as shown in FIG. 9, since the part of the blade 54a bended can be stored in the step-shaped portion 56 during insertion into the channel 28a in the insertion portion 29 of the endoscope 2, even when the channel 28a has a small diameter, it becomes possible to insert the optical probe 8B.

Therefore, according to the present modified example, effects similar to those in the first embodiment can be exhibited and, in addition to this, since the diameter can be reduced during insertion, there is an effect that it is possible to use in the case of an endoscope (channel) having a smaller diameter.

(Second Embodiment)

The second embodiment according to the present invention will be described with reference to FIG. 10 and FIG. 11.

An optical probe 8C according to the present embodiment includes an optical probe main body 58 as shown in FIG. 11 and a sheath portion with blade 59A freely attachable to and detachable from the optical probe main body 58.

This optical probe 8C has the structure of the optical probe 8A according to the first embodiment, wherein an inner sheath 60 which covers the flexible shaft 45, housing 44, etc., and which has pliability and light transmittance is provided inside the sheath 42, and at the base end of the inner sheath 60, a connection portion 61 is provided in order that the base end of the sheath 42 can be freely attached thereto and detached therefrom. The tip of the inner sheath 60 is blocked watertight by, for example, a half-round tip cap 62.

An internal thread portion (constituting the connection portion 61) is provided at the base end of the sheath (the outer sheath in this case) 42 provided with the blade member 54 at the tip with a connection portion 53 therebetween and, therefore, the sheath portion with blade 59A is formed. This sheath portion with blade 59A can be freely attached to and detached from the optical probe main body 58 in which an external thread portion 61a is provided on the outer perimeter of the base end of the inner sheath 60 covering the flexible shaft 45, housing 44, etc.

The positioning distance L2 of the blade 54a of the blade member 54 in FIG. 10 is adjusted to be nearly the same value as the focus distance L1 from the outer surface of the sheath 42 due to the optical probe main body 58 (L2=L1).

In the present embodiment, the sheath portion with blade 59A shown in FIG. 10, and a sheath portion with blade 59B and a sheath portion with blade 59C shown in FIG. 11, which are different in length of the blade 54a, are included. Consequently, a proper sheath portion with blade 59I (I=A, B, or C) is fitted to the optical probe main body 58 in accordance with an observation part, etc., and, therefore, can be used as the optical probe 8C.

Regarding the sheath portion with blade 59B shown in FIG. 11, the positioning distance L2 of the blade 54a is smaller than the focus distance L1 from the outer surface of the sheath 42 due to the optical probe main body 58 (L2<L1), and regarding the sheath portion with blade 59C, the positioning distance L2 of the blade 54a is larger than the focus distance L1 from the outer surface of the sheath 42 due to the optical probe main body 58 (L2>L1).

Therefore, as is described in the first embodiment with reference to, for example, FIG. 6A to FIG. 6C, it is possible to respond in accordance with an observation parts, uses, etc., by only exchanging the sheath portion with blade 59I side to be used.

Consequently, the present embodiment exhibits effects similar to those in the first embodiment and, in addition, since it is possible to respond in accordance with various uses and parts, by exchanging the sheath portion with blade, a plurality of optical probes need not be prepared and, therefore, outlay of the user can be reduced.

(Third Embodiment)

The third embodiment according to the present invention will be described with reference to FIG. 12 and FIG. 13.

Regarding an optical probe 8D according to the present embodiment, in the first embodiment, the connection member 53 is fixed watertight to the tip of the sheath 42 on this connection member 53, an external thread portion 64 is provided in order that the blade member 54 side provided with the blade 54a can be freely attached and detached so as to form an optical probe main body 65, and blade unit 67A provided with a internal thread member 66, which can be freely attached to and detached from the external thread portion 64 by thread engagement, is formed on the blade member 54 side.

In the present embodiment, the blade 54a is formed at the rear end portion of the blade member 54. In the present embodiment, a protrusion portion (or small diameter portion) 68, which is protruded from the outer diameter of the internal thread member 66 toward inside the radius, is provided stepwise at the rear end of the blade member 54. When the blade unit 67A is screwed into the external thread portion 64 at the tip of the optical probe main body 65, this protrusion portion 68 is pressed by the external thread portion 64 and the connection member 53 to cause elastic deformation and, therefore, the blade unit 67A can be fitted watertight to the tip of the optical probe main body 65.

Figure 12:
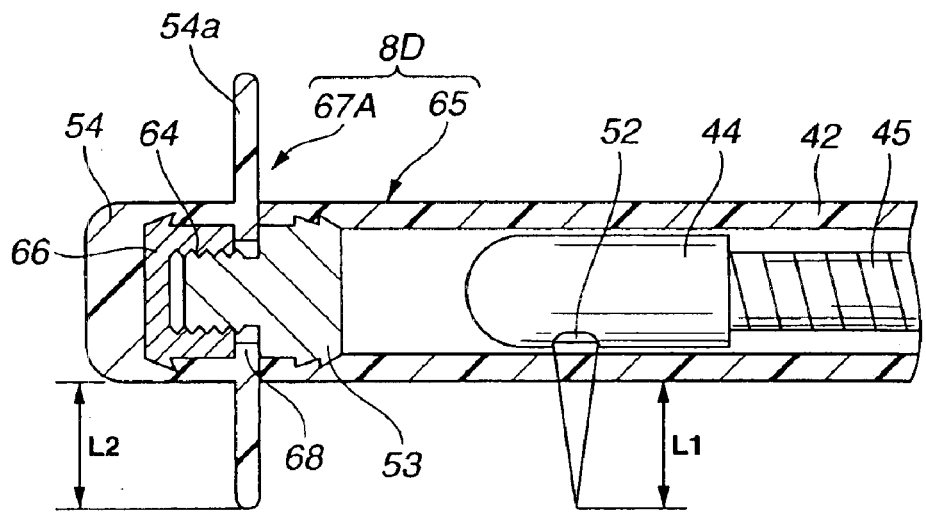
FIG. 12 is a sectional view showing the tip side of an optical probe device according to the third embodiment.

In FIG. 12, the positioning distance L2 of the blade 54a of the blade member 54 is adjusted to be nearly the same value as the focus distance L1 from the outer surface of the sheath 42 due to the optical probe main body 65 (L2=L1).

Figure 13:
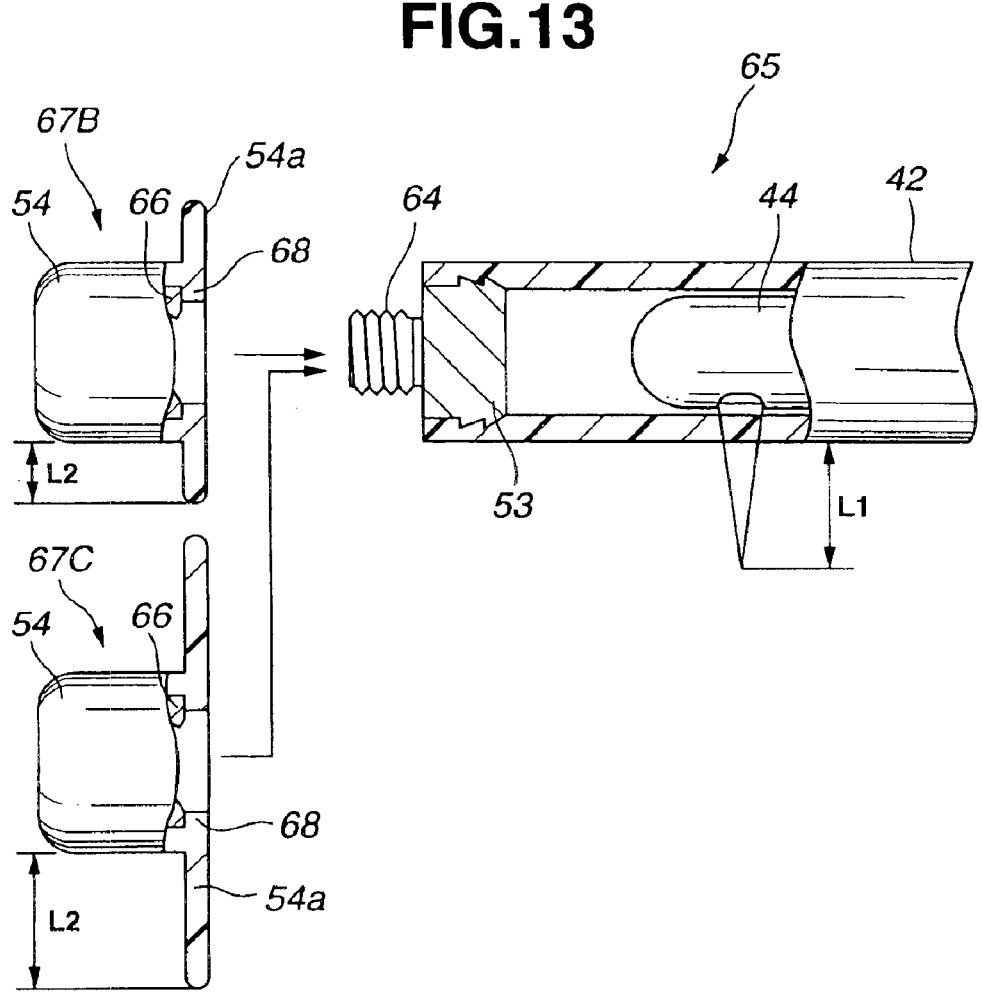
FIG. 13 is a diagram showing that blade units different in positioning distances are freely attachable to and detachable from an optical probe body.

In the present embodiment, the blade unit 67A shown in FIG. 12, and a blade unit 67B and a blade unit 67C shown in FIG. 13, which are different in length of the blade 54a, are included. Consequently, a proper blade unit 67I (I=A, B, or C) is fitted to the optical probe main body 65 in accordance with an observation part, etc., and, therefore, can be used as the optical probe 8D.

Regarding the blade unit 67B shown in FIG. 13, the positioning distance L2 of the blade 54a is smaller than the focus distance L1 from the outer surface of the sheath 42 due to the optical probe main body 65 (L2<L1), and regarding the blade unit 67C, the positioning distance L2 of the blade 54a is larger than the focus distance L1 from the outer surface of the sheath 42 due to the optical probe main body 65 (L2>L1).

Therefore, as is described in the first embodiment with reference to, for example, FIG. 6A to FIG. 6C, it is possible to respond in accordance with observation parts, uses, etc., by only changing the blade unit 67I side to be used. Furthermore, since the distance in the probe longitudinal direction between the blade 54a and the light exit position can be reduced compared to those in the first and second embodiments, positioning in the body cavity is performed with ease.

The present embodiment exhibits effects similar to those in the second embodiment and, in addition, since exchange of the blade part is performed with ease, operating ease for the operator is improved compared to that in the second embodiment.

Since it is not necessary to have a double-sheath structure, optical loss-return loss is reduced, and S/N is improved compared to those in the second embodiment.

When the blade 54a is deteriorated, it is not necessary to exchange on a sheath basis. Since it is essential only that the blade unit 67I is exchanged, cost bearing by the user can be reduced.

Since the interval in the probe longitudinal direction between the blade 54a and the light exit position can be reduced, and positioning in the body cavity is performed with ease, operating ease for the operator is improved.

(Fourth Embodiment)

Figure 14:
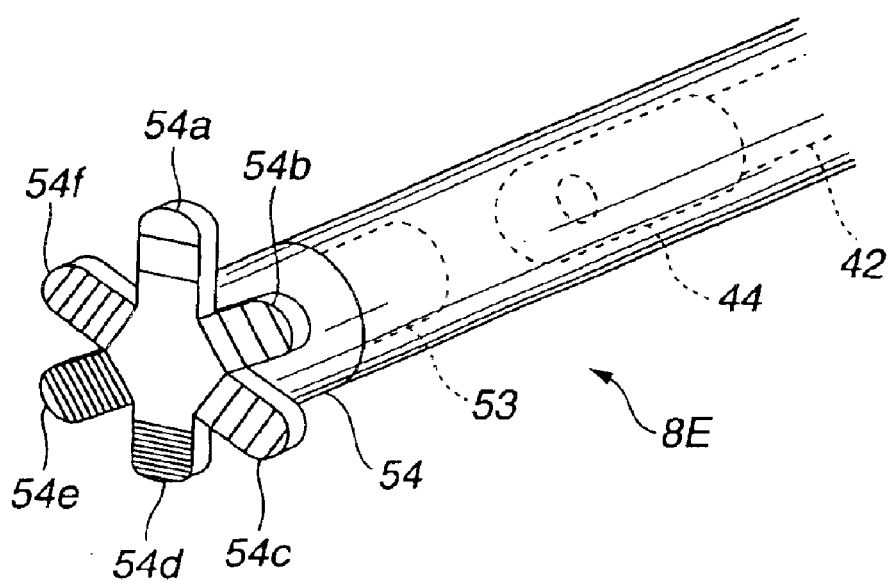
FIG. 14 is a perspective view showing the tip side of an optical probe device according to the fourth embodiment of the present invention.

The fourth embodiment according to the present invention will be described with reference to FIG. 14. FIG. 14 shows an optical probe 8E according to the fourth embodiment. Regarding this optical probe 8E, in the optical probe 8A according to the first embodiment, the lengths of a plurality of blades 54a provided at the tip of the blade member 54 are not equalized, blades 54j (j=a, b, . . . ) are made to have lengths which vary from blade to blade by a small degree, and, for example, colors of the blades 54j are changed in accordance with the length in order to be distinguished with ease. Others are the same as those in the configuration of the first embodiment.

According to such a configuration, since a plurality of blades 54j having different lengths are provided, by changing the blade 54j to be contacted with a living body during observation of the living body, it becomes possible to choose a pint position in accordance with uses and parts during observation.

Since, for example, the color is changed in accordance with the length of the blade 54j, it is possible to distinguish what length of blade 54j is in contact with the living body based on the color of the blade 54j under endoscope observation. In addition to change of the color, for example, a mark on the surface, pattern, etc., may be changed in order to distinguish with ease, and information of length may be added.

The aforementioned plurality of blades 54j having different lengths may be used in the configuration of the second embodiment, be used in the configuration of the third embodiment and, furthermore, be applied to embodiments described below.

The present embodiment has the following effects.

Since the length of the blade in contact with the living body can be changed during inspection, for example, when the noted part is out of focus, by changing the blade 54j in contact with the living-body tissue 11, an image centering on the part can be produced with ease. That is, an optimum image can be produced as circumstances demand during the use for observation (without the need for operation of changing to an optical probe having a different positioning distance, etc.) and, therefore, a function of inspecting (screening) lesion can be performed smoothly in a short time.

(Fifth Embodiment)

Figure 15:
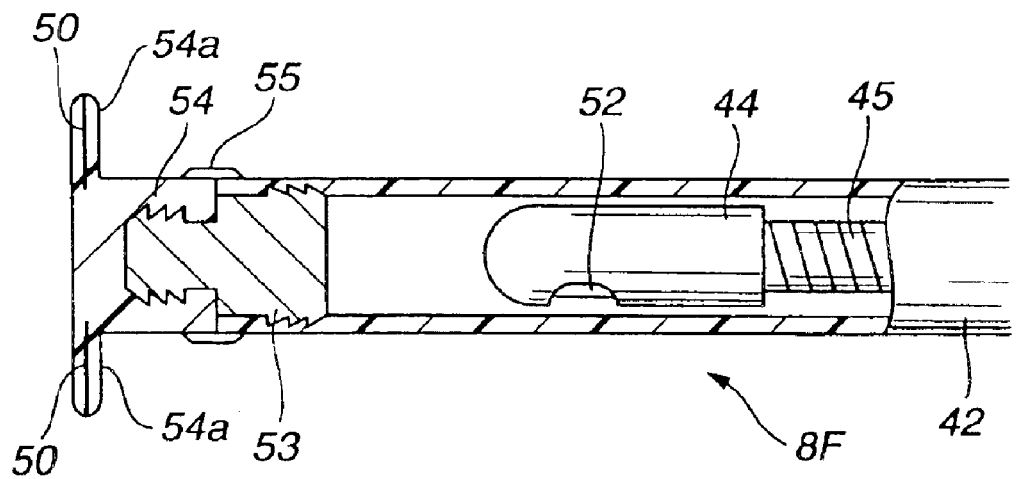
FIG. 15 is a sectional view showing the tip side of an optical probe device according to the fifth embodiment of the present invention.

The fifth embodiment according to the present invention will be described with reference to FIG. 15. FIG. 15 shows the tip side of an optical probe 8F according to the fifth embodiment.

Regarding the optical probe 8F shown in FIG. 15, in the optical probe 8A shown in FIG. 4A, etc., according to the first embodiment, slender reinforcing members 50, for example, metals or plastics, are contained in the inside of the blade 54*a* in the blade member 54. Others are similar to those in the configuration of the first embodiment. The same constituents are indicated by the same reference numerals and explanations thereof are omitted.

Next, actions of the present embodiment will be described. In the present embodiment, since the blade 54*a* becomes unlikely to deform elastically due to the reinforcing member 50, deformation does not occur with ease even when the blade is pressed somewhat strongly against the living-body tissue and, therefore, a function of positioning can be improved. Other actions are similar to those in the first embodiment.

The reinforcing member 50 may be contained in the blade 54*a* as shown in FIG. 15, or be adhered to for example, the surface of the blade 54*a*.

The present embodiment has the following effects.

Effects similar to those in the first embodiment are exhibited and, in addition, since the blade 54*a* is unlikely to deform even when pressed somewhat strongly against the living-body tissue, positioning can be performed with further reliability and operating ease for the operator is further improved.

(Sixth Embodiment)

The sixth embodiment according to the present invention will be described with reference to FIG. 16A and FIG. 16B.

Figure 16A:
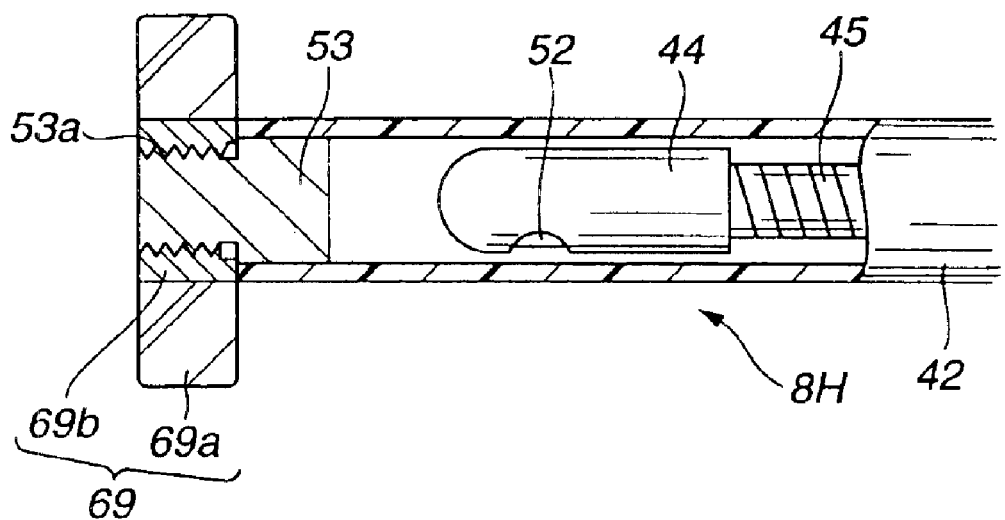
FIG. 16A and FIG. 16B are diagrams showing a cross section and external appearance, respectively, of the tip side of an optical probe device according to the sixth embodiment of the present invention, FIG. 17 and FIG. 18 relate to a seventh embodiment according to the present invention.
Figure 16B:
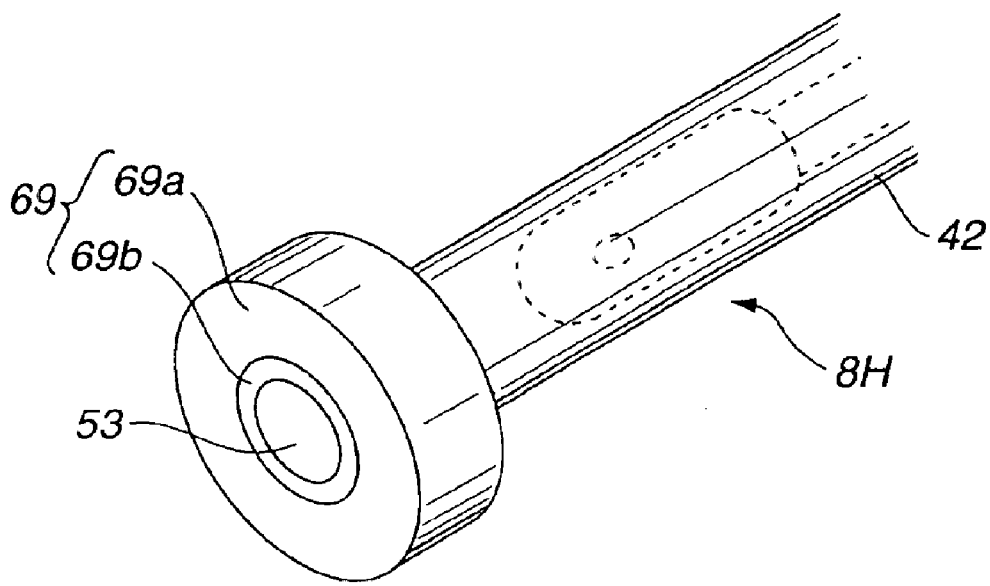

As shown in FIG. 16A and FIG. 16B, in an optical probe 8H according to the present embodiment, the tip opening of the sheath 42 is sealed watertight with the connection member 53 provided with the external thread member 53*a* on the outer perimeter of the tip, and a tip spacer 69 is screwed into the external thread portion 53*a* and, therefore, is attachable and detachable.

This tip spacer 69 is composed of an annular ring 69*a*, which has an outer diameter larger than the sheath 42 and which has a function of positioning, and a ring thread 69*b*, which is fixed to the inner perimeter of this ring 69*a* and in which internal thread portion is formed on the surface of the inner perimeter. Others are similar to those in the first embodiment.

Next, actions of the present embodiment will be described. When the tip spacer 69 is used as a positioning unit for keeping a given distance from the living-body tissue, the positioning unit is not deformed on all occasions and functions in order to ensure stable positioning.

The usage attended with insertion into the endoscope may follow the description below. The optical probe 8H is inserted into the channel of the endoscope at the condition in which the tip spacer 69 is detached. When the tip portion of the optical probe 8H comes out of the endoscope tip, the tip spacer 69 is screwed into the connection member 53.

The optical probe 8H is drawn back to the extent that the side surface of the rear end side of the tip spacer 69 is made to contact with the tip of the endoscope, and insertion into the body cavity of the patient may be performed in this condition.

The present embodiment has the following effects.

Effects similar to those in the first embodiment are exhibited and, in addition, since the positioning unit is not deformed, positioning distance can be ensured stably and, therefore, operating ease for the operator is further improved.

(Seventh Embodiment)

The seventh embodiment according to the present invention will be described with reference to FIG. 17 and FIG. 18.

As shown in FIG. 17, an optical probe 8I according to the present embodiment includes a probe main body 101 having the configuration similar to that of the prior example, and a balloon sheath portion 102 for storing this probe main body 101 in the inside.

In the probe main body 101, the flexible shaft 45, through which an optical fiber is inserted, is inserted through the transparent sheath 42, in which the tip is sealed watertight with a sheath seal member 77 and which has pliability, and the tip of this flexible shaft 45 is fixed to the housing 44 together with the tip of the optical fiber.

In this housing 44A, a GRIN lens is fitted facing to the tip of the optical fiber, the prism 52 is fitted at the tip face thereof and, therefore, the light can exit from and enter into the opening provided on the housing 44.

The rear end of the flexible shaft 45 is held together with the rear end of the optical fiber by the connector portion 41 through an outer sheath receiver portion 103 while being kept to rotate freely. The rear end of the sheath 42 is fixed to the outer sheath receiver portion 103.

An external thread portion 103*a* is provided at the tip side of the outer perimeter surface of this outer sheath receiver portion 103, is thread-engaged with an internal thread portion 105*a* provided on the inner perimeter surface of a sheath fixing member 105, to which the rear end of a transparent outer sheath 104 constituting the balloon sheath portion 102 and having pliability is fixed, and, therefore, is fixed to the outer sheath receiver portion 103 while attachment and detachment can be performed freely.

An O-ring 106 for watertightness is stored in a circumferential groove provided on the inner perimeter surface of the sheath fixing member 105 on the side nearer to the rear end than is the internal thread portion 105*a*, and is in contact with the outer perimeter surface of the outer sheath receiver portion 103 placed inside it in order to keep watertightness airtightness.

As is shown in FIG. 18 under magnification, the tip of the outer sheath 104 is covered with an open base end of the bag-shaped balloon 108 having contraction and expansion properties via a balloon connection member 107, and these are fixed watertight with a string binding adhesion portion 109. In the sheath fixing member 105, a communication hole for communicating the inside and the outside is provided at the position, for example, more to the front than is the internal thread portion 105*a*, and the tip of a syringe 110 is inserted and fixed in this communication hole.

Consequently, by injecting a medium, for example, air or water, from this syringe 110, the balloon 108 is expanded and, therefore, the tip side of the sheath 42 can be positioned.

Others are similar to those in the configuration of the first embodiment.

Next, actions of the present embodiment will be described. When a medium, for example, air or water, is injected from the syringe 110, the space between the outer sheath 104 lumen and the sheath 42 outer surface is made to have a positive pressure and, therefore, the balloon 108 is expanded. When the medium is suctioned through the syringe 110, the pressure of the aforementioned space becomes equivalent to atmospheric pressure or a negative pressure and, therefore, the balloon 108 is contracted.

The balloon is contracted during insertion into the endoscope, and when the tip portion is protruded from the endoscope and observation is performed in the body cavity, the balloon 108 is expanded and, therefore, can be used as a positioning unit. The pint position with respect to the living-body tissue can be finely adjusted depending on the size of the balloon 108 expanded.

The balloon 108 may be of compliance type (expansion is based on the elastic deformation) or be of noncompliance type (the shape corresponding to that after expansion is formed beforehand, and it is contracted by applying a negative pressure when not in use).

The present embodiment has the following effects.

Effects similar to those in the first embodiment are exhibited and, in addition, since deformation is unlikely to occur even when pressed somewhat strongly against the living-body tissue compared to that in the case of the blade 54a, operating ease for the operator is improved.

Furthermore, since the pint position can be finely adjusted during inspection with one optical probe 8I, the operating ease is excellent and cost performance is superior.

(Eighth Embodiment)

The eighth embodiment according to the present invention will be described with reference to FIG. 19 to FIG. 21.

As shown in FIG. 19, an optical probe 8J according to the present embodiment is the optical probe 8I shown in FIG. 17 in which one end of an elastic tube 111 with the other end thereof being fixed to the tip of the outer sheath 104 is fixed on the sheath seal member 77 at the tip of the sheath 42.

This elastic tube 111 is in the shape of a tube having openings at the tip and the rear end, and is subjected to a shaping process beforehand in order that when no force is applied, an intermediate part of the tube body may protrude (evaginate) outside the radius and, therefore, a protrusion portion (evagination portion) 112 may be formed, as shown in FIG. 19 or FIG. 20.

The both ends of this elastic tube 111 are fixed watertight with string binding adhesion portions 113.

In the present embodiment, for example, the internal thread portion 105a of the sheath fixing member 105 is formed to be long and, therefore, an outer sheath movement mechanism is formed, in which the outer sheath 104 can be moved to the rear side by screwing into the external thread portion 103a of the sheath receiver portion 103.

Figure 21:
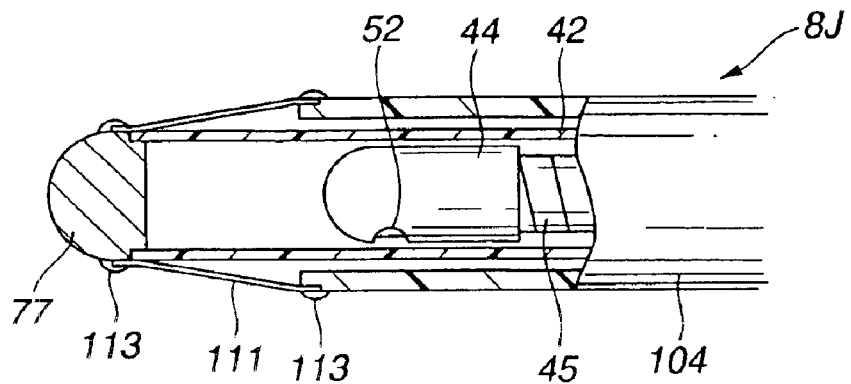
FIG. 21 is a sectional view showing the case where an outer sheath in the condition shown in FIG. 20 is moved toward the rear side, FIG. 22 to FIG. 24 relate to a ninth embodiment according to the present invention.

By moving the outer sheath 104 to the rear side, the tip of the outer sheath 104 is further moved to the rear side relative to the tip of the sheath 42 and, therefore, as shown in FIG. 21, it is possible to apply a pulling force to the elastic tube 111 and to prevent formation of the protrusion portion 112.

That is, the position (distance) for positioning can be changed with the movement amount based on the movement of the outer sheath 104 to the rear side. In the present embodiment, since the balloon 108 is not used, the syringe 110 is not provided. Others are similar to those in the configuration described with reference to FIG. 17.

Next, actions of the present embodiment will be described. As the sheath fixing member 105 is screwed into, since the tip portion of the outer sheath 104 is moved to the rear side, the elastic tube 111 is elongated in the longitudinal direction, and finally, the maximum outer diameter becomes equivalent to that of the outer sheath 104, as shown in FIG. 21.

Consequently, insertion into the endoscope is performed in the condition shown in FIG. 21, and when the tip is protruded, positioning procedure can be performed in the condition shown in FIG. 20. The value of the protrusion portion 112 of the maximum diameter of the elastic tube 111 can be adjusted by the amount of screwing of the sheath fixing member 105, and be used for positioning.

The present embodiment has the following effects.

The present embodiment has effects similar to those in the seventh embodiment.

(Ninth Embodiment)

The ninth embodiment according to the present invention will be described with reference to FIG. 22 to FIG. 24. The present embodiment has the configuration in which a basket type spacer is provided at the tip of the probe covered with an outer sheath and, therefore, positioning unit is provided.

Figure 22:
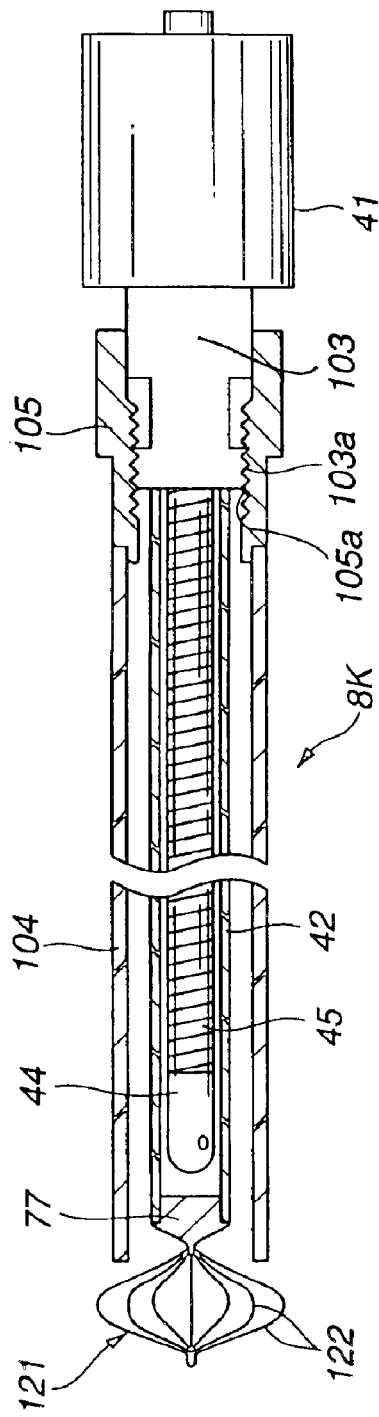
FIG. 22 is a sectional view showing an optical probe device according to the ninth embodiment.

An optical probe 8K according to the present embodiment shown in FIG. 22 is the optical probe 8J shown in FIG. 19 in which the tip of the outer sheath 104 is opened, and a basket type spacer 121 is provided on the sheath seal member 77 at the tip of the sheath 42.

Figure 23:
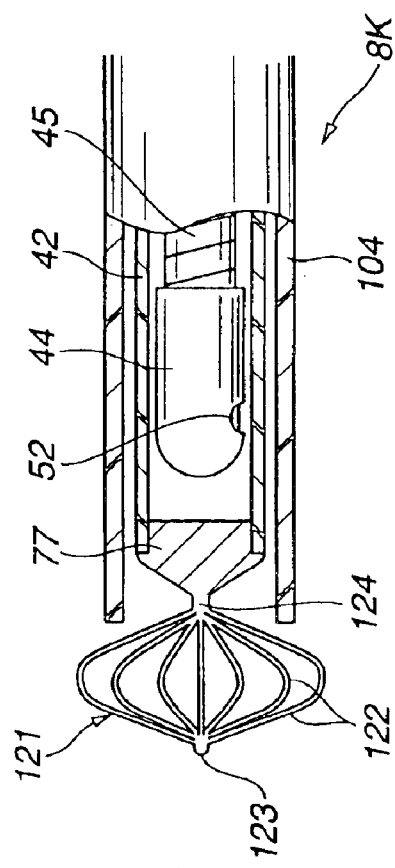
FIG. 23 is a sectional view showing the enlarged tip side shown in FIG. 22.

As shown in FIG. 23 under magnification, regarding this basket type spacer 121, a plurality of metal wires 122, each having been subjected to shape processing in order to bulge outside the radius, are made into a small diameter of bundle at weld portions 123 and 124 of both ends, and one of the weld parts is fixed to the sheath seal member 77.

In this condition, the outer diameter of the part, which is made from the metals 122 and which is bulged into the shape of a basket, of the basket type spacer 121 is larger than the outer diameter of the outer sheath 104.

In the present embodiment, the sheath fixing member 105 forms an outer sheath movement mechanism, in which the outer sheath 104 can be moved frontward or backward freely, by screwing into the sheath receiver portion 103.

By moving frontward the outer sheath 104 side, the bulged part of the basket type spacer 121 is pressed by the tip of the outer sheath 104 and, therefore, elastic deformation is brought about and the amount of bulge can be adjusted. By further moving it frontward, the basket type spacer 121 can be stored inside the outer sheath 104, as shown in FIG. 24. Others are similar to those in the configuration described with reference to FIG. 19.

Next, actions of the present embodiment will be described. As the amount of screwing of the sheath fixing member 105 is reduced, the position of the outer sheath 104 is moved to the tip face, and finally, as shown in FIG. 24, the basket type spacer 121 can be stored in the outer sheath 104 lumen while being deformed elastically.

Figure 24:
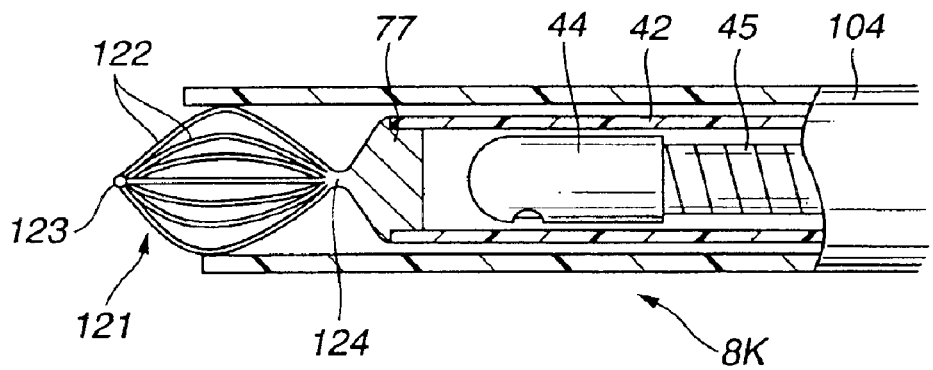
FIG. 24 is a sectional view showing the case where an outer sheath in the condition shown in FIG. 22 is moved toward the front side, FIG. 25 and FIG. 26 relate to a tenth embodiment according to the present invention.

Consequently, during insertion into the endoscope, the basket type spacer 121 is made to be in the condition shown in FIG. 24, and is inserted. During observation of the living-body tissue, it is made to be in the condition shown in FIG. 23 and, therefore, can be used as a positioning unit. The outer diameter of the basket can be finely adjusted based on the degree of drawing of the basket type spacer 121 into the outer sheath 104. Furthermore, when a foreign body, etc., is detected in the body cavity, the foreign body is taken into the inside of the basket type spacer and, therefore, the foreign body can be retrieved while the condition is made to be as shown in FIG. 23.

The present embodiment has the following effects.

The present embodiment has effects similar to those in the seventh embodiment and, in addition, takes on added value as an endo-therapy product for retrieving foreign bodies.

(Tenth Embodiment)

The tenth embodiment according to the present invention will be described with reference to FIG. 25 and FIG. 26.

Figure 25:
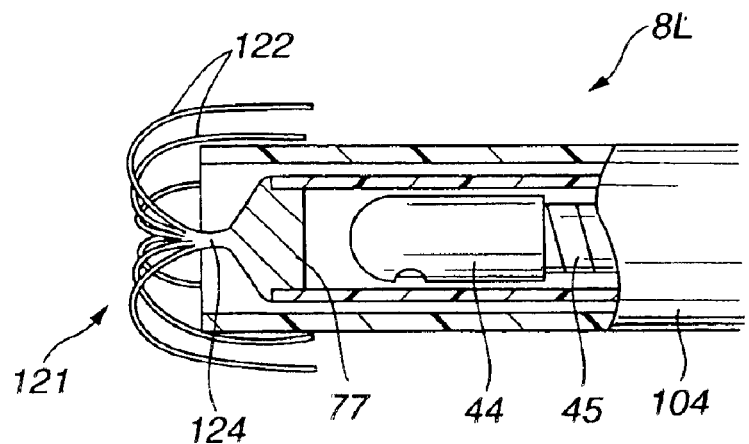
FIG. 25 is a sectional view showing the tip side of an optical probe device according to the tenth embodiment.
Figure 26:
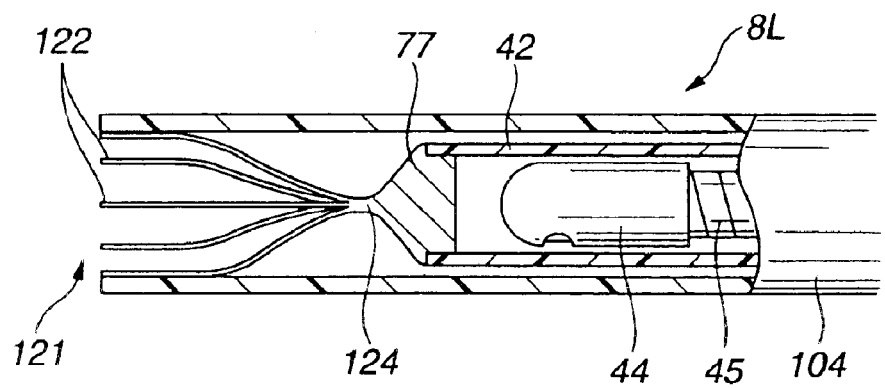
FIG. 26 is a sectional view showing the case where an outer sheath in the condition shown in FIG. 25 is moved toward the front side, FIG. 27 to FIG. 29 relate to an eleventh embodiment according to the present invention.

An optical probe 8L according to the present embodiment shown in FIG. 25 is the optical probe 8K shown in FIG. 22 in which the tip of the basket type spacer 121 is not made into a bundle, the tip of each metal wire 122 is subjected to shape processing in order to be folded back to the probe rear end side. Others are similar to those in the configuration according to the ninth embodiment.

Regarding actions of the present embodiment, in a manner similar to that in the ninth embodiment, the outer sheath 104 can be moved frontward or backward by screwing the sheath fixing member at the base end of the outer sheath 104. For example, when the amount of screwing is reduced, the outer sheath 104 is moved frontward and, therefore, as shown in FIG. 26, the basket type spacer 121 can be stored in the outer sheath 104. When the amount of screwing is increased from the condition shown in FIG. 26, the basket type spacer 121 can be protruded from the outer sheath 104 and, therefore, be used for positioning.

The present embodiment has the following effects.

The present embodiment has effects similar to those in the seventh embodiment and, in addition, since the positioning unit can be brought close to the light exit position compared to that in the ninth embodiment, operating ease for the operator is improved.

(Eleventh Embodiment)

The eleventh embodiment according to the present invention will be described with reference to FIG. 27 to FIG. 29.

Figure 27:
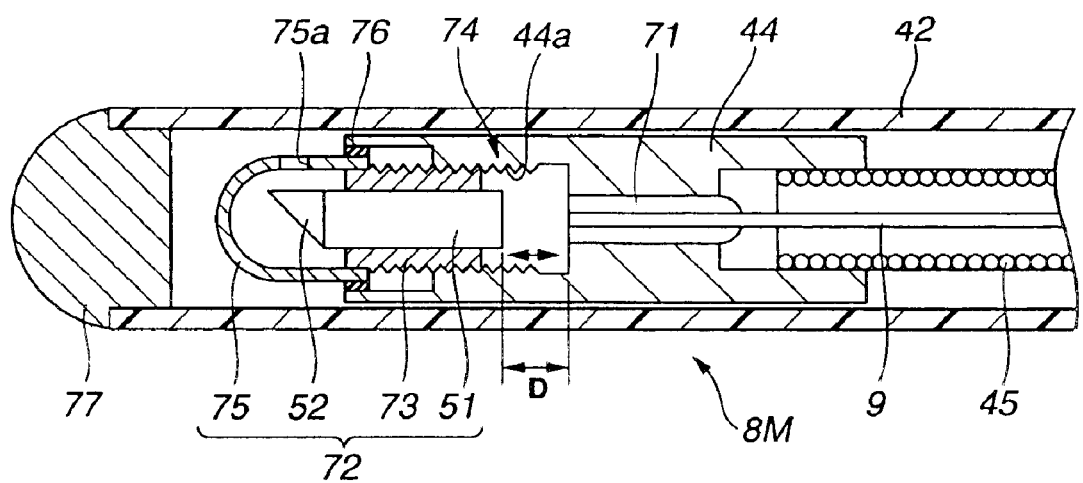
FIG. 27 is a sectional view showing the tip side of an optical probe device according to the eleventh embodiment.

As shown in FIG. 27, in an optical probe 8M according to the present embodiment, the flexible shaft 45 for transferring rotation from near side is inserted through the transparent sheath 42 which transmits light, the optical fiber 9 for transmitting the low-coherence light is inserted through this flexible shaft 45, the tip of the flexible shaft 45 is fitted into the lumen of the housing 44 and is adhered, and the tip of the optical fiber 9 is adhered and fixed to a reduced-diameter lumen part of the housing 44 with a ferrule 71 therebetween, while the tip face of the ferrule 71 is optically polished.

The inner diameter of the housing 44 forward of the tip face of the optical fiber 9 is enlarged stepwise, the internal thread portion 44a is formed on the inner perimeter surface thereof, and the external thread member 73 in the lens unit 72 formed from a GRIN lens 51, a prism 52, etc., is made to move freely, as indicated by an arrow, depending on the amount of the thread engagement into the internal thread portion 44a, and, therefore, a focus position adjustment mechanism 74 is formed in which the focus position can be changed.

In this lens unit 72, the GRIN lens 51 is put through the hollow portion of the hollow external thread member 73 provided with an external thread portion on the outer perimeter surface and is fixed with an adhesive, and the prism 52 is adhered at the tip face of this GRIN lens 51.

The base end of the cap 75 is fixed at the tip face of the external thread member 73, and the outer perimeter side of the prism 52 is covered with the cap 75. In this cap 75, the opening 75a is provided at the part where the light is made to exit from the prism 52.

The inner diameter of the housing 44 forward of the internal thread portion 44a is enlarged, a rubber ring 76 is fixed at tip portion thereof, and the outer perimeter surface of the cap 75 is in contact with the inner perimeter surface of this rubber ring 76 so as to apply a proper frictional force to the cap 75.

The tip of the sheath 42 is sealed watertight with the seal member 77 as well.

According to such a configuration, the distance D between the end face of the GRIN lens 51 and the optical fiber 9 with the ferrule 71 therebetween is changed by the amount of screwing of the lens unit 72 into the housing 44.

The focus position of the light beam exiting from the prism 52 can be adjusted by change of the distance D. The lens 72 can be prevented from rotating accidentally during normal use by friction between the rubber ring 76 and the cap 75.

Figure 28:
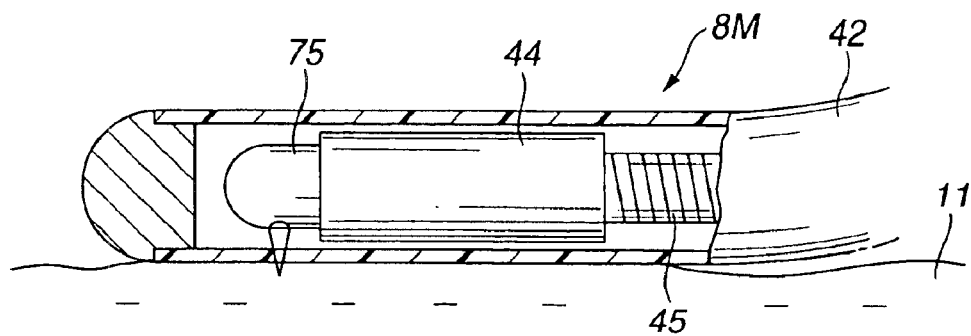
FIG. 28 is a diagram showing an example of the use in the condition wherein the focus distance is adjusted to be the neighborhood of the surface of the sheath in FIG. 27.

When the distance D is increased, the focus position can be brought close to the sheath 42 side, and the optical probe 8M can be used for the purpose of observation while being in contact with the living-body tissue 11, as shown in FIG. 28.

In this case, when the distance D is further reduced, observation can be performed while the focus falls on the deep part side of the living-body tissue 11.

Figure 29:
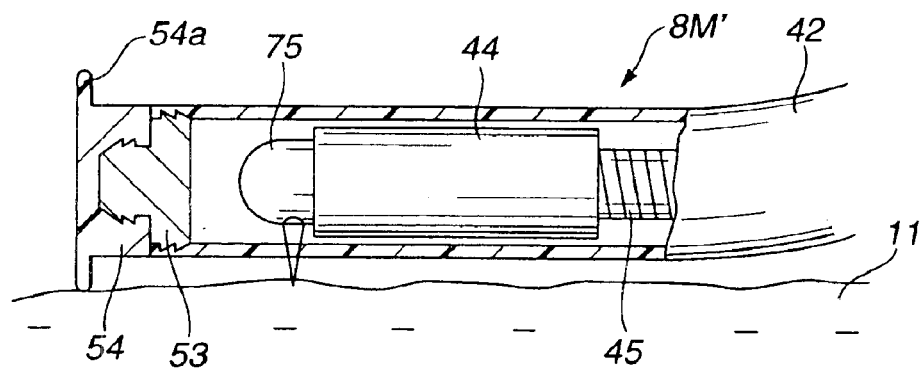
FIG. 29 is a diagram showing an example of the use in the condition wherein the focus distance is adjusted to be larger than the neighborhood of the surface of the sheath in FIG. 27, FIG. 30 to FIG. 31B relate to a twelfth embodiment according to the present invention.

Since the focus position can be moved away when the distance D is further reduced, it is possible to use for the observation in which the observation range is extended by, for example, the optical probe 8M' provided with a positioning unit, such as the blade member 54, at the tip with the connection member 53 therebetween, as shown in FIG. 29.

The present embodiment has the following effects.

Since the focus position of the low-coherence light can be adjusted, various observation methods and fine adjustment of the pint position can be dealt with by one optical probe 8M. Therefore, the burdens on the user can be reduced.

(Twelfth Embodiment)

The twelfth embodiment according to the present invention will be described with reference to FIG. 30 and FIG. 31B.

Figure 30:
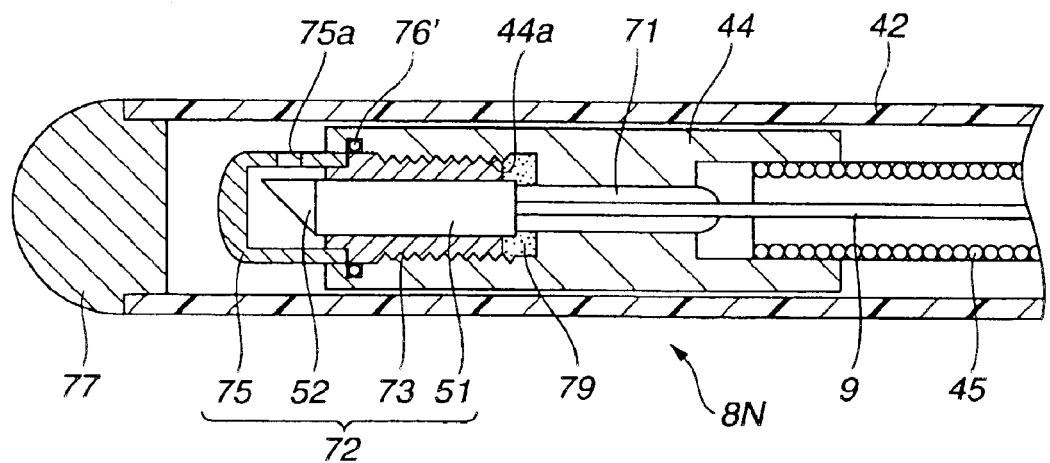
FIG. 30 is a sectional view showing the tip side of an optical probe device according to the twelfth embodiment.

An optical probe 8N shown in FIG. 30 is the optical probe 8M shown in FIG. 27 in which the tips of the optical fiber 9 and the ferrule 71 provided on the periphery thereof are further moved frontward and are made to contact with the rear end face of the GRIN lens 51, and the gap portion around the rear end of the GRIN lens 51 and around the tip of the ferrule 71 in the inner perimeter of the housing 44 of this contact part is filled with matching oil 79.

Although the inner diameter of the tip side of the housing 44 has been enlarged and the rubber ring 76 for applying frictional force has been provided in FIG. 27, in the present embodiment, the inner perimeter surface of the tip side of the housing 44 is fitted to the outer perimeter surface of the tip side of the external thread member 73, and an O-ring 76' for watertightness is provided.

The optical probe 8M shown in FIG. 27 have had the configuration in which the focus position has been able to adjust by the adjustment of the amount of screwing of one lens unit 72. However, in the present embodiment, a lens unit 72B (refer to FIG. 31B) provided with a GRIN lens 51b having a length b different from the length a (refer to FIG. 31A) of the GRIN lens 51 in the lens unit 72 shown in FIG. 30 is included.

Then, the lens units 72 and 72B fitted to the housing 44 are used alternatively and, therefore, the focus position adjustment mechanism is formed. Others are similar to those in the configuration in the optical probe 8M shown in FIG. 27.

Figure 31A:
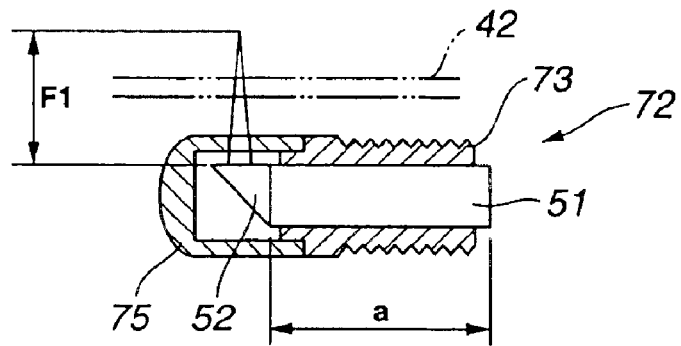
FIG. 31A and FIG. 31B are diagrams for explaining a manner in which the focus distances are changed depending on lens units used, FIG. 32 and FIG. 33 relate to a thirteenth embodiment according to the present invention.
Figure 31B:
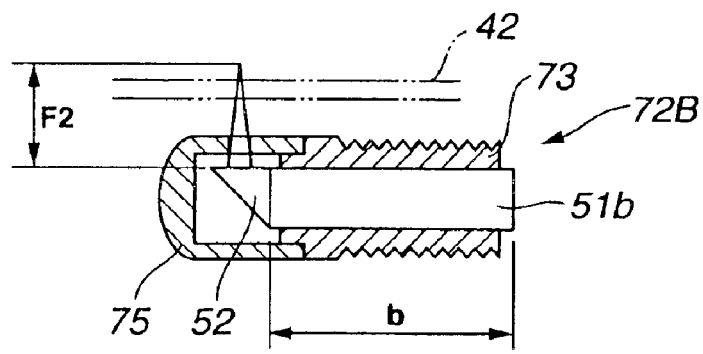

According to such a configuration, as shown in FIG. 31A and FIG. 31B, the focus distances F1 and F2 can be changed by the use of the lens units 72 and 72B including the GRIN lenses 51 having different lengths and, therefore, actions similar to those in the eleventh embodiment can be achieved.

Since the GRIN lens 51 and the ferrule 71 are in contact with each other, and the matching oil is present even in a minute gap, transmission loss of the light and attenuation due to reflection can be reduced by a large degree.

The present embodiment has the following effects.

The present embodiment can achieve effects nearly equivalent to those in the eleventh embodiment and, in addition, since transmission efficiency of the light, etc., can be improved, and OCT images having more excellent image quality can be produced, precise diagnosis can be performed with ease.

(Thirteenth Embodiment)

The thirteenth embodiment according to the present invention will be described with reference to FIG. 32 and FIG. 33.

Figure 32:
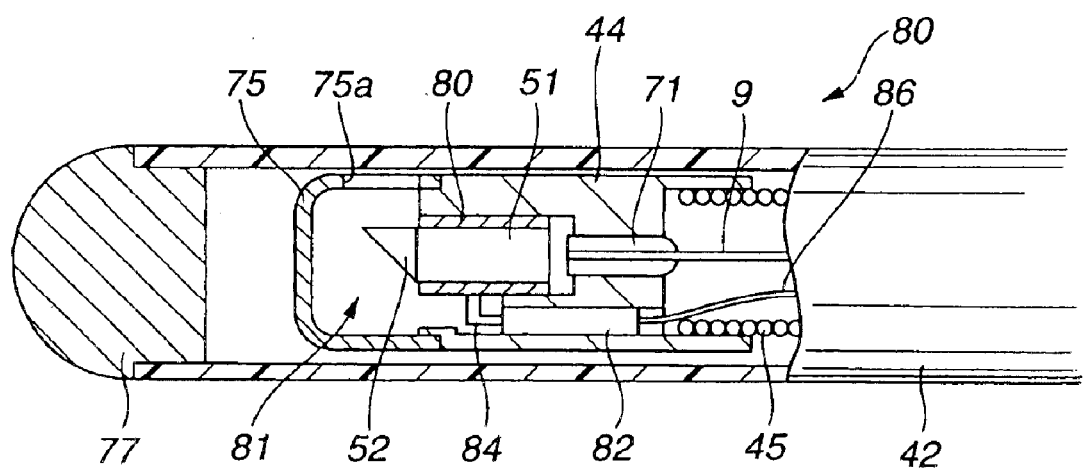
FIG. 32 is a sectional view showing the tip side of an optical probe device according to the thirteenth embodiment.

Regarding an optical probe 80 shown in FIG. 32, in the sheath 42, the tip of the flexible shaft 45 inserted with the optical fiber 9 is fixed to the housing 44, the tip of the optical fiber 9 is also adhered and fixed to the part having a reduced diameter of the housing 44 with the ferrule 71 therebetween, and in the housing 44 having an enlarged diameter on the side forward thereof, a lens unit 81, in which the GRIN lens 51 adhered with the prism 52 is held by a lens frame 80, is stored. The lens frame 80 forming the lens unit 81 is stored while it can slide freely in the longitudinal direction of the housing 44.

This lens frame 80 is connected to a movable body 83 (refer to FIG. 33) constituting a piezoelectric actuator unit 82 stored in an actuator storage portion of the housing 44 with a connection member 84 in the shape of the letter L therebetween. The movable body 83 is moved by applying a driving signal to a piezoelectric body 85 of the piezoelectric actuator unit 82 via a signal wire 86 and, therefore, the lens unit 80 connected to the movable body 83 can be moved.

Figure 33:
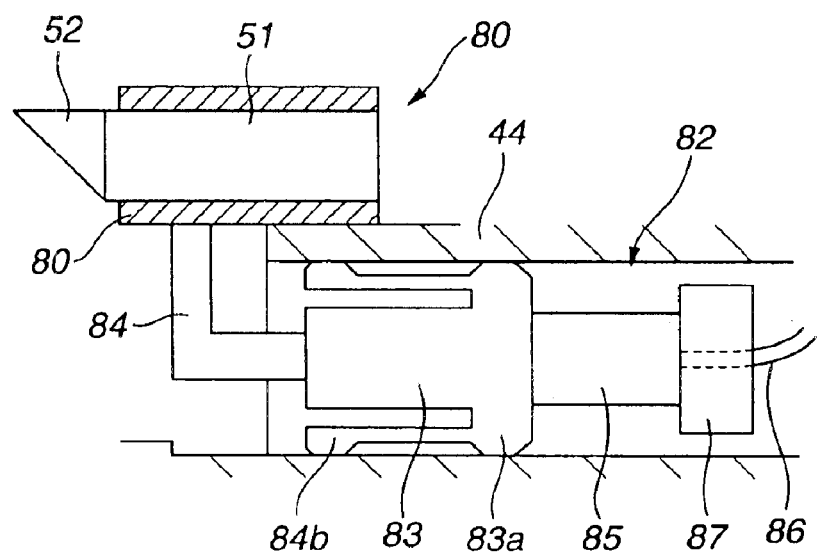
FIG. 33 is a sectional view showing the structure of a piezoelectric actuator unit, FIG. 34 to FIG. 36 relate to a fourteenth embodiment according to the present invention.

As shown in FIG. 33, the piezoelectric actuator unit 82 is stored in order that a connection portion 83a at the rear end and a connection portion 84b at the tip of the movable body 83 may be in contact with the inner wall of the actuator storage portion of the housing 44. In this case, the connection portion 84b at the tip is formed outside a slit provided in the movable body 83, and, therefore, contacts elastically with the inner wall of the actuator storage portion.

The tip of the piezoelectric body 85 is fixed to the rear end of this movable body 83, and an inertia body 87 is fixed at the rear end of the piezoelectric body 85. By applying the first or second driving pulse signal having different waveforms via the signal wire 86 connected to electrodes, not shown in the drawing, provided at the tip and rear end of the piezoelectric body 85, the piezoelectric body 85 is contracted or is elongated and, therefore, the movable body 83 can be moved frontward or backward.

In this case, the waveforms and actions in that case of the first or second driving pulse signal for causing frontward or backward movement are described in detail in Japanese Unexamined Patent Application Publication No. 6-22903.

As shown in FIG. 32, the rear end of the cap 75 is adhered and fixed to the tip of the housing 44. In this case, since the lens unit 81 can be moved frontward or backward, the opening 75a is formed while being extended in the frontward and backward direction. The tip opening of the sheath 42 is sealed watertight with the seal member 77.

According to such a configuration, the relative position of the lens unit 81 in the housing 44 can be changed based on the driving pulse signal applied to the piezoelectric actuator unit 82 by the signal wire 86, and, therefore, the focus position can be adjusted by changing distance between the GRIN lens 51 and the ferrule 71 end face.

The present embodiment has the following effects.

The present embodiment has effects nearly equivalent to those in the eleventh embodiment.

In addition, since the observation method and location and optimum focus position can be changed during inspection, an optimum image can always be produced and, therefore, diagnostic performance can be improved.

Since the focus position can be changed without the operation of, for example, removing the sheath 42, operating ease is improved.

(Fourteenth Embodiment)

Figure 34:
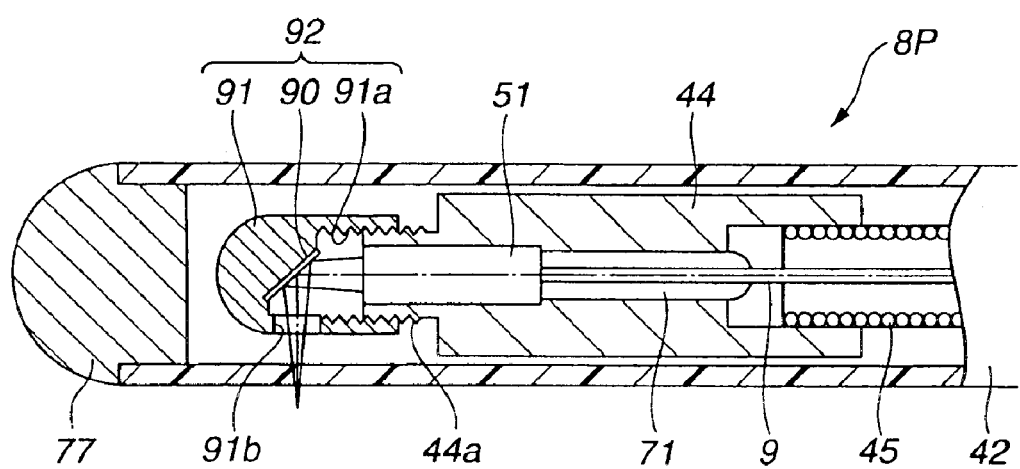
FIG. 34 is a sectional view showing the tip side of an optical probe device according to the fourteenth embodiment.

The fourteenth embodiment according to the present invention will be described with reference to FIG. 34 to FIG. 36.

Regarding an optical probe 8P, the flexible shaft 45 for transferring rotation from near side is inserted through the transparent sheath 42, and the optical fiber 9 for guiding the light from near side is inserted through the flexible shaft 45.

The tip of the flexible shaft 45 is adhered to the rear end of the housing 44 with an adhesive, etc., and the tip of the optical fiber 9 is adhered and fixed to a reduced-diameter lumen of the housing 44 with the ferrule 71 therebetween, while the tip side of the ferrule 71 is polished. The diameter of the housing 44 facing the tip face of the optical fiber 9 is enlarged, and the GRIN lens 51 is fixed to the housing 44 while coinciding with the optical axis of the optical fiber 9.

The tip outer perimeter of this housing 44 is made to have a reduced diameter by formation of a step, an external thread portion 44a is provided on the outer perimeter surface thereof, and, therefore, an internal thread portion 91a of a mirror unit 92 formed from a cap 91 provided with a reflecting mirror 90 in the inside can be screwed and be fitted.

As described above, the mirror unit 92 is composed of the cap 91 and the reflecting mirror 90 adhered and fixed while inclining on the order of 45 degrees relative to the optical axis in the cap 91. The internal thread portion 91a is provided on the inner perimeter surface of the mouth (base end) of the cap 91 in order to screw into the external thread portion 44a. On the side of the cap 91, in order that the light, the optical path of which has been changed by on the order of 45 degrees with the reflecting mirror 90, can pass through, an opening 91b centering the optical axis thereof is provided. The outer diameter of the cap 91 is smaller than the housing 44.

The tip opening of the sheath 42 is sealed watertight with the seal member 77.

According to such a configuration, the light transmitted by the optical fiber 9 passes through the GRIN lens 51 from the tip of the ferrule 71, is made to exit from the tip thereof, is reflected by the reflecting mirror 90, and is guided outside the sheath 42 as a light beam.

At this time, the light beam is condensed outside the sheath 42 due to condensing action of the GRIN lens 51. The interval between the reflecting mirror 90 and the GRIN lens 51 can be adjusted based on the amount of screwing of the mirror unit 92 into the housing 44. By this change of the interval, the focus position of the light beam can be changed.

Figure 35:
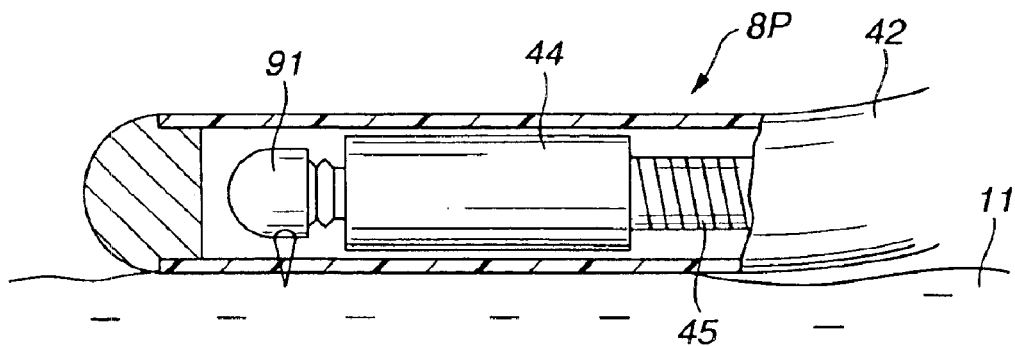
FIG. 35 is a diagram showing an example of the use in the condition wherein the focus distance is adjusted to be the neighborhood of the surface of the sheath by a mirror unit in FIG. 34.

When the interval is increased, the focus position can be brought close to the sheath 42, and the optical probe 8P can be used for the purpose of observation while being in contact with the living-body tissue 11, as shown in FIG. 35.

Figure 36:
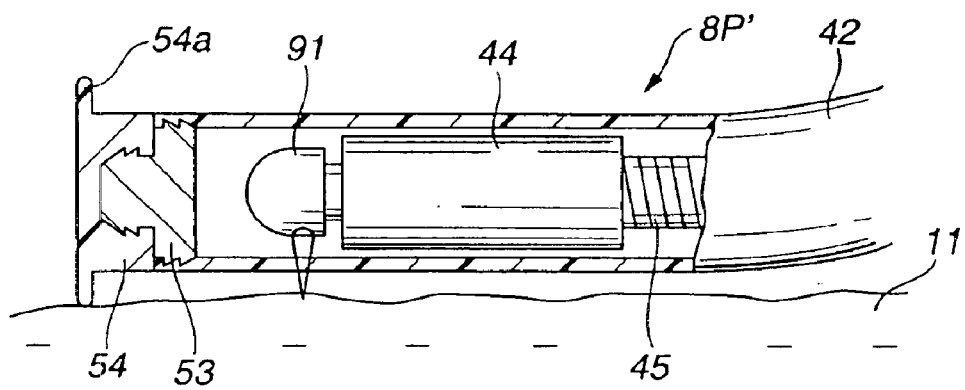
FIG. 36 is a diagram showing an example of the use in the condition wherein the focus distance is adjusted to be larger than the neighborhood of the surface of the sheath by a mirror unit in FIG. 34, FIG. 37 and FIG. 38 relate to a sixteenth embodiment according to the present invention.

Since the focus position can be moved away when the distance is reduced, it is possible to use for the observation in which the observation range is extended by the optical probe 8P', for example, provided with a positioning unit, such as the blade member 54, at the tip of the sheath 42 with the connection member 53 therebetween, as shown in FIG. 36.

Since the outer diameter of the cap 91 is small relative to the housing 44, even when rotation is transferred by the flexible shaft 45 and the configuration in the inside of the sheath 42 is rotated, it can be prevented that the mirror unit 92 contacts with the sheath 42, and the amount of screwing with respect to the external thread portion 44a is changed due to friction.

The present embodiment has the following effects.

Since the beam focus position of the low-coherence light can be adjusted, various observation methods and fine adjustment of the pint position can be dealt with by one optical probe 8P or 8P'. Therefore, the burdens on the user can be reduced.

(Fifteenth Embodiment)

The fifteenth embodiment according to the present invention will be described with reference to FIG. 37 and FIG. 38.

Figure 37:
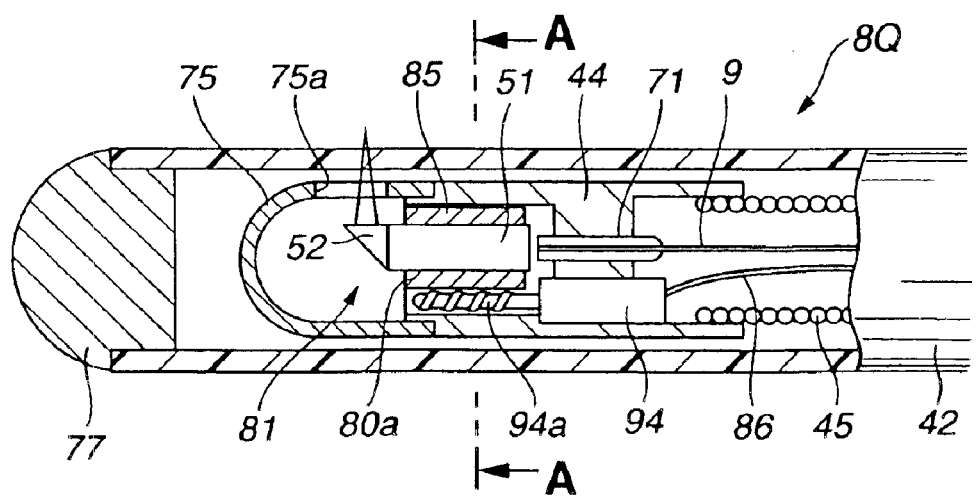
FIG. 37 is a sectional view showing the tip side of an optical probe device according to the sixteenth embodiment.

As shown in FIG. 37, an optical probe 8Q according to the present embodiment is the optical probe 80 shown in FIG. 32 in which a micromotor 94 is provided on the housing 44 instead of the piezoelectric actuator unit 82, a worm gear 94a is fitted to a rotation output shaft of the micromotor 94 and is meshed with a worm gear 80a on the lens unit 81 side, the lens unit 81 is moved frontward or backward by applying a driving signal for rotating the micromotor 94 in forward or reverse direction via the signal wire 86 and, therefore, the focus position can be changed.

Specific description will be made. Regarding an optical probe 8Q, in the sheath 42, the tip of the flexible shaft 45 inserted with the optical fiber 9 is fixed to the housing 44, the tip of the optical fiber 9 is also adhered and fixed to the part having a reduced diameter of the housing 44 with the ferrule 71 therebetween, and in the housing 44 having an enlarged diameter on the side forward thereof, a lens unit 81, in which the GRIN lens 51 adhered with the prism 52 is held by a cylindrical lens frame 80, is stored.

Figure 38:
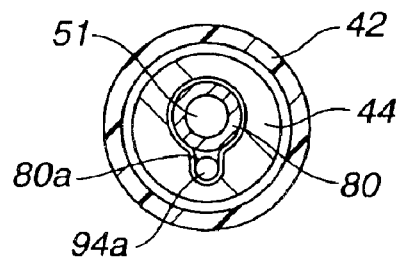
FIG. 38 is a sectional view of the section A—A shown in FIG. 37, FIG. 39 to FIG. 42 relate to a sixteenth embodiment according to the present invention.

As shown in FIG. 38, the lens frame 80 forming the lens unit 81 is fitted into the inner perimeter of the housing 44 and is stored while it can slide freely in the longitudinal direction.

The worm gear 80a integrally provided at the bottom end side of this lens frame 80 is meshed with the worm gear 94a of the rotation output shaft of the micromotor 94 stored and fixed in the motor storage portion of the housing 44. That is, the lens unit 81 and the micromotor 94 are mechanically connected. The cap 75 is provided at the tip of the housing 44, and the opening 75a is provided on the side surface facing the exit surface of the prism 52. The tip opening of the sheath 42 is sealed watertight with the seal member 77. Others are the same as those in the configuration described with reference to FIG. 19.

The actions of the present embodiment will be described below.

The light transmitted by the optical fiber 9 exits from the tip face thereof, passes through the GRIN lens 51 and the prism 52 so as to become a light beam, and exits from the side surface of the sheath 42.

At this time, the light beam comes into a focus by the condensing action of the GRIN lens 51. When the micromotor 94 is rotated, the torque of the motor 94 is converted to a linear motion by the worm gear mechanism, and the lens unit 81 moves in the longitudinal direction in the housing 44.

The interval between the tip face of the optical fiber 9 and the GRIN lens 51 can be adjusted by movement of the lens unit 81. Consequently, the focus position of the light beam can be changed. That is, when the interval between the tip face of the optical fiber 9 and the GRIN lens 51 is increased, the focus position can be brought close to the sheath 42, and when the interval is reduced, the focus position can be moved away. Therefore, effects similar to those in the eleventh embodiment described with reference to FIG. 28 and FIG. 29 can be achieved.

The present embodiment has the following effects.

The present embodiment has effects nearly equivalent to those in the eleventh embodiment and, in addition, since the observation method and location and optimum focus position can be changed during inspection, an optimum image can always be produced and, therefore, diagnostic performance can be improved.

Since the focus position can be changed without the need for removal of the sheath 42, and the like, operating ease is improved.

(Sixteenth Embodiment)

The sixteenth embodiment according to the present invention will be described with reference to FIG. 39 to FIG. 42.

Figure 39:
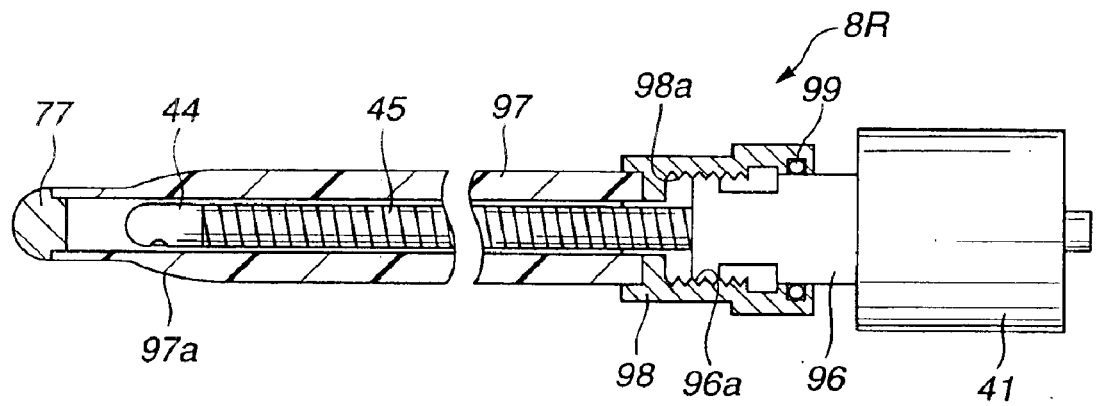
FIG. 39 is a sectional view showing the optical probe device according to the sixteenth embodiment.

Regarding an optical probe 8R shown in FIG. 39, the rear end of the flexible shaft 45, through which the optical fiber is inserted, is fixed together with the rear end of the optical fiber in the connector portion 41 through the inside of a sheath receiver portion 96 while being free to rotate. The tip of the flexible shaft 45 is fixed in the housing 44 together with the optical fiber inserted through the inside thereof.

In the housing 44, the GRIN lens is fixed facing the tip face of the optical fiber, and the prism 52 is adhered at the tip face thereof.

The tip opening of a transparent sheath 97 covering the flexible shaft 45 and the housing 44 at the tip thereof is sealed watertight with the seal member 77, and a sheath fixing member 98 provided at the rear end of this sheath 97 is fixed to the sheath receiver portion 96 by thread engagement.

Figure 40:
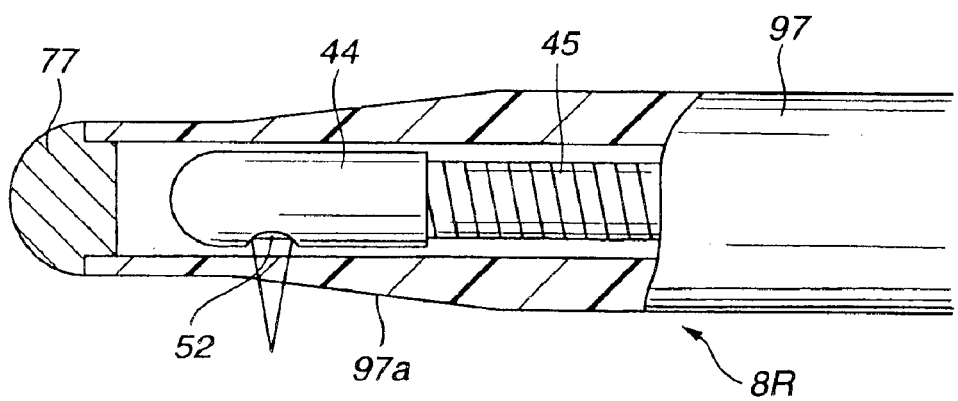
FIG. 40 is a sectional view showing the enlarged tip side shown in FIG. 39.

As shown in FIG. 40, in the present embodiment, regarding the sheath 97, the tip sealed with the seal member 77 has a small thickness, in the neighborhood of the outside of the housing 44, a varying-thickness portion 97a is formed, in which the outer diameter from the tip side toward the rear side is varied in order that the thickness is increased gradually and the outer diameter is enlarged to have the shape of a taper, and the part rearward of the part having the most enlarged diameter is kept to have an increased thickness and is connected to the sheath fixing member 98.

As shown in FIG. 39, an external thread portion 96a is formed on the sheath receiver portion 96, an internal thread portion 98a to thread-engage the external thread portion 96a is formed on the sheath fixing member 98, the sheath 97 side can be moved in the longitudinal direction thereof by adjusting the thread engagement amount of screwing of the sheath fixing member 98 side, and, therefore, a movable mechanism capable of changing the distance from the outer surface of the sheath 97 to the focus position by changing the thickness of the sheath 97 facing the housing 44 is formed.

In the present embodiment, the light beam exiting from the prism 52 is adjusted to come into a focus outside the part having a maximum outer diameter of the sheath 97.

An O-ring 99 is provided on the inner perimeter in the neighborhood of the rear end of the sheath fixing member 98 while being contacted circumferentially with the sheath receiver portion 96 in order to keep watertightness.

Figure 41:
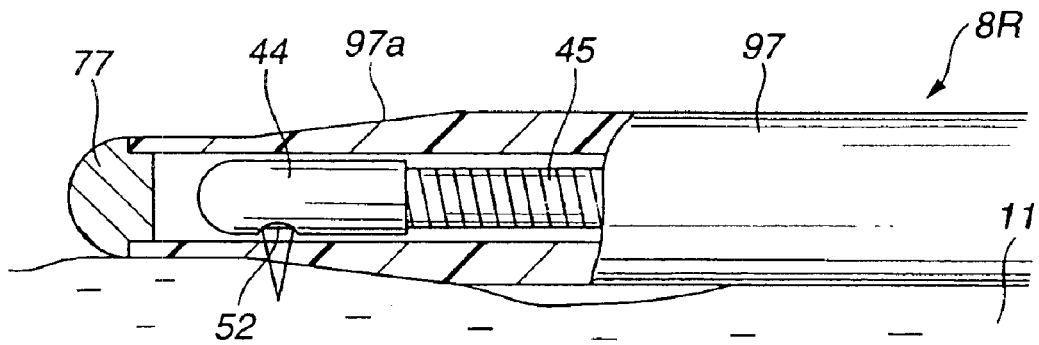
FIG. 41 is a diagram showing an example of the use in the condition wherein a sheath is moved toward the rear side and, therefore, the focus is adjusted on a position farther than the neighborhood of the surface of the sheath.

Next, description of the actions of the present embodiment will be explained. The relative position of the prism 52 with respect to the sheath 98 can be changed frontward or backward based on the amount of screwing of the sheath fixing member 98 into the sheath receiver portion 96. That is, In the case where adjustment is performed in order that the prism 52 faces the small thickness part on the tip side of the sheath 97, when the outer perimeter surface of the sheath 97 is made to contact with the living-body tissue 11 and light is radiated as shown in FIG. 41, since the light comes into a focus on a position relatively inner than the surface of the living-body tissue 11, the tissue structure slightly inner than the surface can be observed at high resolution.

Figure 42:
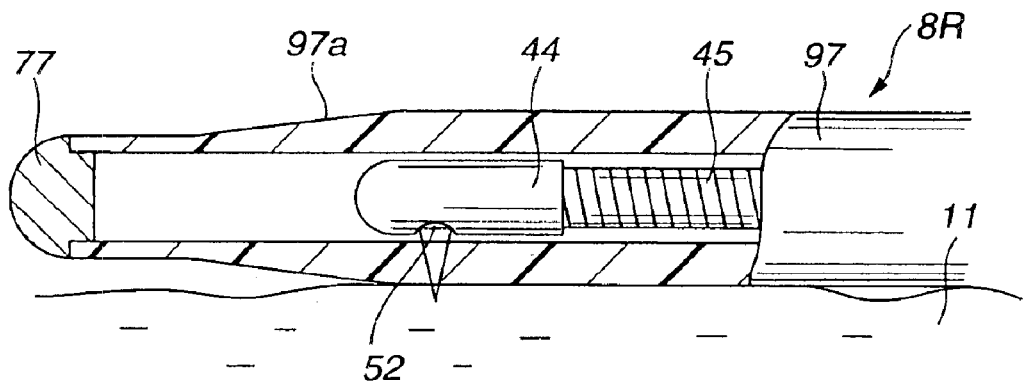
FIG. 42 is a diagram showing an example of the use in the condition wherein a sheath is moved toward the front side and, therefore, the focus is adjusted on a position in the neighborhood of the surface of the sheath, FIG. 43A to FIG. 45B relate to a seventeenth embodiment according to the present invention.

Conversely, when adjustment is performed in order that the prism 52 faces the large thickness part of the sheath 97, since the light comes into a focus on a position in the neighborhood of the surface of the living-body tissue 11 as shown in FIG. 42, the surface of the living-body tissue 11 can be observed over a wide range at high resolution.

The present embodiment has the following effects.

The present embodiment has effects similar to those in the eleventh embodiment and, in addition, since a complicated and expensive movable mechanism at the sheath tip side is unnecessary in contrast to the sixteenth embodiment, ease of assembly is improved and cost is reduced.

(Seventeenth Embodiment)

The seventeenth embodiment according to the present invention will be described with reference to FIG. 43A to FIG. 45B.

Figure 43A:
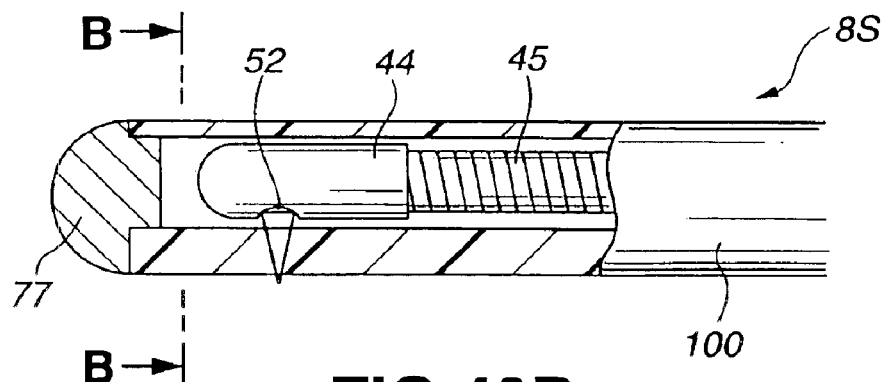
FIG. 43A is a diagram showing the tip side of an optical probe device according to the seventeenth embodiment and a sectional structure thereof.

As shown in FIG. 43A, regarding an optical probe 8S, the flexible shaft 45 inserted with an optical fiber, not shown in the drawing, is inserted through a transparent sheath 100, in which the tip is sealed watertight with the seal member 77, and the tip of the flexible shaft 45 is fixed in the housing 44 together with the tip of the optical fiber.

In the housing 44, the GRIN lens and the prism 52 are stored as described in the first embodiment.

Figure 43B:
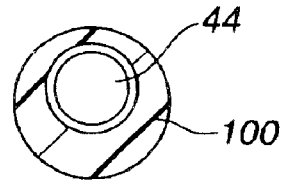
FIG. 43B is a sectional view of the section indicated by line B—B in FIG. 43A.

In the present embodiment, the sheath 100 is formed in order that the center axis of the inner perimeter is decentered relative to the outer perimeter thereof as shown in FIG. 43B and, therefore, regarding the configuration, the thicknesses distribute in the circumferential direction.

The light beam exiting from the prism 52 is adjusted to come into a focus slightly outside the sheath outer surface at the maximum thickness part of the sheath 100 (condition shown in FIG. 43A).

In the present embodiment, since the thickness of the sheath 100 in the optical path exiting from the prism 52 is varied in the circumferential direction, the focus distance from the outer surface of the sheath 100 toward the living-body tissue side can be changed by changing the position in the circumferential direction of the sheath 100 at which it is made to contact with the living-body tissue.

The actions of the present embodiment will be described below. The focus position of the light beam can be changed based on the surface, which is made to contact with the living body, of the sheath 100.

Figure 44A:
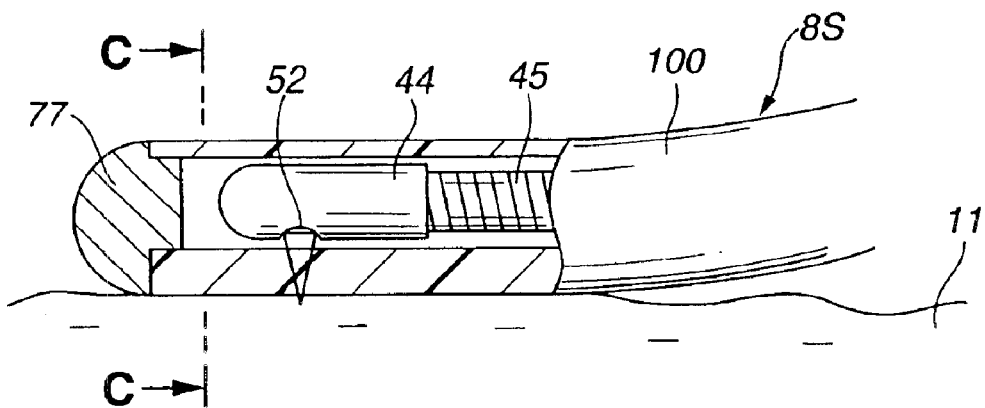
FIG. 44A is a diagram showing an example of the use in the condition wherein a part having a large thickness is in contact with living-body tissue.
Figure 44B:
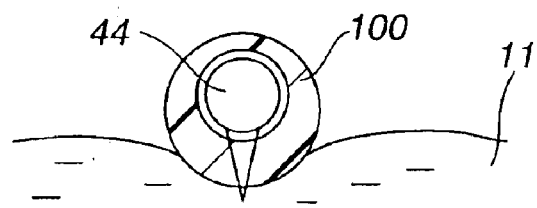
FIG. 44B is a sectional view of the section indicated by line C—C in FIG. 44A.
Figure 45A:
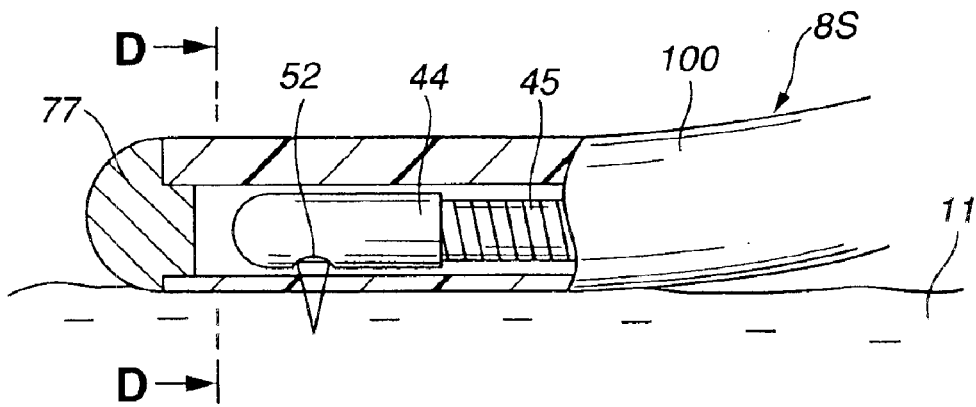
FIG. 45A is a diagram showing an example of the use in the condition wherein a part having a small thickness is in contact with living-body tissue.
Figure 45B:
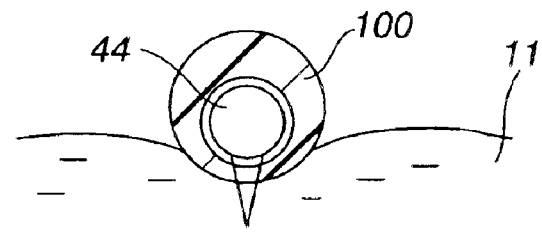
FIG. 45B is a sectional view of the section indicated by line D—D in FIG. 45A, FIG. 46 to FIG. 51 relate to an eighteenth embodiment according to the present invention.

As shown in FIGS. 44A and 44B, when observation is performed while the large thickness surface of the sheath is in contact with the living-body tissue 11, the neighborhood of the surface of the living-body tissue 11 can be observed over a wide range at high resolution. As shown in FIGS. 45A and 45B, when observation is performed while the small thickness surface of the sheath is in contact with the living-body tissue 11, a slightly inner part of the living-body tissue 11 can be observed at high resolution.

The present embodiment has the following effects.

The present embodiment has effects similar to those in the sixteenth embodiment and, in addition, since the mechanically movable portion is unnecessary, cost is reduced, and, furthermore, since operation is simplified, operating ease for the operator is improved compared to the sixteenth embodiment.

(Eighteenth Embodiment)

The eighteenth embodiment according to the present invention will be described with reference to FIG. 46 to FIG. 51. The following embodiments describe those characterized in tip portions of the endoscopes provided with a function as a positioning unit used together with an optical probe.

Figure 46:
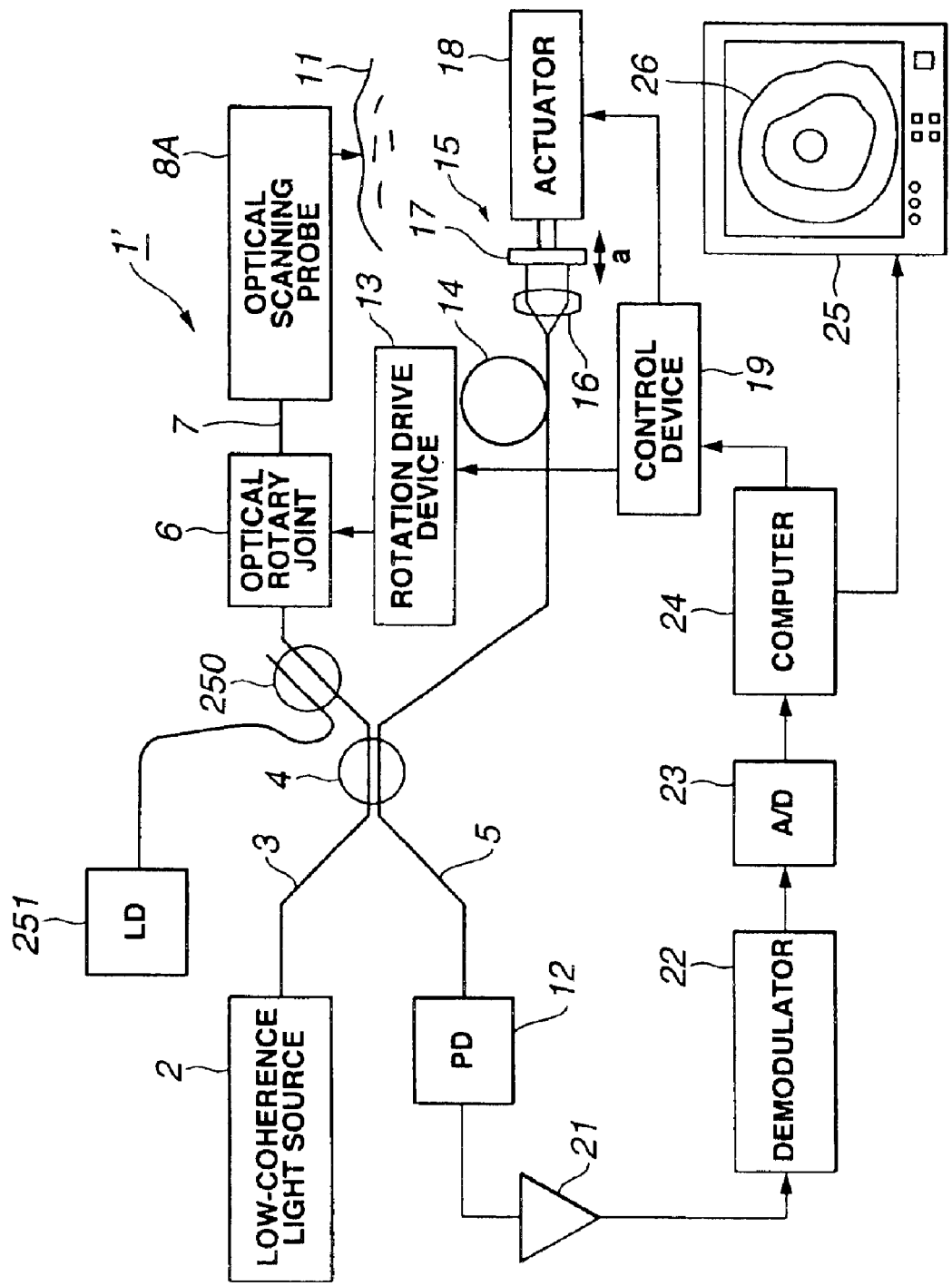
FIG. 46 is a configurational diagram showing the configuration of an optical tomography device provided with the eighteenth embodiment.

An optical tomography device 1' shown in FIG. 46 is the optical tomography device 1 shown in FIG. 1 in which an optical coupler portion 250 is interposed on the tip side of the optical coupler portion 4, and, therefore, visible light from a laser diode (abbreviated as LD) 251 can be blended to the light from the low-coherence light source 2 and a scanning locus of the light beam can visually observe as an aiming beam.

On the side nearer to the tip than is the optical coupler portion 250, an optical rotary joint 6 which performs coupling capable of transmitting light between a non-rotary portion and a rotary portion is interposed, and is connected to, for example, an optical probe device (hereafter abbreviated as optical probe) 8A according to the first embodiment with the third single mode fiber 7 in this optical rotary joint 6 therebetween. Others are similar to those in the configuration of the first embodiment, and the same constituents are indicated by the same reference numerals and explanations thereof are omitted.

Figure 47:
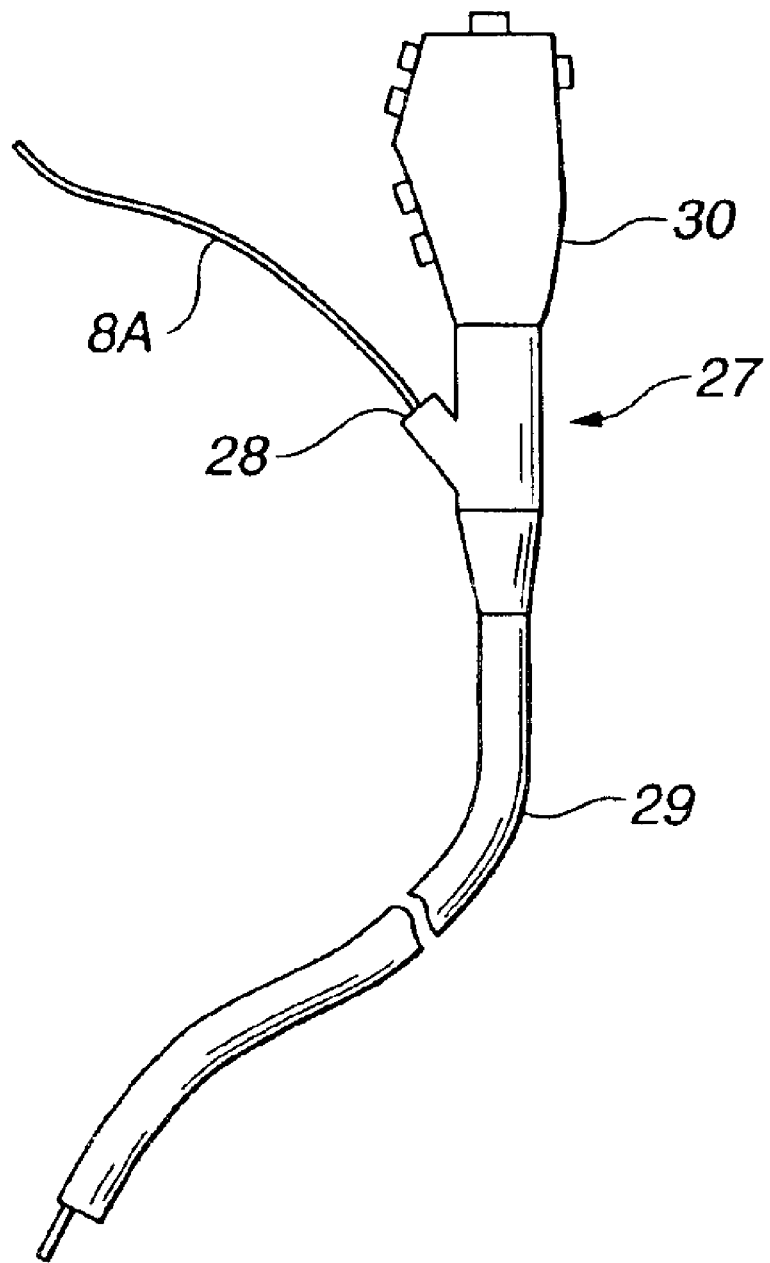
FIG. 47 is a diagram showing an endoscope through which an optical probe is inserted.

This optical probe 8A passes through a forceps insertion hole 28 of the endoscope 27 and a channel 28a for forceps insertion (refer to FIG. 50), and can protrude the tip side of the optical probe 8A from the tip opening thereof, as shown in FIG. 47.

This optical probe 27 includes a slender insertion portion 29 in order to be inserted into a body cavity with ease, and a wide control portion 30 is provided at the rear end of this insertion portion 29. The forceps insertion hole 28 is provided in the neighborhood of the front end of this insertion portion 30, and this forceps insertion hole 28 is communicated with the channel 28a for forceps insertion (refer to FIG. 50) in the inside thereof.

A light guide (not shown in the drawing) is inserted through the insertion portion 29. The entrance end of this light guide 28b is connected to the light source device, and illumination light is transmitted and is made to exit from a illumination window provided at the tip of the insertion portion 29 so as to illuminate an affected area, etc. An observation window is provided adjacently to the illumination window, and an objective optical system is fitted to this observation window in order to observe the illuminated affected area, etc., with the optical system.

Under observation with the optical observation system at the tip portion of the endoscope 27, the living-body tissue 11 side of the noted part, for example, an affected area, is radiated with low-coherence light by the optical probe 8A, tomogram data of the inside of the living-body tissue 11 are gained, and the OCT image 26 can be displayed on the display surface of the monitor 25.

An endoscope tip hood according to the present embodiment is fitted to the tip portion of the insertion portion 29 of the endoscope 27 when the optical probe 8A is used by inserting through the channel 28a for forceps insertion (refer to FIG. 50) from the tip opening of the forceps insertion hole 28 of the endoscope 27. As shown in FIG. 48A and FIG. 48B, the endoscope tip hood 101 has a configuration in which a cylindrical transparent hood 103 having a hole portion 102 on a side portion made of, for example, plastic, having an excellent light transmission property, and an elastic tube 104 which has an inner diameter smaller than the outer diameter of the transparent hood 103 and which is made of an elastic material are connected at a connection portion 105.

A groove 106 is provided on the outer perimeter of the transparent hood 103 in the connection portion 105. The inner surface of the elastic tube 104 is press-fitted to the outer surface of the transparent hood 103, the tip of the elastic tube 104 is dug into the groove 106 and, therefore, the transparent hood 103 and the elastic tube 104 are joined. This groove is coated with an adhesive in advance before joining and, therefore, dropout of both is prevented.

Figure 50:
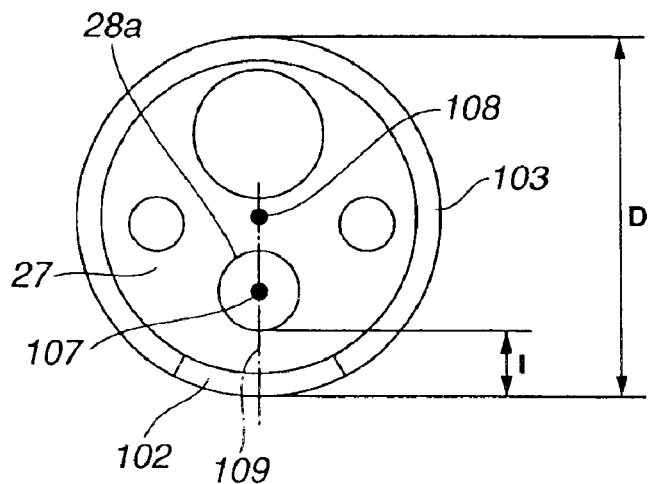
FIG. 50 is an enlarged sectional view of the section indicated by line F—F in FIG. 49.

Subsequently, as shown in FIG. 49, the tip portion of the insertion portion 29 of the endoscope 27 is press-fitted into the inside of the base end side of the elastic tube 104 of the endoscope tip hood 101 thus configured and, therefore, connection is performed. At the time of the connection, the connection is performed in order that the position of the hole 102 provided on the side surface of the transparent hood 103 is located on the diameter 109 bonding the axis center 107 of the channel 28a for forceps insertion and the axis center 108 of the endoscope 27, as shown in FIG. 50.

Regarding the connection of the endoscope tip hood 101 to the tip portion of the insertion portion 29 of the endoscope 27 as described above, the outer diameter φ D of the transparent hood 103 is designed, as shown in FIG. 48A, in order that the distance between the optical probe 8A and the living-body tissue 11 becomes a predetermined distance I when the optical probe 8A is protruded (from the channel 28a for forceps insertion) as shown in FIG. 49.

Consequently, according to the present embodiment, as described above, when the optical probe 8A is used by inserting through the channel 28a for forceps insertion from the forceps insertion hole 28 of the endoscope 27 and by protruding, the connection of the endoscope tip hood 101 to the tip portion of the insertion portion 29 of the endoscope 27 is performed as the aforementioned connection, and, therefore, the interval between the optical probe 8A and the living-body tissue 11 can be kept at a predetermined distance I in the case where it is intended to produce an optical tomogram of the living-body tissue 11 through the hole 102.

Since the endoscope 27 and the optical probe 8A are positioned relative to the living-body tissue 11 via the side surface of the endoscope tip hood 101, the interval I can be kept stably.

Furthermore, since the endoscope 27 and the side surface of the endoscope tip hood 101 can be held simultaneously relative to the living-body tissue 11, for example, even when the living-body tissue initiates pulsation, etc., no stress is applied to the optical probe 8A, and, therefore, the relative position of the optical probe 8A with respect to the living-body tissue 11 can be kept stably.

Figure 51:
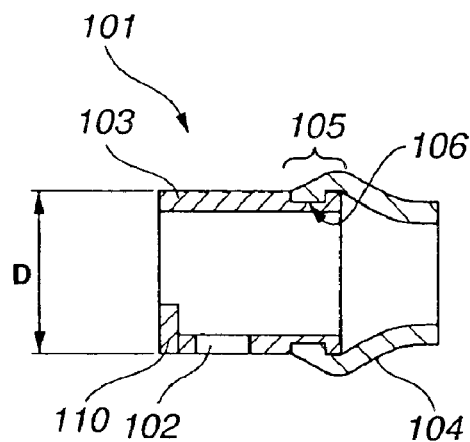
FIG. 51 is a vertical sectional view showing the configuration of a modified example of the endoscope tip hood, FIG. 52A to FIG. 56 relate to a nineteenth embodiment according to the present invention.

As shown in FIG. 51, a stopper 110 made of a transparent member may be provided integrally at the tip of the transparent hood 103 on the side of the side surface provided with the hole 102. This stopper 110 has an action of regulating the protrusion amount of the optical probe 8A in order that the optical axis of the light from the optical probe 8A passes through the center of the hole 102 or the vicinity thereof when the optical probe 8A is inserted through the channel 28a for forceps insertion from the forceps insertion hole 28 of the endoscope 27 and is protruded, and the tip of the optical probe 8A is made to contact with the stopper 110.

Therefore, it is possible to keep the interval between the optical probe 8A and the living-body tissue 11 at a desired distance I and, in addition, to protrude the tip of the optical probe 8A until the position of the hole 102 with ease by this stopper.

(Nineteenth Embodiment)

The nineteenth embodiment according to the present invention will be described with reference to FIG. 52A to FIG. 56. Since the present embodiment is nearly the same as the eighteenth embodiment, only different points will be described, the same constituents are indicated by the same reference numerals, and explanations thereof are omitted.

Figure 52B:
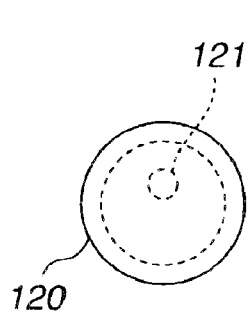
FIG. 52B is a front view viewed from the tip side shown in FIG. 52A.
Figure 52A:
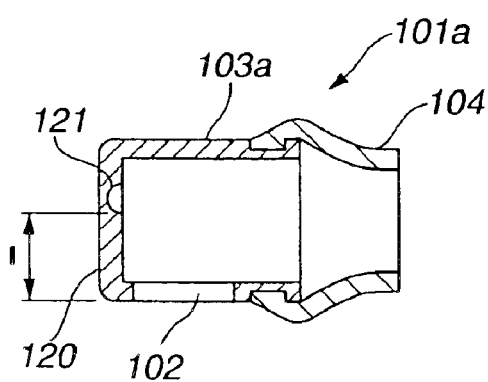
FIG. 52A is a configurational diagram showing the configuration of an endoscope tip hood according to the nineteenth embodiment.

The present embodiment is different from the eighteenth embodiment in the shape of the transparent hood 103 of the endoscope tip hood 101. As shown in FIG. 52A and FIG. 52B, the transparent hood 103a of the endoscope tip hood 101a is in the shape of a cylinder having a hole portion 102 on the side portion which includes closed surface 120 at the tip and which is made of, for example, plastic, having an excellent light transmission property.

Furthermore, the inner surface of the closed surface 120 is engraved hemispherically at the position distance I from the surface provided with the hole portion 102 intersecting the closed surface 120 and, therefore, a probe receiver 121 is provided.

This probe receiver 121 has an action of regulating the protrusion amount of the optical probe 8A in order that the optical axis of the light from the optical probe 8A passes through the center of the hole 102 or the vicinity thereof when the optical probe 8A is inserted through the channel 28a for forceps insertion from the forceps insertion hole 28 of the endoscope 27 and is protruded, and the tip of the optical probe 8A is made to contact with the probe receiver 121.

Other configuration is the same as that in the eighteenth embodiment.

Figure 53:
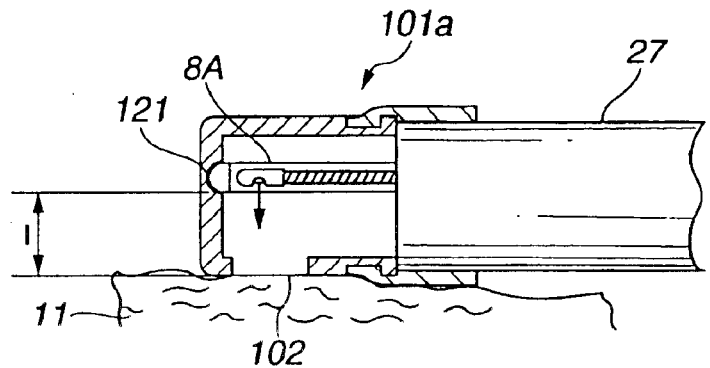
FIG. 53 is a diagram for explaining an action of positioning of an endoscope tip hood.

As shown in FIG. 53, the tip portion of the insertion portion 29 of the endoscope 27 is press-fitted into the inside of the base end side of the elastic tube 104 of the endoscope tip hood 101a thus configured and, therefore, connection is performed. At the time of the connection, in a manner similar to that in the eighteenth embodiment, the connection is performed in order that the position of the hole 102 provided on the side surface of the transparent hood 103a is located on the diameter bonding the axis center of the channel 28a for forceps insertion and the axis center of the endoscope 27.

Therefore, in the present embodiment, regarding the connection of the endoscope tip hood 101a to the tip portion of the insertion portion 29 of the endoscope 27, when the optical probe 8A is protruded from the channel 28a for forceps insertion as shown in FIG. 53, the tip of the optical probe 8A is fitted into the probe receiver 121. Consequently, the interval between the optical probe 8A and the living-body tissue 11 can be kept at a desired distance I and, in addition, the tip of the optical probe 8A can be protruded until the position of the hole 102 with ease by the probe receiver 121.

Since the optical probe 8A protruded is supported with two points of the probe receiver 121 and the outlet of the channel 28a for forceps insertion, the distance I can be kept further precisely compared to that in the eighteenth embodiment.

Since the closed surface 120 is provided on the transparent hood 103a, when suction function of the endoscope is used and the inside of the endoscope tip hood 101 is made to have a negative pressure, the living-body tissue 11 can be suctioned and protruded from the hole 102 toward the inside of the endoscope tip hood 101a.

Figure 54:
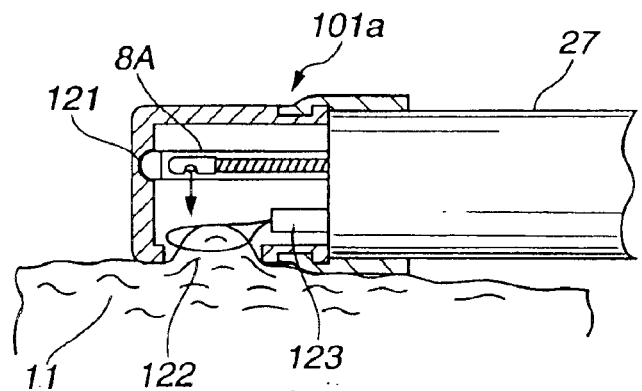
FIG. 54 is a diagram for explaining an action of performing therapy with a diathermic snare based on positioning of an endoscope tip hood.

Consequently, as shown in FIG. 54, for example, when a two-channel endoscope 27a having two channels for forceps insertion and the endoscope tip hood 101a are combined, a lesion portion 122 observed with the optical probe 8A inserted through the first channel for forceps insertion is suctioned and protruded, the lesion portion 122 is snared with a diathermic snare 123 inserted through the second channel for forceps insertion via the hole 102, a high-frequency current is applied and, therefore, resection can be performed.

Figure 55:
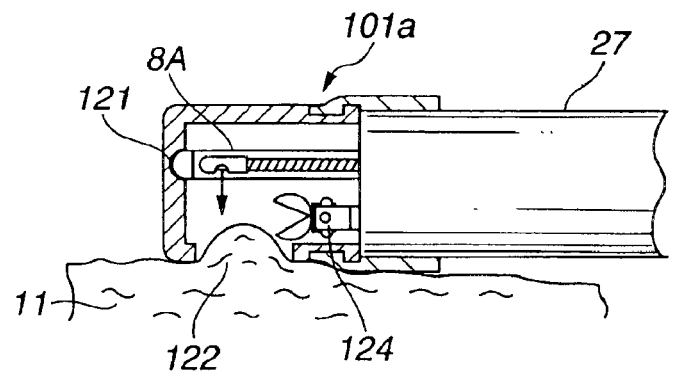
FIG. 55 is a diagram for explaining an action of performing biopsy with biopsy forceps based on positioning of an endoscope tip hood.

Likewise, as shown in FIG. 55, the lesion portion 122 observed with the optical probe 8A inserted through the first channel for forceps insertion is suctioned and protruded, and the lesion portion 122 can be subjected to biopsy with a biopsy forceps 124 inserted through the second channel for forceps insertion via the hole 102.

Figure 56:
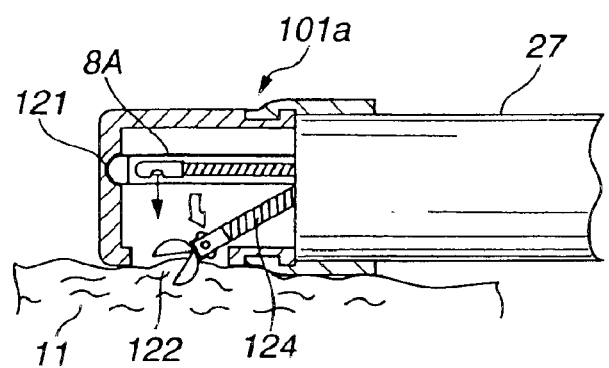
FIG. 56 is a diagram for explaining an action of performing biopsy with biopsy forceps while the forceps are elevated furthermore, FIG. 57 to FIG. 59 relate to a twentieth embodiment according to the present invention.

As shown in FIG. 56, when a two-channel endoscope 27b having a forceps elevator is used, biopsy can be performed by elevating the biopsy forceps 124 via the hole 102 without protrusion of the living-body tissue 11.

(Twentieth Embodiment)

The twentieth embodiment according to the present invention will be described with reference to FIG. 57 to FIG. 59. Since the present embodiment is nearly the same as the nineteenth embodiment, only different points will be described, the same constituents are indicated by the same reference numerals, and explanations thereof are omitted.

Figure 57:
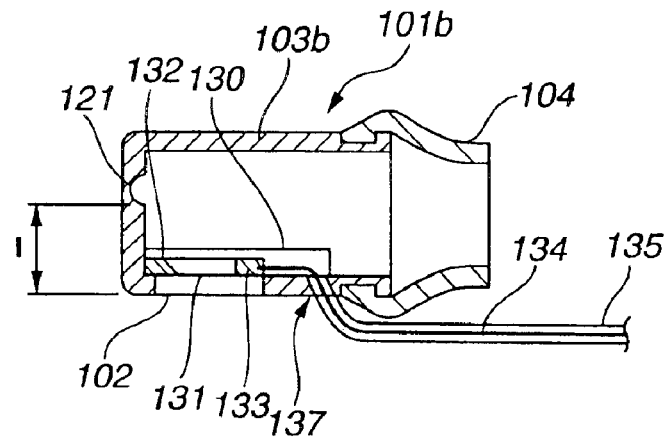
FIG. 57 is a vertical sectional view showing the configuration of an endoscope tip hood according to the twentieth embodiment.
Figure 58:
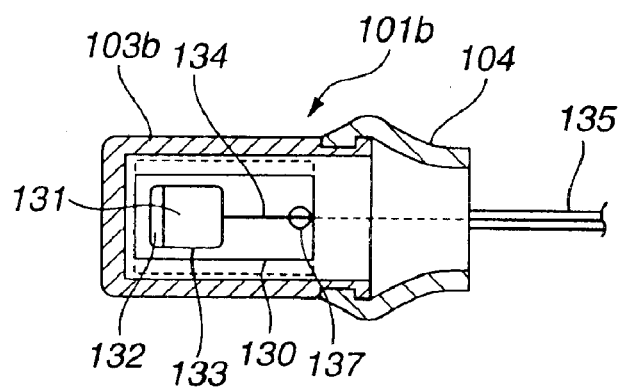
FIG. 58 is a plan sectional view of the endoscope tip hood shown in FIG. 57 viewed from the upper portion side.

As shown in FIG. 57 and FIG. 58, in a transparent hood 103b of a endoscope tip hood 101b according to the present embodiment, a slide edge 133 provided with an access hole 131 and a sharp portion 132 in a slide groove 130 formed on the inner surface facing the hole 102 is placed by fitting.

A wire 134 which has a length equivalent to that of the endoscope 27 and which is made of a metal is joined to the slide edge 133, and is guided outside the transparent hood 103b through a communicating path 135. A flexible tube 135 through which the wire 134 passes is connected to a communicating path opening portion on the outer perimeter of the transparent hood 130b.

Other configuration is the same as that in the nineteenth embodiment.

Figure 59:
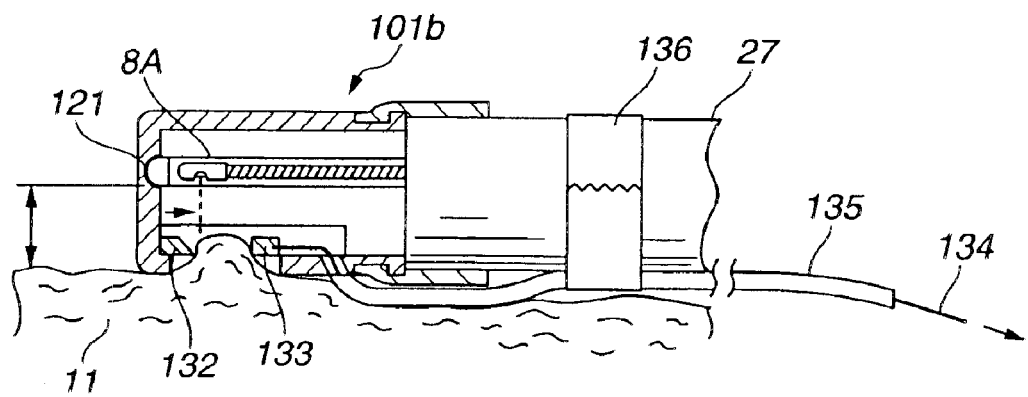
FIG. 59 is a diagram for explaining an action of an endoscope tip hood, FIG. 60A to FIG. 65 relate to a twenty-first embodiment according to the present invention.

As shown in FIG. 59, the tip portion of the insertion portion 29 of the endoscope 27 is press-fitted into the inside of the base end side of the elastic tube 104 of the endoscope tip hood 101b thus configured and, therefore, connection is performed. At the time of the connection, in a manner similar to that in the nineteenth embodiment, the connection is performed in order that the position of the hole 102 provided on the side surface of the transparent hood 103b may be located on the diameter bonding the axis center of the channel 28a for forceps insertion and the axis center of the endoscope 27.

When the endoscope tip hood 101b is connected to the endoscope 27 as described above, this tube 135 may be guided to the operation portion at hand along the insertion portion 29 of the endoscope 27 by using a medical tape 136, etc.

In a manner similar to that in the nineteenth embodiment, when the inside of the endoscope tip hood 101b is made to have a negative pressure, the living-body tissue 11 is protruded toward the inside, and a part of the living-body tissue 11 protruded contacts with the sharp portion 132. At this time, when the wire 134 is drawn from the near side, the slide edge 133 is slid toward the near side while being guided with the slide groove 130, and the living-body tissue 11 is cut with the sharp portion 132 at the portion contacted.

Consequently, in the present embodiment, in addition to the effects of the nineteenth embodiment, since it is unnecessary to use the two-channel endoscope when the living-body tissue 11 is resected, a thin endoscope can be used and, therefore, burdens on the patient can be reduced.

(Twenty-First Embodiment)

The twenty-first embodiment according to the present invention will be described with reference to FIG. 60A to FIG. 65.

Since the present embodiment is nearly the same as the eighteenth embodiment, only different points will be described, the same constituents are indicated by the same reference numerals, and explanations thereof are omitted.

Figure 60B:
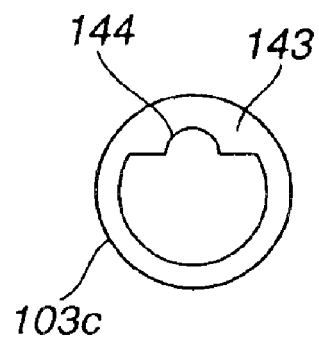
FIG. 60B is a front view of the endoscope tip hood viewed from the tip side shown in FIG. 60A.
Figure 60A:
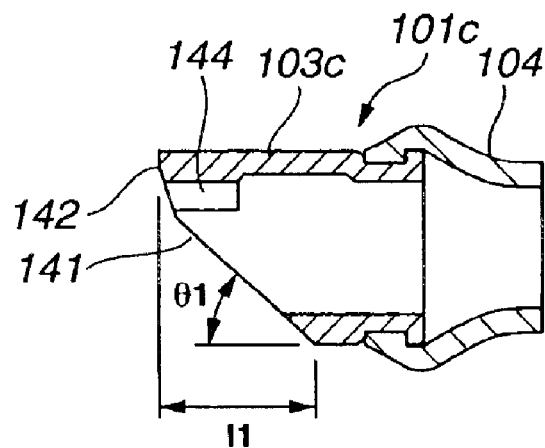
FIG. 60A is a configurational diagram showing the configuration of an endoscope tip hood according to the twenty-first embodiment.

As shown in FIGS. 60A and 60B, a transparent hood 103c of the endoscope tip hood 101c according to the present embodiment has the configuration in which no hole is provided on the side surface, an inclined portion 141 is provided at the tip side, and a chamfer portion 142, in which sharp edges at the tip of the inclination is rounded, is provided. A protuberance portion 143 is provided in the inside of the transparent hood 103c of the chamfer portion 142, and at the center thereof, a half-cylinder-shaped probe groove 144 is formed in the longitudinal axis direction of the transparent hood 103c. The inclined portion 141 is formed with the size of angle $\theta1$ and length l1 in accordance with the conditions of the specifications of the optical probe 8A to be combined as described below.

Other configuration is the same as that in the eighteenth embodiment.

Figure 61:
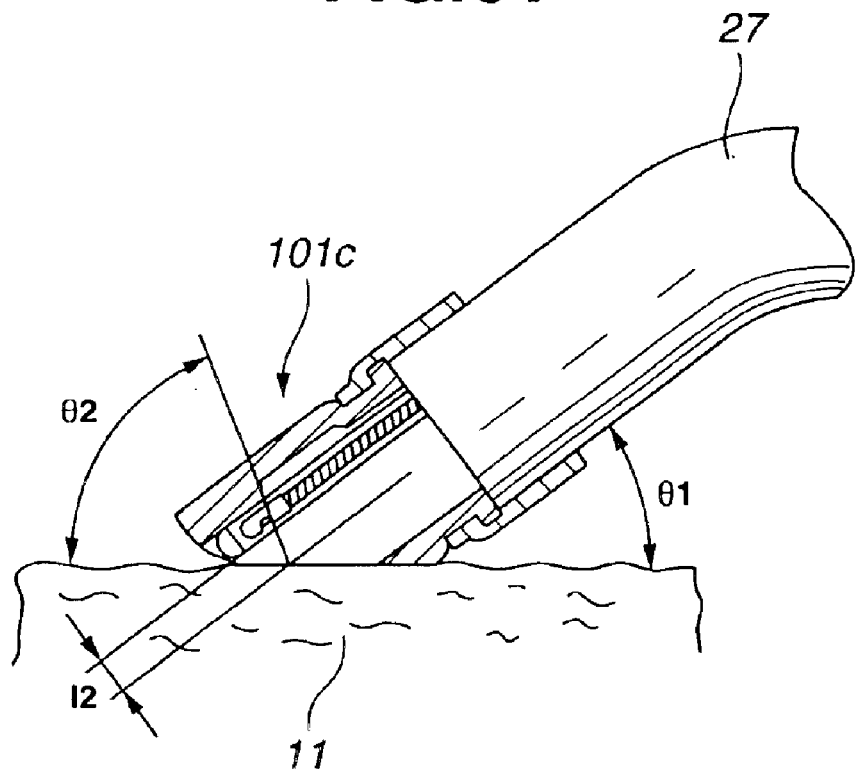
FIG. 61 is a first diagram for explaining an action of an endoscope tip hood.

As shown in FIG. 61, the tip portion of the insertion portion 29 of the endoscope 27 is press-fitted into the inside of the base end side of the elastic tube 104 of the endoscope tip hood 101c thus configured and, therefore, connection is performed.

Subsequently, the inclined portion 141 is made to contact with the living-body tissue 11, and regarding the optical probe 8A inserted through the channel 28a for forceps insertion of the endoscope 27, the upper half of the tip portion is fitted into the probe groove 144 and, therefore, is supported.

The light beam exiting from this optical probe 8A is designed in order that the optimum performance is exhibited when there is a positional relationship of angle $\theta2$ and length l2 relative to the living-body tissue 11.

Since the dimensions $\theta1$ and l1 of the inclined portion 141 of the endoscope tip hood 101c is previously designed beforehand in order that this positional relationship is achieved, the light beam emitted from the optical probe 8A and the angle $\theta2$ relative to the tissue can be achieved, and the distance l2 can be achieved by adjusting the insertion amount of the optical probe 8A. For example, $\theta1$ is adjusted at on the order of 45°, and $\theta2$ is adjusted at on the order of 70° to 80°.

As described above, in the present embodiment, the angle between the endoscope 27 and the living-body tissue 11 can be kept at $\theta1$, a light beam scanning locus on the living-body tissue 11 surface by an aiming beam can be identified with ease.

Figures 62A, 62B:
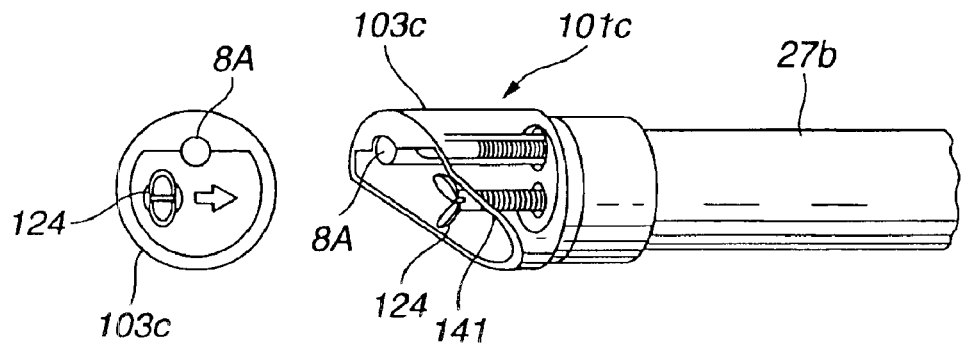
FIG. 62A is a second diagram for explaining an action of the endoscope tip hood.
FIG. 62B is a front view of FIG. 62A.
Figure 63:
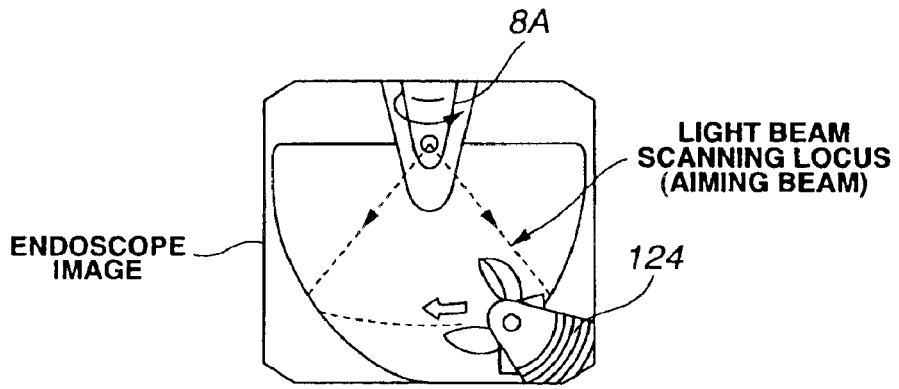
FIG. 63 is a third diagram for explaining an action of an endoscope tip hood.

When the design is performed in order that the inclined portion 141 of the endoscope tip hood 101c is combined with the two-channel endoscope 27b with a forceps elevator, as shown in FIG. 62A, it is possible to perform biopsy on the light beam scanning locus while the light beam scanning locus by an aiming beam is identified on the endoscope screen and the biopsy forceps are moved along the beam locus for targeting, as shown in FIG. 63.

Figure 64:
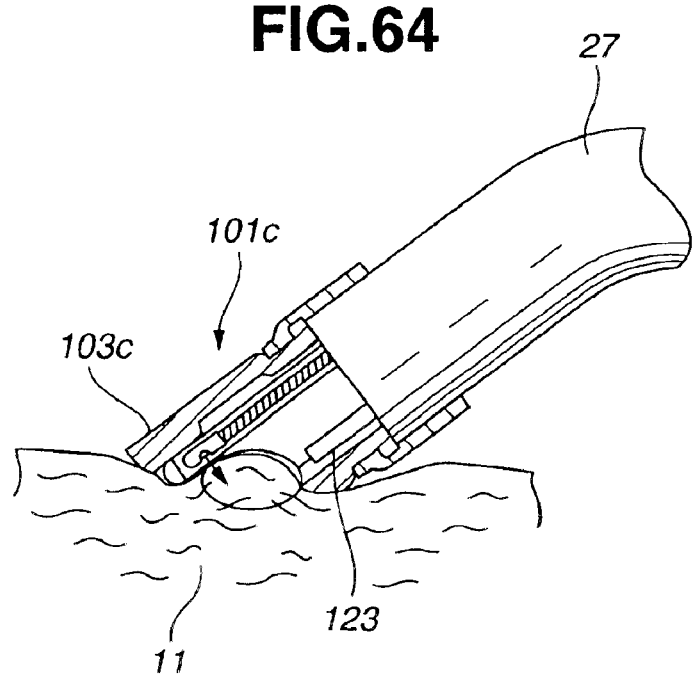
FIG. 64 is a fourth diagram for explaining an action of the endoscope tip hood.

Furthermore, as shown in FIG. 64, when a suction function of the endoscope 27 is used and the inside of the transparent hood 103c is made to have a negative pressure, the living-body tissue 11 can be protruded, and the protruded living-body tissue 11 can be resected with a diathermic snare 123 as well.

As described above, according to the present embodiment, in addition to the effects of the eighteenth embodiment, the interval and angle between the optical probe 8A and the living-body tissue 11 can be kept stably at a predetermined position according to the optical design, and, therefore, diagnostic performance is improved.

Since the relative position of the optical probe 8A with respect to the living-body tissue 11 is kept stably, blur of the tomogram is prevented, and, therefore, diagnostic performance and diagnosis speed are improved.

Since the tissue surface and light beam scanning locus of the optical probe 8A can be observed excellently with the endoscope, the inspection can be performed while comparison between the endoscope observation remark and the optical tomogram remark is performed with ease and, therefore, operating ease for the operator and diagnostic performance are improved.

By combination with a two-channel endoscope, biopsy and resection of the living-body tissue 11 can be performed with ease aiming at the light beam scanning locus under endoscope observation while optical tomography observation is performed and, therefore, operating ease for the operator and diagnostic performance are improved.

Figure 65:
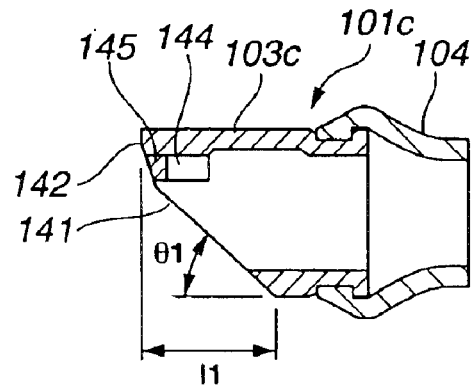
FIG. 65 is a vertical sectional view showing the configuration of a modified example of the endoscope tip hood, FIG. 66 and FIG. 67 relate to a twenty-second embodiment according to the present invention.

A stopper 145 may be provided at the tip of the probe groove 144 as shown in FIG. 65, and the insertion amount of the optical probe 8A can be adjusted with ease and reliability by this stopper 145.

(Twenty-Second Embodiment)

The twenty-second embodiment according to the present invention will be described with reference to FIG. 66 and FIG. 67.

Since the present embodiment is nearly the same as the twenty-first embodiment, only different points will be described, the same constituents are indicated by the same reference numerals, and explanations thereof are omitted.

Figure 66:
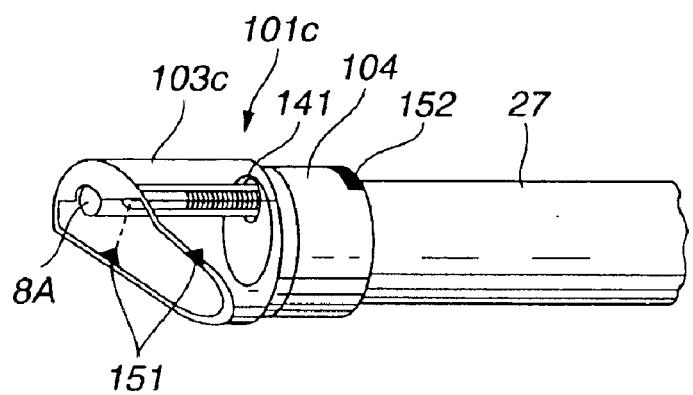
FIG. 66 is a configurational diagram showing the configuration of an endoscope tip hood according to the twenty-second embodiment.

As shown in FIG. 66, in the configuration of the present embodiment, beam position markings 151 are provided at the inclined portion 141 of the transparent hood 103c, and a phase marking 152 is provided at the end portion of the elastic tube 104.

The beam position markings 151 are provided at the position where the light beam and the inclined portion 141 intersect under the positional relationship in which the optical probe 8A is inserted in order that the interval L2 between the optical probe 8A and the living-body tissue 11 shown in FIG. 61 is kept. The phase marking 152 is provided at the position where the phase is the same as that of the probe groove 144. Other configuration is the same as that in the twenty-first embodiment.

In the twenty-first embodiment, the frontward or backward movement of the optical probe 8A has been adjusted while the interval between the surface of the optical probe 8A and the living-body tissue 11 is observed under the optical tomogram image and, therefore, the interval L2 shown in FIG. 61 has been adjusted. However, in the present embodiment, as is shown by the endoscope image in FIG. 67, the interval between the optical probe 8A and the living-body tissue 11 can be fixed at L2 with ease by adjusting the frontward or backward movement of the optical probe 8A under the endoscope in order that the light beam scanning locus intersect the beam position marking 151.

In the twenty-first embodiment, inconvenience is brought about beyond expectation in that, for example, when the endoscope tip hood 101c is fitted into the endoscope 27, the tip of the endoscope 27 is viewed from the front, the channel 28a for forceps insertion and the probe groove 144 are watched simultaneously while these phases (positions) must be made to coincide. However, in the present embodiment, this coincidence of the phases (positions) can be achieved with ease by performing insertion in order that the phases (positions) of the phase marking 152 and the channel 28a for forceps insertion coincide.

As described above, according to the present embodiment, in addition to the effects of the twenty-first embodiment, since adjustment of the distance between the living-body tissue 11 surface and the optical probe 8A can be performed with ease and precision by the beam position marking 151, operating ease for the operator and diagnostic performance are improved.

Since fitting of the endoscope tip hood 101c to the endoscope 27 can be performed with ease and reliability by the phase marking 152, operating ease for the operator and diagnostic performance are improved.

Figure 67:
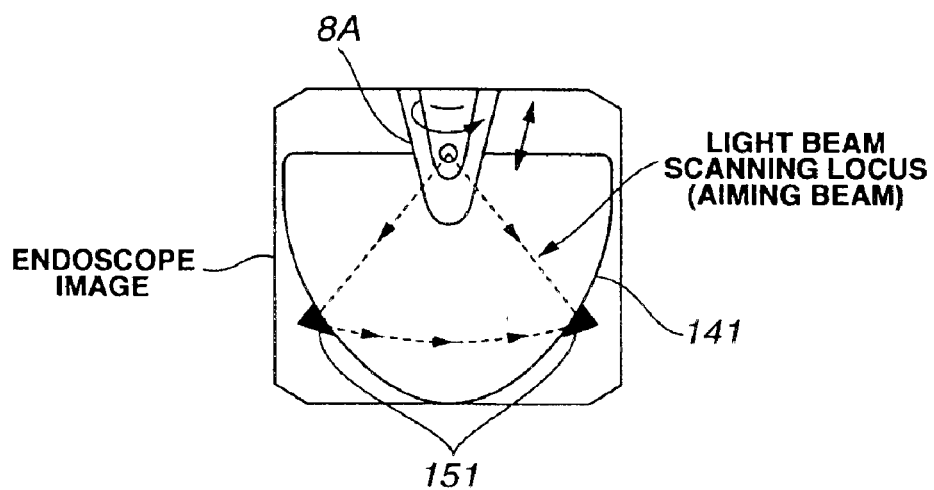
FIG. 67 is a diagram for explaining an action of an endoscope tip hood, FIG. 68A to FIG. 72 relate to a twenty-third embodiment according to the present invention.

It is self-evident that effects similar to those due to provision of the beam position marking 151 can be achieved by attaching the marking on the part of the screen at which the beam position marking 151 shown in the endoscope image in FIG. 67 is displayed, or by displaying the marking synthesized in a manner such as image processing.

It is self-evident that effects similar to those due to provision of the phase marking 152 can be achieved by attaching the marking along the shape of the inclined portion 144 on the screen at which the inclined portion 144 shown in the endoscope image in FIG. 67 is displayed, or by synthesizing the marking.

(Twenty-Third Embodiment)

The twenty-third embodiment according to the present invention will be described with reference to FIG. 68A to FIG. 72.

Since the present embodiment is nearly the same as the twenty-first embodiment, only different points will be described, the same constituents are indicated by the same reference numerals, and explanations thereof are omitted.

In the present embodiment, as shown in FIG. 68A, in the inside of the transparent hood 103c, a hollow circumferential direction communicating path 161 provided in the circumferential direction, and a plurality of longitudinal axis direction communicating paths 162 which are provided in the longitudinal axis direction while joining to the circumferential direction communicating path 161 and which are opened at the tip of the transparent hood 103c are provided.

The circumferential direction communicating path 161 is joined to a tube 163 having nearly the same length as that of the endoscope 27, and is adhered and fixed to the transparent hood 103c with a built-up adhesive. One end of the tube can be connected to a syringe 164 filled with dye. Other configuration is the same as that in the twenty-first embodiment.

In the present embodiment, as shown in FIG. 69, after the endoscope tip hood 101c is connected to the tip of the endoscope 27, the tube 163 is fixed along the endoscope 27 by using a medical tape 165, etc.

After a lesion portion 166 is found out with the optical probe 8A, the dye is injected into the tube 163, circumferential direction communicating path 161, and longitudinal axis direction communicating paths 162 in that order by pushing a syringe 164. Consequently, the dye is discharged from openings of the longitudinal axis direction communicating paths 162, and, therefore, marking 167 can be applied to the surroundings of the lesion portion 166.

As described above, according to the present embodiment, in addition to the effects of the twenty-first embodiment, since the lesion portion 166 found out with the optical probe 8A can be marked, a landmark for a later therapy, for example, biopsy and resection, can be provided.

Figure 70A:
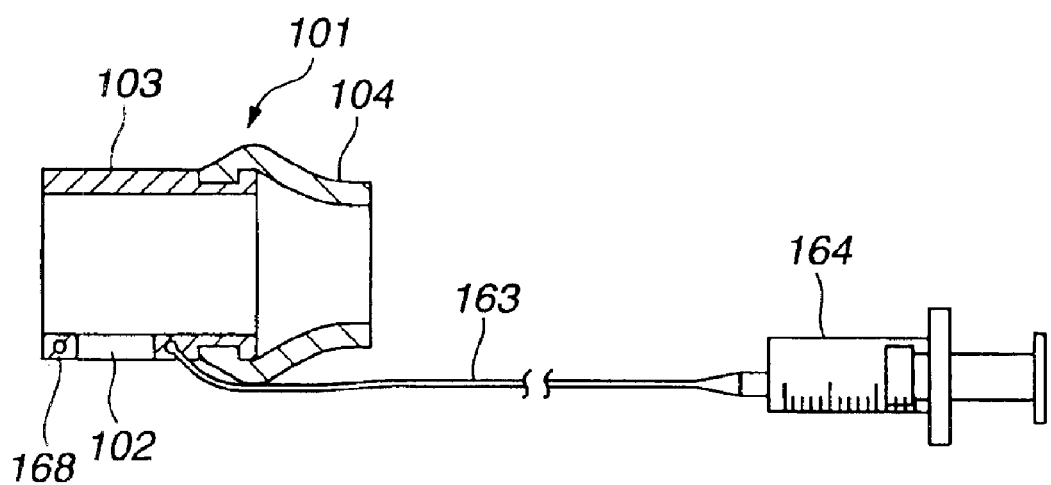
FIG. 70A is a vertical sectional view showing the configuration of a modified example of the endoscope tip hood.
Figure 70B:
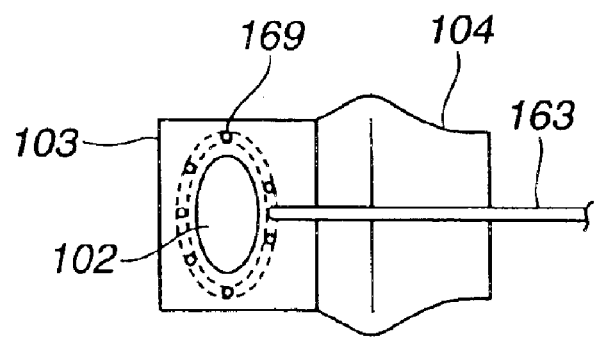
FIG. 70B is a bottom view viewed from the bottom side shown in FIG. 70A.

As shown in FIG. 70A and FIG. 70B, when the transparent hood 103 having the configuration similar to that in the eighteenth embodiment is provided with a communicating paths 168 and a plurality of communicating path openings 169 on the outer perimeter of the hole portion 102, and are connected to the tube 163 and the syringe 164, similar actions and effects can be achieved in the transparent hood 103 having the configuration similar to that in the eighteenth embodiment.

Figure 71:
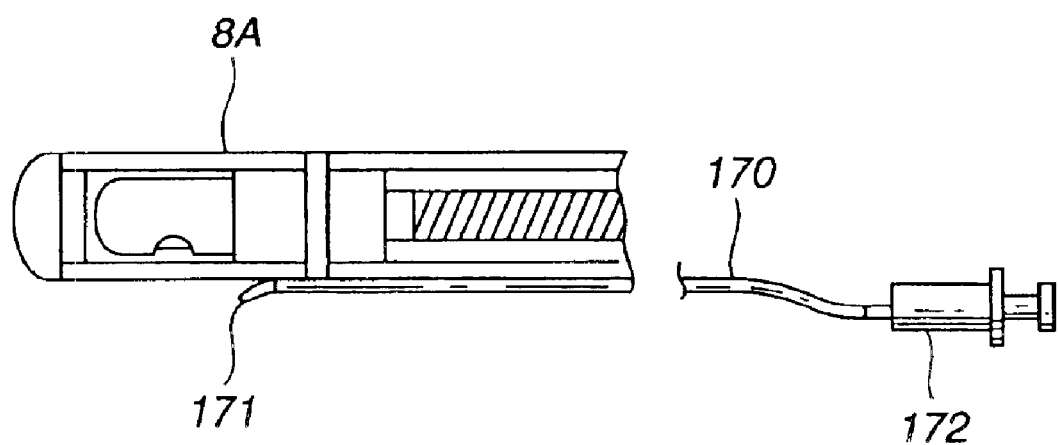
FIG. 71 is a diagram showing the configuration of an optical probe provided with a marking unit.

As shown in FIG. 71, a tube 170 may be placed along the optical probe 8A, a nozzle 171 may be connected to the tip side, and a syringe 172 may be connected to the rear end side.

By injecting the dye from the syringe 172, the dye is ejected from the nozzle 171 and, therefore, the lesion observed can be marked.

Figure 72:
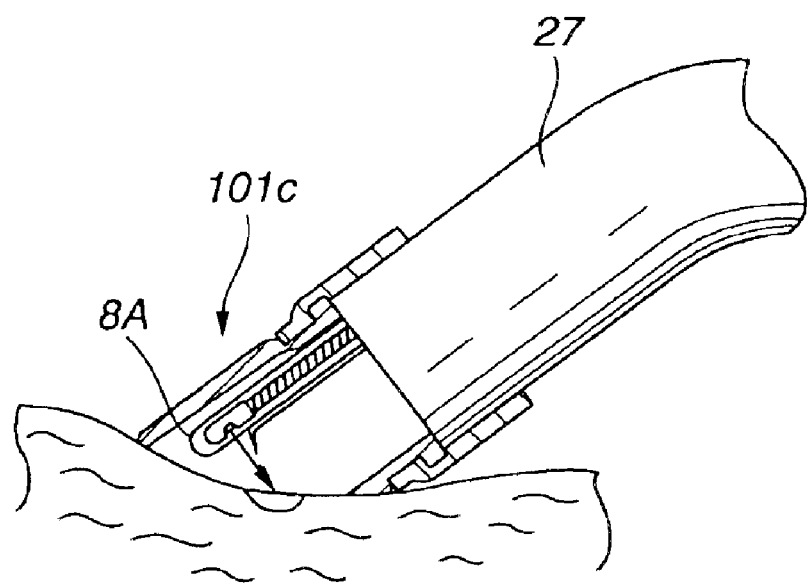
FIG. 72 is a diagram for explaining an action of an optical probe, FIG. 73A to FIG. 75 relate to a twenty-fourth embodiment according to the present invention.

As shown in FIG. 72, it is effective to combine with the endoscope tip hood 101c because positioning of the optical probe 8A becomes easy. In this example, the design is performed in order that dye is ejected at the focus position of the light beam. It may not be at the focus position, it may be back from the focus position, or intersection may be forward of the focus position in accordance with the purpose of the observation.

(Twenty-Fourth Embodiment)

The twenty-fourth embodiment according to the present invention will be described with reference to FIG. 73A to FIG. 75B.

Since the present embodiment is nearly the same as the twenty-first embodiment, only different points will be described, the same constituents are indicated by the same reference numerals, and explanations thereof are omitted.

As shown in FIG. 73A, in the present embodiment, an electrode 181 made of metal is attached to the tip (inclined portion 144) of the transparent hood 103c, and is electrically connected to an electric wire 182 imbedded in the inside of the transparent hood in the longitudinal axis direction.

The other end of this electric wire 182 exits outside the transparent hood 103c and is connected to a covered electric wire 183 having nearly the same length as that of the endoscope 27. The other end of the covered electric wire 183 is connected to a high-frequency power source 184. This covered electric wire 183 is adhered and fixed to the transparent hood 103c with a built-up adhesive. Other configuration is the same as that in the twenty-first embodiment.

In the present embodiment, as shown in FIG. 74, a ground is established for the patient by, for example, attaching a counter electrode plate on the body surface. After a lesion portion 185 is found out with the optical probe 8A, the high-frequency power source 184 is switched on, and a high-frequency current is applied to the electrode 181. Consequently, the surface of the living-body tissue 11, which is an electrode part, reaches a high temperature, and is denatured or carbonized. The lesion part is thereby marked.

As described above, according to the present embodiment, in addition to the effects of the twenty-first embodiment, since the marking is unlikely to disappear and is maintained compared to that in the twenty-third embodiment, it is possible to take much time before the subsequent therapy or observation.

Figure 75A:
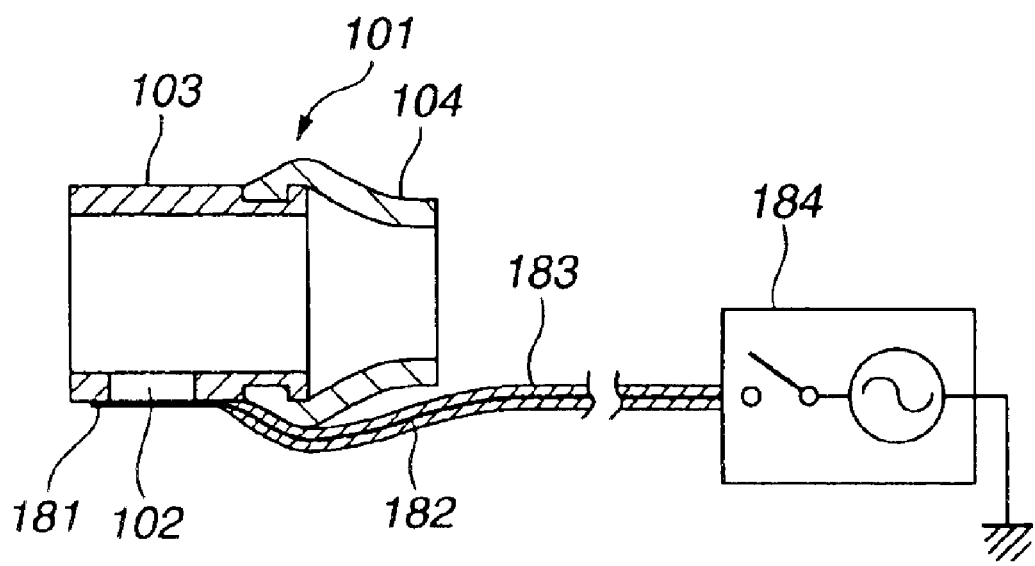
FIG. 75A is a vertical sectional view showing the configuration of a modified example of the endoscope tip hood.
Figure 75B:
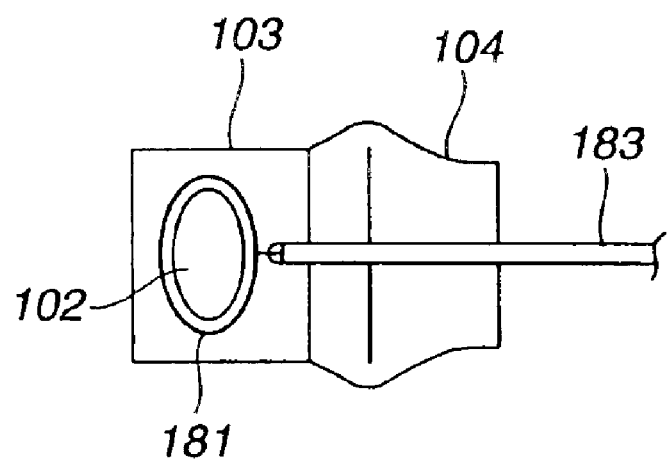
FIG. 75B is a bottom view viewed from the bottom side shown in FIG. 75A, FIG. 76 to FIG. 79 relate to a twenty-fifth embodiment according to the present invention.

Similar actions and effects can be achieved by an application to the transparent hood 103 having the configuration similar to that in the eighteenth embodiment. That is, it is essential that the electrode 181 is attached to the periphery of the hole portion 102 of the transparent hood 103, is connected to the covered electric wire 183, as shown in FIGS. 75A and 75B, and other configuration is similar to that shown in FIG. 73A.

(Twenty-Fifth Embodiment)

The twenty-fifth embodiment according to the present invention will be described with reference to FIG. 76 to FIG. 79.

Since the present embodiment is nearly the same as the twenty-first embodiment, only different points will be described, the same constituents are indicated by the same reference numerals, and explanations thereof are omitted.

Figure 76:
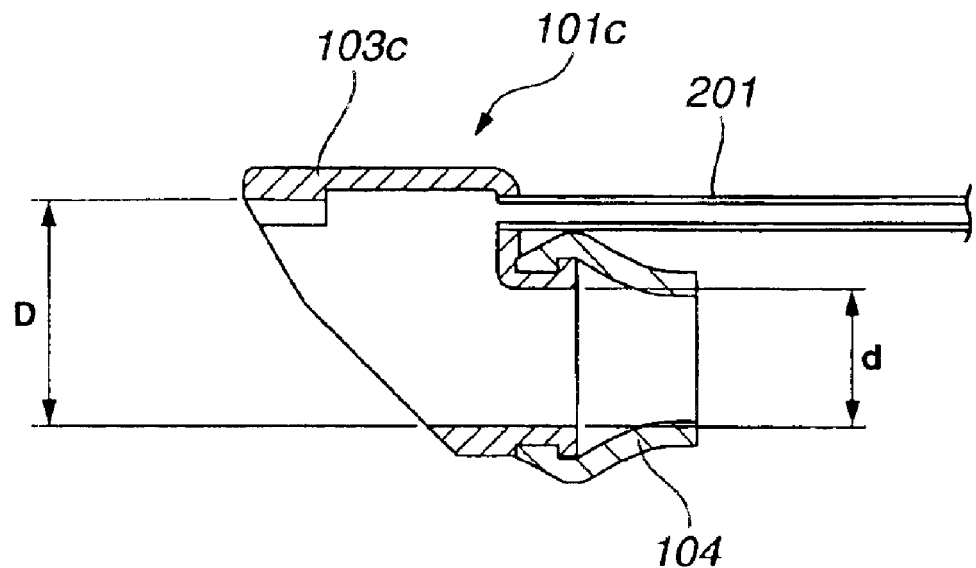
FIG. 76 is a vertical sectional view showing the configuration of an endoscope tip hood according to the twenty-fifth embodiment.

As shown in FIG. 76, in the present embodiment, the transparent hood 103c is formed in order that the inner diameter D of the connection portion 105 side is larger than the inner diameter d of the connection portion 105, and the axes of these inner diameters does not coincide with each other. A flexible tube 201 having an inner diameter capable of being inserted with the optical probe 8A is connected to the rear end side surface of the part having the inner diameter of D, and is adhered and fixed while being communicated with the inside of the transparent hood 103c. Other configuration is the same as that in the twenty-first embodiment.

Figure 77:
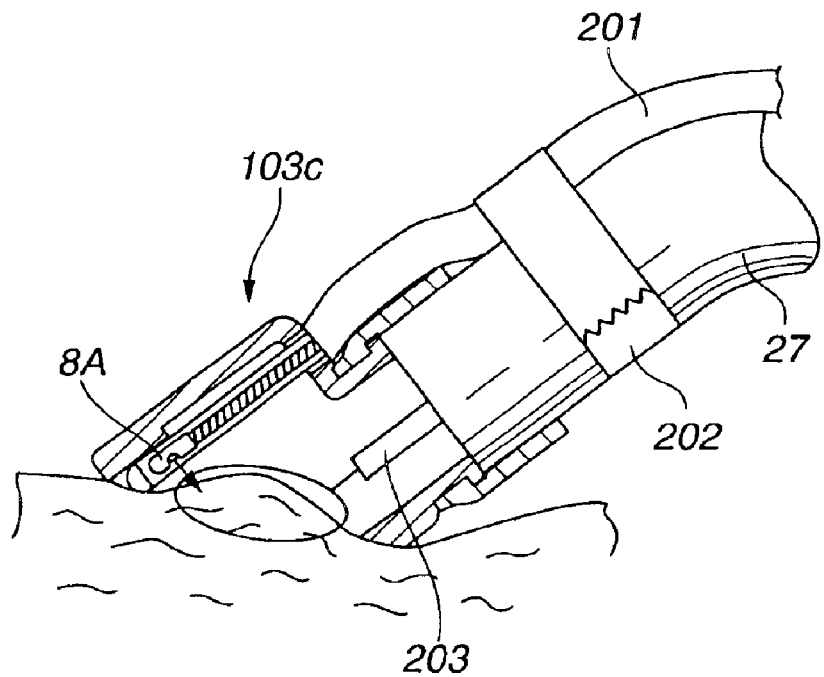
FIG. 77 is a first diagram for explaining an action of an endoscope tip hood.

In the present embodiment, the tube 201 is fixed along the endoscope 27 by using a medical tape 202, etc., as shown in FIG. 77. The optical probe 8A is inserted into the tube 201 from the near side, and observation is performed.

In the present embodiment, the design is performed in order that the positional relationship between the light beam and the living-body tissue 11 is fixed at a desired position in a manner as described in the twenty-first embodiment as well.

Figure 78:
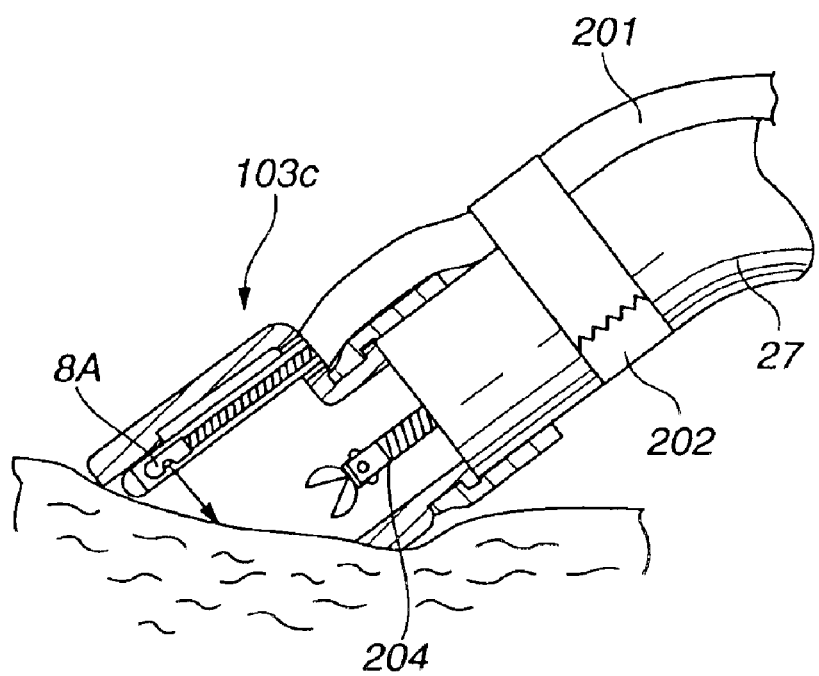
FIG. 78 is a second diagram for explaining an action of the endoscope tip hood.

Since the optical probe 8A is inserted from the tube 201 attached externally, even when a one-channel endoscope is used, a diathermic snare 203 can be inserted into the endoscope channel at the same time and, therefore, resection can be performed. It is also possible to perform biopsy with a biopsy forceps 204, as shown in FIG. 78.

As described above, according to the present embodiment, in addition to the effects of the twenty-first embodiment, tomogram diagnosis and therapy, for example, resection and biopsy, can be performed simultaneously without the use of the two-channel endoscope.

Figure 79:
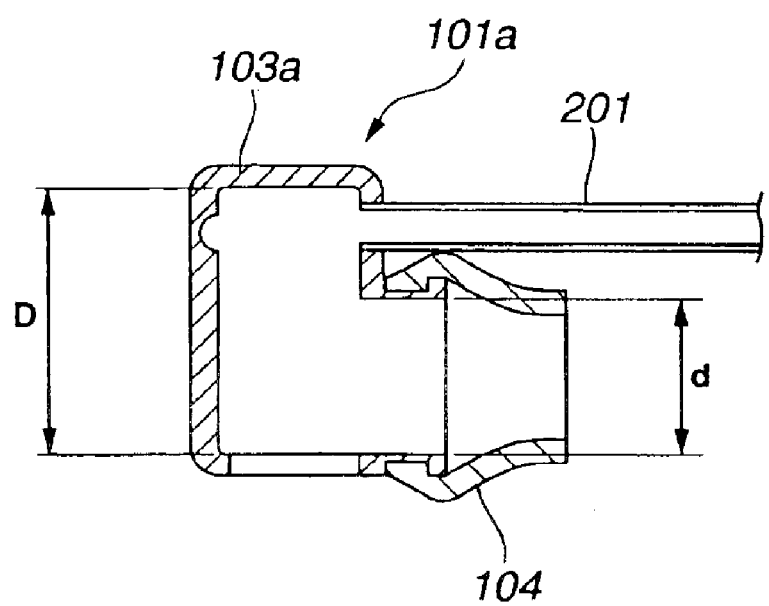
FIG. 79 is a vertical sectional view showing the configuration of a modified example of the endoscope tip hood.

As shown in FIG. 79, actions-effects similar to those in the case where the one-channel endoscope is used can be achieved by an application of similar configuration to the transparent hood 103a according to the nineteenth embodiment.

Furthermore, embodiments having a configuration in which each of the aforementioned embodiments is combined partially or the like are included in the present invention.

Also, having described the preferred embodiments of the invention referring to the accompanying drawings, it should be understand that the present invention is not limited to those precise embodiments and various changes and modifications thereof could be made by one skilled in the art without departing from the spirit or scope of the invention as defined in the appended claims.

What is claimed is:

1. A positioning unit provided at the tip of an endoscope used together with an optical scanning probe which is inserted through a forceps channel of the endoscope and which includes an exit portion for making scanning light exit in order to produce a tomogram of a test part, comprising a scanning light passage hole for passing the scanning light exiting from the exit portion to the position corresponding to the exit portion of the optical scanning probe when the optical scanning probe is protruded by a predetermined amount from the tip of the endoscope in the longitudinal direction of the endoscope.

2. The positioning unit according to claim 1, wherein a light beam exiting from the optical scanning probe and the test part intersect at a predetermined angle, and the exit portion and the light passage hole are kept at a predetermined interval.

3. The positioning unit according to claim 2, wherein the endoscope comprises the first channel for inserting the optical scanning probe and the second channel for inserting an endo-therapy product, and the tip opening of the second channel is located on the extended line of the scanning position of the light beam.

4. The positioning unit according to claim 2, wherein the positioning unit comprises a hollow hood in order to protrude the optical scanning probe in the lumen thereof, and the light transmission hole is composed of a side surface hole opened at the side surface of the hood in the longitudinal axis direction.

5. The positioning unit according to claim 3, wherein the positioning unit comprises a hollow hood in order to protrude the optical scanning probe in the lumen thereof, and the light transmission hole is composed of a side surface hole opened at the side surface of the hood in the longitudinal axis direction.

6. An endoscope device comprising an optical scanning probe which is inserted through a forceps channel of an endoscope and which includes an exit portion for making scanning light exit in order to produce a tomogram of a test part and a positioning unit provided at the tip of the endoscope, wherein marking which indicates the scanning position of the scanning light by the optical scanning probe in displayed field of view of the endoscope is provided.

7. The endoscope device according to claim 5, wherein marking which indicates the position of the positioning unit located in an observation view of the endoscope in displayed field of view of the endoscope is provided.

8. An optical scanning probe device comprising:

an optical scanning probe which is inserted through a forceps channel of an endoscope and which includes an exit portion for making scanning light exit in order to produce a tomogram of a test part based on low coherence interference; and a positioning unit which is provided at the tip of the endoscope and which includes a scanning light passage hole for passing the scanning light exiting from the exit portion to the position corresponding to the exit portion of the optical scanning probe when the optical scanning probe is protruded by a predetermined amount from the tip of the endoscope in the longitudinal direction of the endoscope.

* * * * *